(12) United States Patent
Ghosh

(10) Patent No.: US 11,701,517 B2
(45) Date of Patent: Jul. 18, 2023

(54) CARDIAC RESYNCHRONIZATION THERAPY USING ACCELEROMETER

(71) Applicant: Medtronic, Inc., Minneapolis, MN (US)

(72) Inventor: Subham Ghosh, Blaine, MN (US)

(73) Assignee: Medtronic, Inc., Minneapolis, MN (US)

(*) Notice: Subject to any disclaimer, the term of this patent is extended or adjusted under 35 U.S.C. 154(b) by 251 days.

(21) Appl. No.: 16/793,193

(22) Filed: Feb. 18, 2020

(65) Prior Publication Data

US 2020/0289829 A1  Sep. 17, 2020

Related U.S. Application Data

(60) Provisional application No. 62/816,847, filed on Mar. 11, 2019.

(51) Int. Cl.
| | | |
|---|---|---|
| *A61N 1/365* | (2006.01) | |
| *A61N 1/362* | (2006.01) | |
| *A61N 1/368* | (2006.01) | |
| *A61N 1/39* | (2006.01) | |
| *A61N 1/37* | (2006.01) | |

(52) U.S. Cl.
CPC ......... *A61N 1/36585* (2013.01); *A61N 1/368* (2013.01); *A61N 1/3624* (2013.01); *A61N 1/36578* (2013.01); *A61N 1/3706* (2013.01); *A61N 1/3937* (2013.01); *A61N 1/3956* (2013.01)

(58) Field of Classification Search
CPC .... A61N 1/368; A61N 1/3756; A61N 1/3682; A61N 1/3622
See application file for complete search history.

(56) References Cited

U.S. PATENT DOCUMENTS

| | | | |
|---|---|---|---|
| 4,546,777 | A | 10/1985 | Groch et al. |
| 5,154,170 | A | 10/1992 | Bennett et al. |
| 5,554,177 | A | 9/1996 | Kieval et al. |
| 5,562,711 | A | 10/1996 | Yerich et al. |
| 6,869,404 | B2 | 3/2005 | Schulhauser et al. |
| 6,980,675 | B2 | 12/2005 | Evron et al. |

(Continued)

FOREIGN PATENT DOCUMENTS

WO    2017075193 A1    5/2017

OTHER PUBLICATIONS (PCT/US2020/019877) PCT Notification of Transmittal of the International Search Report and the Written Opinion of the International Searching Authority, dated Jan. 00, 0000, 14 pages.

*Primary Examiner* — George R Evanisko
(74) *Attorney, Agent, or Firm* — Mueting Raasch Group

(57) ABSTRACT

An implantable medical device includes a plurality of electrodes to detect electrical activity, a motion detector to detect mechanical activity, and a controller to determine at least one electromechanical interval based on at least one of electrical activity and mechanical activity. The activity detected may be in response to delivering a pacing pulse according to an atrioventricular (AV) pacing interval using the second electrode. The electromechanical interval may be used to adjust the AV pacing interval. The electromechanical interval may be used to determine whether cardiac therapy is acceptable or whether atrial or ventricular remodeling is successful.

24 Claims, 20 Drawing Sheets

(56) References Cited

U.S. PATENT DOCUMENTS

| | | |
|---|---|---|
| 7,035,684 B2 | 4/2006 | Lee |
| 7,286,866 B2 | 10/2007 | Okerlund et al. |
| 7,308,297 B2 | 12/2007 | Reddy et al. |
| 7,308,299 B2 | 12/2007 | Burrell et al. |
| 7,321,677 B2 | 1/2008 | Evron et al. |
| 7,346,381 B2 | 3/2008 | Okerlund et al. |
| 7,454,248 B2 | 11/2008 | Burrell et al. |
| 7,499,743 B2 | 3/2009 | Vass et al. |
| 7,565,190 B2 | 7/2009 | Okerlund et al. |
| 7,587,074 B2 | 9/2009 | Zarkh et al. |
| 7,599,730 B2 | 10/2009 | Hunter et al. |
| 7,613,500 B2 | 11/2009 | Vass et al. |
| 7,742,629 B2 | 6/2010 | Zarkh et al. |
| 7,747,047 B2 | 6/2010 | Okerlund et al. |
| 7,778,685 B2 | 8/2010 | Evron et al. |
| 7,778,686 B2 | 8/2010 | Vass et al. |
| 7,813,785 B2 | 10/2010 | Okerlund et al. |
| 7,996,063 B2 | 8/2011 | Vass et al. |
| 8,060,185 B2 | 11/2011 | Hunter et al. |
| 8,401,616 B2 | 3/2013 | Verard et al. |
| 9,119,959 B2 | 9/2015 | Rys et al. |
| 9,289,612 B1 | 3/2016 | Sambelashvili et al. |
| 9,320,446 B2 | 4/2016 | Gillberg et al. |
| 9,399,140 B2 | 7/2016 | Cho et al. |
| 9,643,013 B2 | 5/2017 | Sambelashvili et al. |
| 9,675,579 B2 | 6/2017 | Rock et al. |
| 9,707,399 B2 | 7/2017 | Zielinski et al. |
| 9,724,519 B2 | 8/2017 | Demmer et al. |
| 9,789,319 B2 | 10/2017 | Sambelashvili |
| 10,390,720 B2 | 8/2019 | Anderson et al. |
| 2005/0008210 A1 | 1/2005 | Evron et al. |
| 2006/0074285 A1 | 4/2006 | Zarkh et al. |
| 2011/0112398 A1 | 5/2011 | Zarkh et al. |
| 2013/0116739 A1 | 5/2013 | Brada et al. |
| 2013/0123872 A1 | 5/2013 | Bornzin et al. |
| 2014/0323882 A1 | 10/2014 | Ghosh et al. |
| 2014/0323892 A1 | 10/2014 | Ghosh et al. |
| 2014/0371832 A1 | 12/2014 | Ghosh |
| 2014/0371833 A1 | 12/2014 | Ghosh et al. |
| 2016/0023000 A1* | 1/2016 | Cho .................. A61N 1/36578 607/18 |
| 2016/0067500 A1* | 3/2016 | Demmer ............ A61N 1/36592 607/18 |
| 2016/0129262 A1* | 5/2016 | Sheldon ............. A61N 1/3688 607/17 |
| 2018/0326215 A1 | 11/2018 | Ghosh |
| 2019/0126050 A1* | 5/2019 | Shuros ............... A61N 1/36521 |
| 2019/0290909 A1 | 9/2019 | Ghosh et al. |
| 2020/0338356 A1* | 10/2020 | Anderson ........... A61N 1/3756 |

* cited by examiner

CARDIAC RESYNCHRONIZATION THERAPY USING ACCELEROMETER

The present technology is generally related to medical devices and, in particular, medical devices for cardiac resynchronization therapy.

The cardiac conduction system includes the sinus atrial (SA) node, the atrioventricular (AV) node, the bundle of His, bundle branches and Purkinje fibers. A heart-beat is initiated in the SA node, which may be described as the natural "pacemaker" of the heart. An electrical impulse arising from the SA node causes the atrial myocardium to contract. The signal is conducted to the ventricles via the AV node which inherently delays the conduction to allow the atria to stop contracting before the ventricles begin contracting thereby providing proper AV synchrony. The electrical impulse is conducted from the AV node to the ventricular myocardium via the bundle of His, bundle branches, and Purkinje fibers.

Patients with a conduction system abnormality, such as poor AV node conduction or poor SA node function, may receive an implantable medical device (IMD), such as a pacemaker, to restore a more normal heart rhythm and AV synchrony. Some types of IMDs, such as cardiac pacemakers, implantable cardioverter defibrillators (ICDs), or cardiac resynchronization therapy (CRT) devices, provide therapeutic electrical stimulation to a heart of a patient via electrodes on one or more implantable endocardial, epicardial, or coronary venous leads that are positioned in or adjacent to the heart. The therapeutic electrical stimulation may be delivered to the heart in the form of pulses or shocks for pacing, cardioversion, or defibrillation. In some cases, an IMD may sense intrinsic depolarizations of the heart, and control the delivery of therapeutic stimulation to the heart based on the sensing.

Delivery of therapeutic electrical stimulation to the heart can be useful in addressing cardiac conditions such as ventricular dyssynchrony that may occur in patients. Ventricular dyssynchrony may be described as a lack of synchrony or a difference in the timing of contractions in different ventricles of the heart. Significant differences in timing of contractions can reduce cardiac efficiency. CRT, delivered by an IMD to the heart, may enhance cardiac output by resynchronizing the electromechanical activity of the ventricles of the heart. CRT is sometimes referred to as "triple chamber pacing" because of pacing the right atrium, right ventricle, and left ventricle.

Cardiac arrhythmias may be treated by delivering electrical shock therapy for cardioverting or defibrillating the heart in addition to cardiac pacing, for example, from an ICD, which may sense a patient's heart rhythm and classify the rhythm according to an arrhythmia detection scheme in order to detect episodes of tachycardia or fibrillation. Arrhythmias detected may include ventricular tachycardia (VT), fast ventricular tachycardia (FVT), ventricular fibrillation (VF), atrial tachycardia (AT) and atrial fibrillation (AT). Anti-tachycardia pacing (ATP), a painless therapy, can be used to treat ventricular tachycardia (VT) to substantially terminate many monomorphic fast rhythms. While ATP is painless, ATP may not deliver effective therapy for all types of VTs. For example, ATP may not be as effective for polymorphic VTs, which has variable morphologies. Polymorphic VTs and ventricular fibrillation (VFs) can be more lethal and may require expeditious treatment by shock.

Dual chamber medical devices are available that include a transvenous atrial lead carrying electrodes that may be placed in the right atrium and a transvenous ventricular lead carrying electrodes that may be placed in the right ventricle via the right atrium. The dual chamber medical device itself is generally implanted in a subcutaneous pocket and the transvenous leads are tunneled to the subcutaneous pocket. A dual chamber medical device may sense atrial electrical signals and ventricular electrical signals and can provide both atrial pacing and ventricular pacing as needed to promote a normal heart rhythm and AV synchrony. Some dual chamber medical devices can treat both atrial and ventricular arrhythmias.

Intracardiac medical devices, such as a leadless pacemaker, have been introduced or proposed for implantation entirely within a patient's heart, eliminating the need for transvenous leads. A leadless pacemaker may include one or more electrodes on its outer housing to deliver therapeutic electrical signals and/or sense intrinsic depolarizations of the heart. Intracardiac medical devices may provide cardiac therapy functionality, such as sensing and pacing, within a single chamber of the patient's heart. Single chamber intracardiac devices may also treat either atrial or ventricular arrhythmias or fibrillation. Some leadless pacemakers are not intracardiac and may be positioned outside of the heart and, in some examples, may be anchored to a wall of the heart via a fixation mechanism.

In some patients, single chamber devices may adequately address the patient's needs. However, single chamber devices capable of only single chamber sensing and therapy may not fully address cardiac conduction disease or abnormalities in all patients, for example, those with some forms of AV dyssynchrony or tachycardia. Dual chamber sensing and/or pacing functions, in addition to ICD functionality in some cases, may be used to restore more normal heart rhythms.

SUMMARY

The techniques of this disclosure generally relate to optimizing cardiac resynchronization therapy (CRT) based on the electrical or mechanical activity of the patient's heart, which may be detected using a motion detector, such as an accelerometer. The electrical and/or mechanical activity may be used to determine whether effective cardiac therapy is being delivered or effective remodeling of the patient's heart is indicated over time. Various implantable medical devices may provide cardiac therapy using the cardiac conduction system or left ventricular myocardium implantable, for example, through the right atrium to the left ventricle (e.g., ventricle-from-atrium, or VfA) or through the coronary sinus. Non-limiting examples of cardiac therapy include single chamber or multiple chamber pacing (e.g., dual or triple chamber pacing), atrioventricular synchronous pacing, asynchronous pacing, triggered pacing, cardiac resynchronization pacing, or tachycardia-related therapy. In general, a tissue-piercing electrode may be implantable in the basal region, septal region, or basal-septal region adjacent to or within the left ventricular myocardium of the patient's heart.

In one aspect, the present disclosure provides an implantable medical device including a plurality of electrodes. The plurality of electrodes includes a first electrode to be implanted in the atrium of a patient's heart to deliver cardiac therapy or sense electrical activity of the atrium of the patient's heart and a second electrode to be implanted in a septal wall of the patient's heart distal to the first electrode and to deliver cardiac therapy to or sense electrical activity of the ventricle of the patient's heart. The device also includes a motion detector to detect mechanical activity of the patient's heart, a therapy delivery circuit operably coupled to the plurality of electrodes to deliver cardiac therapy to the patient's heart, and a sensing circuit operably coupled to the plurality of electrodes to sense electrical activity of the patient's heart and the motion detector to sense mechanical activity of the patient's heart. The device also includes a controller having processing circuitry operably coupled to the therapy delivery circuit and the sensing circuit. The controller is configured to deliver a pacing pulse according to an atrioventricular (AV) pacing interval using the second electrode, determine at least one electromechanical interval based on at least one of electrical activity and mechanical activity in response to delivering the pacing pulse, and adjust the AV pacing interval based on the at least one electromechanical interval.

In another aspect, the present disclosure provides an implantable medical device including a plurality of electrodes. The plurality of electrodes includes a first electrode to be implanted in the atrium of a patient's heart to deliver cardiac therapy or sense electrical activity of the atrium of the patient's heart and a second electrode to be implanted in a septal wall of the patient's heart distal to the first electrode and to deliver cardiac therapy to or sense electrical activity of the ventricle of the patient's heart. The device also includes a motion detector to detect mechanical activity of the patient's heart, a therapy delivery circuit operably coupled to the plurality of electrodes to deliver cardiac therapy to the patient's heart, and a sensing circuit operably coupled to the plurality of electrodes to sense electrical activity of the patient's heart and the motion detector to sense mechanical activity of the patient's heart. The device also includes a controller having processing circuitry operably coupled to the therapy delivery circuit and the sensing circuit. The controller is configured to detect electrical activity from the first electrode indicating atrial activation, detect mechanical activity from the motion detector indicating atrial contraction, determine at least one electromechanical interval based on the detected atrial activation and the detected atrial contraction, and determine whether repeated measurements of the at least one electromechanical interval indicate atrial remodeling.

In another aspect, the present disclosure provides an implantable medical device including a plurality of electrodes. The plurality of electrodes includes a first electrode to be implanted in the atrium of a patient's heart to deliver cardiac therapy or sense electrical activity of the atrium of the patient's heart and a second electrode to be implanted in a septal wall of the patient's heart distal to the first electrode and to deliver cardiac therapy to or sense electrical activity of the ventricle of the patient's heart. The device also includes a motion detector to detect mechanical activity of the patient's heart, a therapy delivery circuit operably coupled to the plurality of electrodes to deliver cardiac therapy to the patient's heart, and a sensing circuit operably coupled to the plurality of electrodes to sense electrical activity of the patient's heart and the motion detector to sense mechanical activity of the patient's heart. The device also includes a controller having processing circuitry operably coupled to the therapy delivery circuit and the sensing circuit. The controller is configured to detect electrical activity indicating ventricular activation using the second electrode, detect mechanical activity using the motion detector indicating ventricular contraction, determine at least one electromechanical interval based on the detected ventricular activation and the detected ventricular contraction, and determine whether repeated measurements of the at least one electromechanical interval indicate ventricular remodeling.

In another aspect, the present disclosure provides a method that includes delivering a pacing pulse to a patient's heart according to an atrioventricular (AV) pacing interval. The method also includes determining at least one electromechanical interval based on at least one of electrical activity and mechanical activity detected in response to delivering the pacing pulse. The method also includes adjusting the AV pacing interval based on the at least one electromechanical interval.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
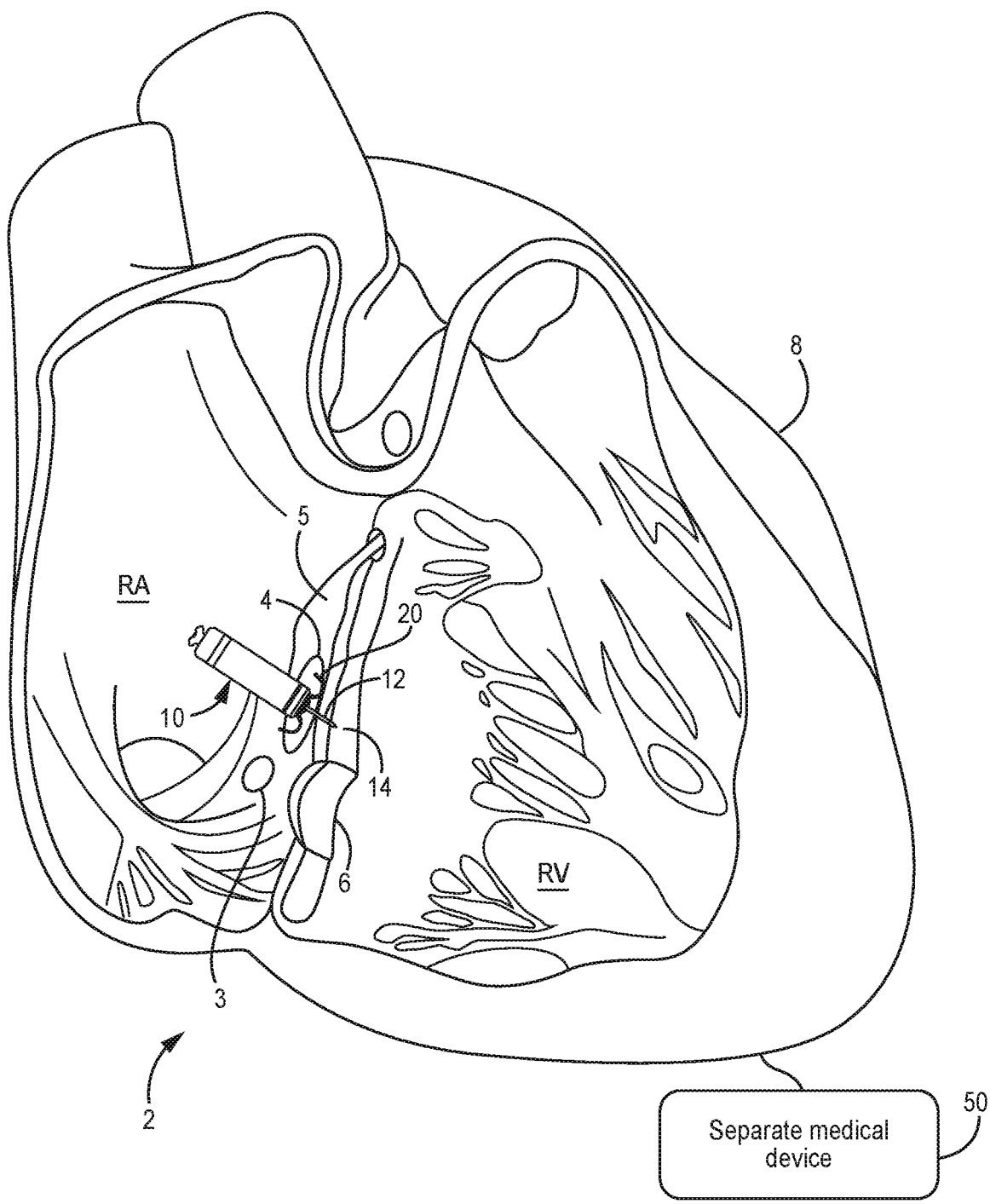
FIG. 1 is a conceptual diagram of an illustrative cardiac therapy system including an intracardiac medical device implanted in a patient's heart and a separate medical device positioned outside of the patient's heart.

The techniques of this disclosure relate to optimizing cardiac therapy, such as cardiac resynchronization therapy (CRT), based on the electrical or mechanical activity of the patient's heart. The electrical and/or mechanical activity may be used to determine whether effective cardiac therapy is being delivered or effective remodeling of the patient's heart is indicated over time. These techniques may include using implantable medical devices to provide cardiac therapy using the cardiac conduction system or left ventricular myocardium implantable, for example, through the right atrium to the left ventricle (e.g., ventricle-from-atrium, or VfA) or through the coronary sinus. In some embodiments, various techniques described herein may be applied to His bundle or bundle branch pacing applications. Various non-limiting examples of cardiac therapy include single chamber or multiple chamber pacing (e.g., dual or triple chamber pacing), atrioventricular synchronous pacing, asynchronous pacing, triggered pacing, cardiac resynchronization pacing, or tachycardia-related therapy. Although reference is made herein to implantable medical devices, such as a pacemaker or ICD, the methods and processes may be used with any medical devices, systems, or methods related to a patient's heart. Various other applications will become apparent to one of skill in the art having the benefit of the present disclosure.

It may be beneficial to provide an implantable medical device and techniques that may be used to optimize cardiac therapy based on electrical and/or mechanical activity. It may be beneficial to provide an implantable medical device that is free of transvenous leads (e.g., a leadless device). It may also be beneficial to provide an implantable medical device capable of being used for various cardiac therapies, such as single or multiple chamber pacing (e.g., dual- or triple-chamber pacing), atrioventricular synchronous pacing, asynchronous pacing, triggered pacing, cardiac resynchronization pacing, or tachycardia-related therapy. Further, it may be beneficial to provide a technique for delivering a medical device to the triangle of Koch region in the right atrium or to the cardiac conduction system in an accurate and precise manner to facilitate pacing the endocardium and/or the His bundle conduction system.

The present disclosure provides a technique for implanting a tissue-piercing electrode in the basal region, septal region, or basal-septal region adjacent to or within the left ventricular myocardium of the patient's heart. In particular, the tissue-piercing electrode may be positioned to sense or pace the cardiac conduction system or left ventricular myocardium and be implantable, for example, through the right atrium to the left ventricle or through the coronary sinus. The tissue-piercing electrode, or another imageable member, may be at least partially formed of an imageable material. The technique may include using an imaging device to capture two-dimensional (2D) imaging data and three-dimensional (3D) information (e.g., orientation information) may be generated from the 2D imaging data that represents the implantable medical device.

In some embodiments, the tissue-piercing electrode may be implanted in the basal region, septal region, or basal-septal region of the left ventricular myocardium of the patient's heart from the triangle of Koch region of the right atrium through the right-atrial endocardium and central fibrous body. In a leadless implantable medical device, the tissue-piercing electrode may leadlessly extend from a distal end region of a housing of the device, and the right-atrial electrode may be leadlessly coupled to the housing (e.g., part of or positioned on the exterior of the housing). The right-atrial motion detector may be within the implantable medical device. In a leaded implantable medical device, one or more of the electrodes may be coupled to the housing using an implantable lead. When the device is implanted, the electrodes may be used to sense electrical activity in one or more atria and/or ventricles of a patient's heart. The motion detector may be used to sense mechanical activity in one or more atria and/or ventricles of the patient's heart. In particular, the activity of the right atrium and the left ventricle may be monitored and, optionally, the activity of the right ventricle may be monitored. The electrodes may be used to deliver cardiac therapy, such as single-chamber pacing for atrial fibrillation, atrioventricular synchronous pacing for bradycardia, asynchronous pacing, triggered pacing, cardiac resynchronization pacing for ventricular dyssynchrony, anti-tachycardia pacing, or shock therapy. Shock therapy may be initiated by the implantable medical device. A separate medical device, such as an extravascular ICD, which may also be implanted, may be in operative communication with the implantable medical device and may deliver an electrical shock in response to a trigger, such as a signaling pulse (e.g., triggering, signaling, or distinctive electrical pulse) provided by the device.

In general, electrical or mechanical activity may be sensed, determined, acquired, or monitored using various techniques available to one having ordinary skill in the art who has the benefit of the present disclosure. As used herein, the term "monitoring" generally refers to sensing, acquiring, or receiving data or information that may be used, for example, being processed or stored.

The present disclosure also provides a technique to deliver and implant a medical device, for example, in the triangle of Koch region in the right atrium. Various devices may be used to identify the general location of the triangle of Koch region, which may be described as an implantation site. A flexible lead, or another probe, may be advanced to the potential implantation site and used to identify a precise location for implantation of a medical device, such as an electrode, leadlet, lead, or intracardiac device. In particular, the techniques of the present disclosure may be used to implant a device to provide synchronous pacing to patients with dyssynchrony, as well as provide dual chamber pacing for bradycardia patients with moderate heart failure.

FIGS. 1-4 show examples of various cardiac therapy systems that may be implanted using, for example, the methods shown in FIGS. 24-25 to deliver a medical device to an implantation site. In these views, the left ventricle (LV) is positioned generally behind the right ventricle (RV).

Although the present disclosure describes leadless and leaded implantable medical devices, reference is first made to FIG. 1, which shows a conceptual diagram of a cardiac therapy system 2 including an intracardiac medical device 10 that may be configured for single or dual chamber therapy and implanted in a patient's heart 8. In some embodiments, the device 10 may be configured for single-chamber pacing and may, for example, switch between single-chamber and multiple-chamber pacing (e.g., dual- or triple-chamber pacing). As used herein, "intracardiac" refers to a device configured to be implanted entirely within a patient's heart, for example, to provide cardiac therapy. The device 10 is shown implanted in the right atrium (RA) of the patient's heart 8 in a target implant region 4. The device 10 may include one or more fixation members 20 that anchor a distal end of the device against the atrial endocardium in a target implant region 4. The target implant region 4 may lie between the His bundle 5 (or bundle of His) and the coronary sinus 3 and may be adjacent the tricuspid valve 6. The device 10 may be described as a ventricle-from-atrium (VfA) device, which may sense or provide therapy to one or both ventricles (e.g., right ventricle, left ventricle, or both ventricles, depending on the circumstances) while being generally disposed in the right atrium. In particular, the device 10 may include a tissue-piercing electrode that may be implanted in the basal region, septal region, or basal-septal region of the left ventricular myocardium of the patient's heart from the triangle of Koch region of the right atrium through the right-atrial endocardium and central fibrous body.

The device 10 may be described as a leadless implantable medical device. As used herein, "leadless" refers to a device being free of a lead extending out of the patient's heart 8. In other words, a leadless device may have a lead that does not extend from outside of the patient's heart to the inside of the patient's heart. Some leadless devices may be introduced through a vein, but once implanted, the device is free of, or may not include, any transvenous lead and may be configured to provide cardiac therapy without using any transvenous lead. Further, a leadless VfA device, in particular, does not use a lead to operably connect to an electrode in the ventricle when a housing of the device is positioned in the atrium. Additionally, a leadless electrode may be coupled to the housing of the medical device without using a lead between the electrode and the housing.

The device 10 may include a dart electrode assembly 12 defining, or having, a straight shaft extending from the distal end region of device 10. The dart electrode assembly 12 may be placed, or at least configured to be placed, through the atrial myocardium and the central fibrous body and into the ventricular myocardium 14, or along the ventricular septum, without perforating entirely through the ventricular endocardial or epicardial surfaces. The dart electrode assembly 12 may carry, or include, an electrode at the distal end region of the shaft such that the electrode may be positioned within the ventricular myocardium for sensing ventricular signals and delivering ventricular pulses (e.g., to depolarize the left ventricle to initiate a contraction of the left ventricle). In some examples, the electrode at the distal end region of the shaft is a cathode electrode provided for use in a bipolar electrode pair for pacing and sensing. While the implant region 4 as illustrated may enable one or more electrodes of the dart electrode assembly 12 to be positioned in the ventricular myocardium, it is recognized that a device having the aspects disclosed herein may be implanted at other locations for multiple chamber pacing (e.g., dual- or triple-chamber pacing), single-chamber pacing with multiple chamber sensing, single-chamber pacing and/or sensing, or other clinical therapy and applications as appropriate.

It is to be understood that although device 10 is described herein as including a single dart electrode assembly, the device 10 may include more than one dart electrode assembly placed, or configured to be placed, through the atrial myocardium and the central fibrous body, and into the ventricular myocardium 14, or along the ventricular septum, without perforating entirely through the ventricular endocardial or epicardial surfaces. Additionally, each dart electrode assembly may carry, or include, more than a single electrode at the distal end region, or along other regions (e.g., proximal or central regions), of the shaft.

The cardiac therapy system 2 may also include a separate medical device 50 (depicted diagrammatically in FIG. 1), which may be positioned outside the patient's heart 8 (e.g., subcutaneously) and may be operably coupled to the patient's heart 8 to deliver cardiac therapy thereto. In one example, separate medical device 50 may be an extravascular ICD. In some embodiments, an extravascular ICD may include a defibrillation lead including, or carrying, a defibrillation electrode. A therapy vector may exist between the defibrillation electrode on the defibrillation lead and a housing electrode of the ICD. Further, one or more electrodes of the ICD may also be used for sensing electrical signals related to the patient's heart 8. The ICD may be configured to deliver shock therapy including one or more defibrillation or cardioversion shocks. For example, if an arrhythmia is sensed, the ICD may send a pulse via the electrical lead wires to shock the heart and restore its normal rhythm. In some examples, the ICD may deliver shock therapy without placing electrical lead wires within the heart or attaching electrical wires directly to the heart (subcutaneous ICDs). Examples of extravascular, subcutaneous ICDs that may be used with the system 2 described herein may be described in U.S. Pat. No. 9,278,229 (Reinke et al.), issued 8 Mar. 2016, which is incorporated herein by reference in its entirety.

In the case of shock therapy (e.g., defibrillation shocks provided by the defibrillation electrode of the defibrillation lead), the separate medical device 50 (e.g., extravascular ICD) may include a control circuit that uses a therapy delivery circuit to generate defibrillation shocks having any of a number of waveform properties, including leading-edge voltage, tilt, delivered energy, pulse phases, and the like. The therapy delivery circuit may, for instance, generate monophasic, biphasic, or multiphasic waveforms. Additionally, the therapy delivery circuit may generate defibrillation waveforms having different amounts of energy. For example, the therapy delivery circuit may generate defibrillation waveforms that deliver a total of between approximately 60-80 Joules (J) of energy for subcutaneous defibrillation.

The separate medical device 50 may further include a sensing circuit. The sensing circuit may be configured to obtain electrical signals sensed via one or more combinations of electrodes and to process the obtained signals. The components of the sensing circuit may include analog components, digital components, or a combination thereof. The sensing circuit may, for example, include one or more sense amplifiers, filters, rectifiers, threshold detectors, analog-to-digital converters (ADCs), or the like. The sensing circuit may convert the sensed signals to digital form and provide the digital signals to the control circuit for processing and/or analysis. For example, the sensing circuit may amplify signals from sensing electrodes and may convert the amplified signals to multi-bit digital signals by an ADC, and then provide the digital signals to the control circuit. In one or more embodiments, the sensing circuit may also compare processed signals to a threshold to detect the existence of atrial or ventricular depolarizations (e.g., P- or R-waves) and indicate the existence of the atrial depolarization (e.g., P-waves) or ventricular depolarizations (e.g., R-waves) to the control circuit.

The device 10 and the separate medical device 50 may cooperate to provide cardiac therapy to the patient's heart 8. For example, the device 10 and the separate medical device 50 may be used to detect tachycardia, monitor tachycardia, and/or provide tachycardia-related therapy. For example, the device 10 may communicate with the separate medical device 50 wirelessly to trigger shock therapy using the separate medical device 50. As used herein, "wirelessly" refers to an operative coupling or connection without using a metal conductor between the device 10 and the separate medical device 50. In one example, wireless communication may use a distinctive, signaling, or triggering electrical-pulse provided by the device 10 that conducts through the patient's tissue and is detectable by the separate medical device 50. In another example, wireless communication may use a communication interface (e.g., an antenna) of the device 10 to provide electromagnetic radiation that propagates through patient's tissue and is detectable, for example, using a communication interface (e.g., an antenna) of the separate medical device 50.

Figure 2:
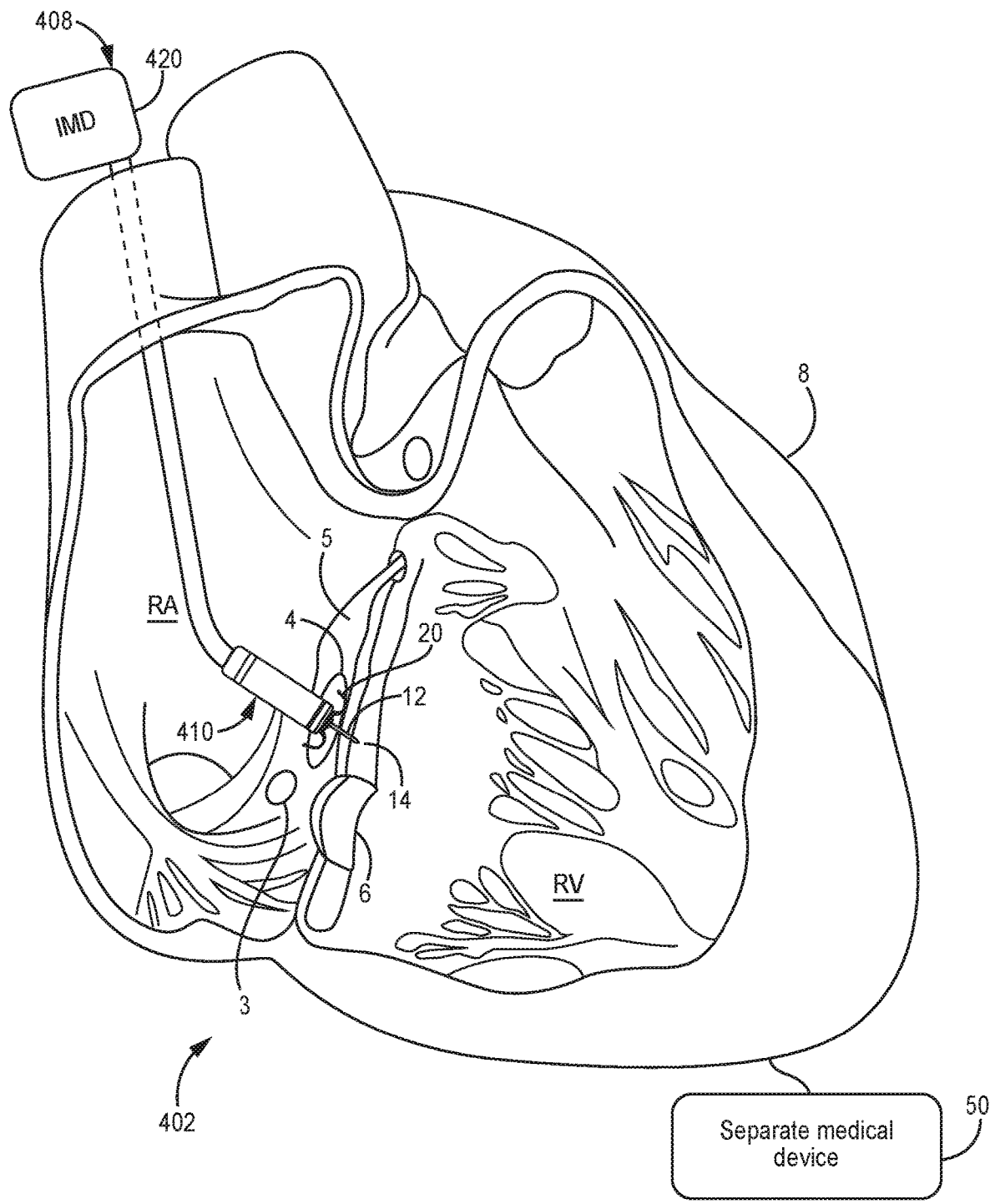
FIGS. 2-4 are conceptual diagrams of illustrative cardiac therapy systems including medical devices including leads with electrodes implanted in a patient's heart.

With reference to FIG. 2, a cardiac therapy system 402 may include a leaded medical device 408 including one, or a single, implantable lead 410 having a tissue-piercing electrode assembly 12 coupled to a distal end region of the lead and implanted inside the patient's heart 8. The housing 420 of the leaded medical device 408 may be implanted and positioned outside of the patient's heart 8 and be configured to calibrate pacing therapy and/or deliver pacing therapy. The lead 410 may include a right-atrial electrode, and the device 408 may operate as a dual-channel capable device (e.g., pacing and/or sensing in both the right atrium and left ventricle). In some embodiments, the lead 410 may not include a right-atrial electrode. In other words, the leaded medical device 408 may be a single channel device, which may be used for asynchronous, triggered, or another type of single-channel pacing. The leaded medical device 408, using the lead 410, may sense activity or deliver pacing to the left ventricle (LV) when the tissue-piercing electrode assembly 12 is implanted, for example, in the same or similar manner as described with respect to FIG. 1.

Figure 3:
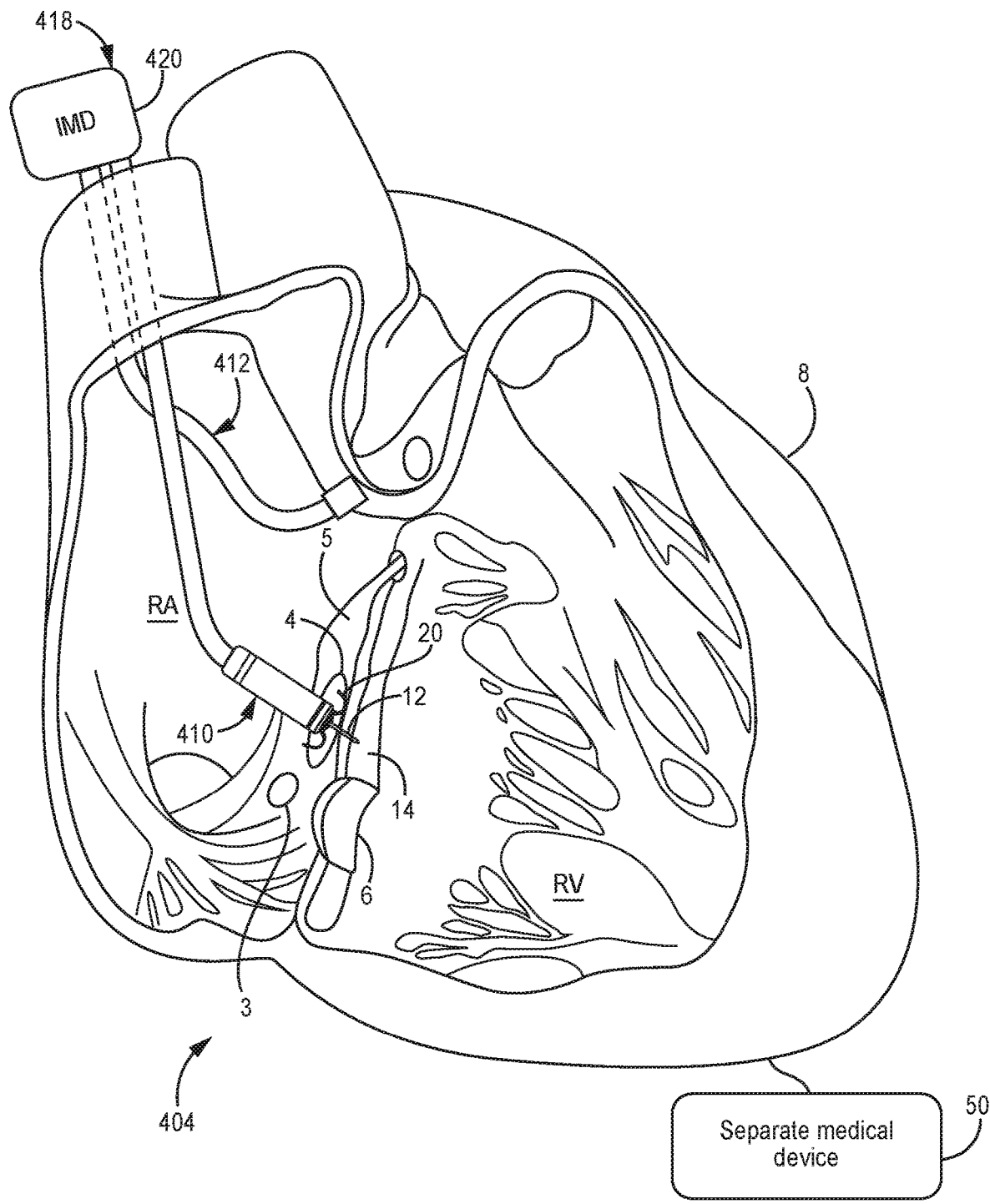

With reference to FIG. 3, a cardiac therapy system 404 may include a leaded medical device 418 similar to the leaded medical device 408 of FIG. 2, except that device 418 includes two implantable leads 410, 412. In particular, implantable lead 412 may include an electrode (e.g., a right-atrial electrode) coupled to a distal end region of the lead 412 and may be implanted in a different location than lead 410. In some embodiments, lead 412 is implanted in a different region of the right atrium. In some embodiments, each lead 410, 412 may contribute one channel of a dual-channel device 418. For example, lead 410 may sense activity or deliver pacing to the left ventricle (LV) when the tissue-piercing electrode of the tissue-piercing electrode assembly 12 is implanted, for example, in the same or similar manner as described with respect to FIG. 1, and lead 412 may sense activity or deliver pacing to the right atrium (RA).

Figure 4:
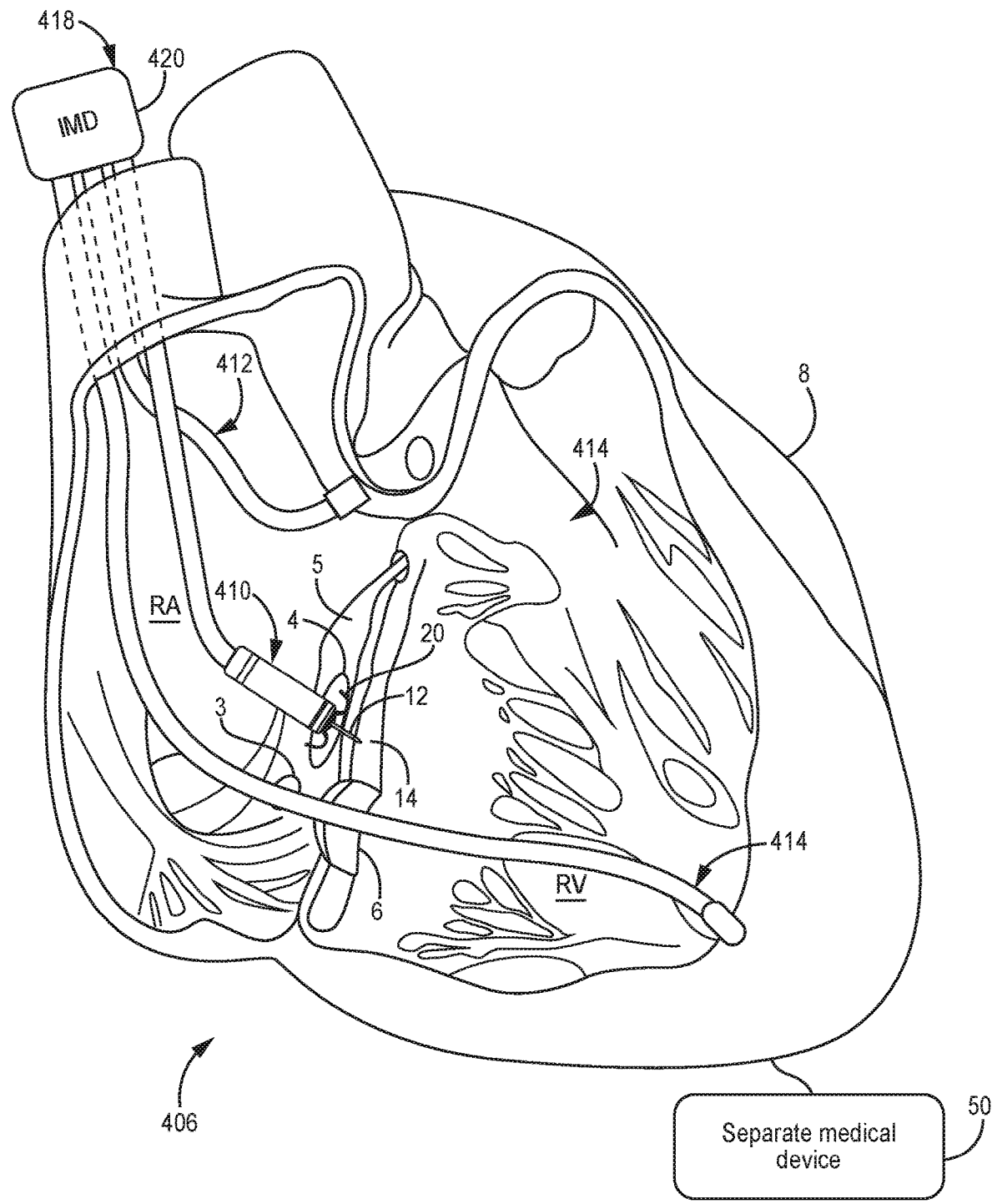

With reference to FIG. 4, a cardiac therapy system 406 may include a leaded medical device 428 similar to the leaded medical device 418 of FIG. 3 except that device 428 includes three implantable leads 410, 412, 414. In particular, implantable lead 414 may include an electrode (e.g., a right ventricular electrode) coupled to a distal end region of the lead 414 and may be implanted in a different location than leads 410, 412. As illustrated, implantable lead 414 extends from the right atrium (RA) to the right ventricle (RV) through tricuspid valve 6. In some embodiments, lead 414 is implanted in a region of the right ventricle. In some embodiments, each lead 410, 412, 414 may contribute one channel to a multi-channel device 428. For example, lead 410 may sense activity or deliver pacing to the left ventricle (LV) when the tissue-piercing electrode assembly 12 is implanted, for example, in the same or similar manner as described with respect to FIG. 1, lead 412 may sense activity from the delivery of pacing to the RA, and lead 414 may sense activity or deliver pacing to the RV.

In some embodiments, a pacing delay between the RV electrode on lead 414 to pace the RV and the LV electrode on lead 410 to pace the LV (e.g., RV-LV pacing delay, or more generally, VV pacing delay) may be calibrated or optimized, for example, using a separate medical device, such as an electrode apparatus (e.g., ECG belt). Various methods may be used to calibrate or optimize the VV delay. In some embodiments, the medical device 428 may be used to test pacing at a plurality of different VV delays. For example, the RV may be paced ahead of the LV by about 80, 60, 40, and 20 milliseconds (ms) and the LV may be paced ahead of the RV by about 80, 60, 40, and 20 ms, as well as simultaneous RV-LV pacing (e.g., about 0 ms VV pacing delay). The medical device 428 may then be configured, for example, automatically, to select a VV pacing delay that, when used for pacing, corresponds to a minimal electrical dyssynchrony measured using the electrode apparatus. The test pacing at different VV pacing delays may be performed using a particular AV delay, such as a nominal AV delay set by the medical device 428 or at a predetermined optimal AV delay based on patient characteristics.

Figure 5:
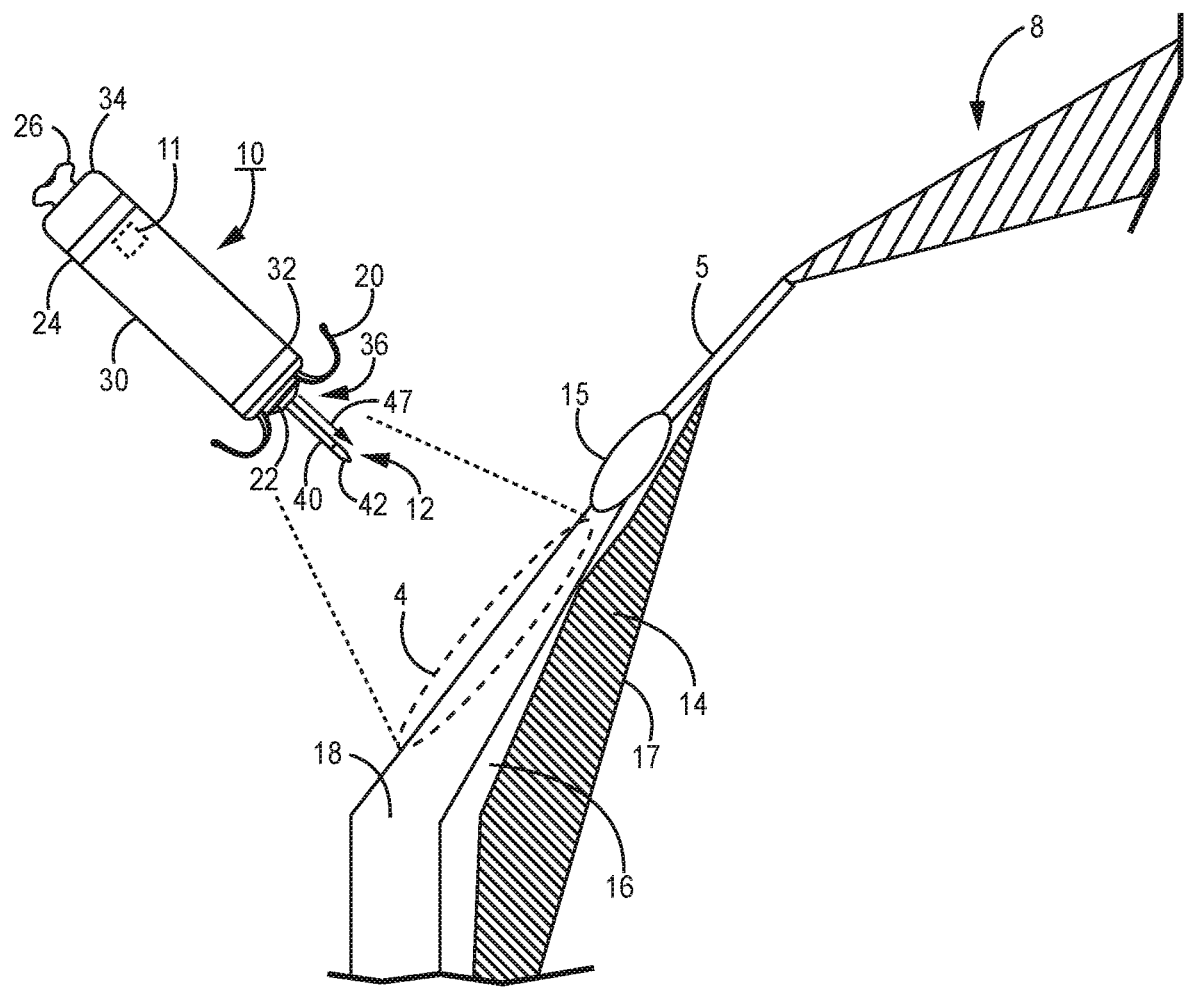
FIG. 5 is an enlarged conceptual diagram of the intracardiac medical device of FIG. 1 and anatomical structures of the patient's heart.

FIG. 5 is an enlarged conceptual diagram of the intracardiac medical device 10 of FIG. 1 and anatomical structures of the patient's heart 8. In particular, the device 10 is configured to sense electrical activity and/or deliver pacing therapy. The intracardiac device 10 may include a housing 30. The housing 30 may define a hermetically-sealed internal cavity in which internal components of the device 10 reside, such as a sensing circuit, therapy delivery circuit, control circuit, memory, telemetry circuit, other optional sensors, and a power source as generally described in conjunction with FIG. 8. The housing 30 may be formed from an electrically conductive material including titanium or titanium alloy, stainless steel, MP35N (a non-magnetic nickel-cobalt-chromium-molybdenum alloy), platinum alloy, or other bio-compatible metal or metal alloy. In other examples, the housing 30 may be formed from a non-conductive material including ceramic, glass, sapphire, silicone, polyurethane, epoxy, acetyl co-polymer plastics, polyether ether ketone (PEEK), a liquid crystal polymer, or other biocompatible polymer.

In at least one embodiment, the housing 30 may be described as extending between a distal end region 32 and a proximal end region 34 in a generally cylindrical shape to facilitate catheter delivery. In other embodiments, the housing 30 may be prismatic or any other shape to perform the functionality and utility described herein. The housing 30 may include a delivery tool interface member 26, e.g., at the proximal end region 34, for engaging with a delivery tool during implantation of the device 10.

All or a portion of the housing 30 may function as an electrode during cardiac therapy, for example, in sensing and/or pacing. In the example shown, the housing-based electrode 24 is shown to circumscribe a proximal portion (e.g., closer to the proximal end region 34 than the distal end region 32) of the housing 30. When the housing 30 is formed from an electrically conductive material, such as a titanium alloy or other examples listed above, portions of the housing 30 may be electrically insulated by a non-conductive material, such as a coating of parylene, polyurethane, silicone, epoxy, or other biocompatible polymer, leaving one or more discrete areas of conductive material exposed to define the proximal housing-based electrode 24. When the housing 30 is formed from a non-conductive material, such as a ceramic, glass or polymer material, an electrically conductive coating or layer, such as a titanium, platinum, stainless steel, or alloys thereof, may be applied to one or more discrete areas of the housing 30 to form the proximal housing-based electrode 24. In other examples, the proximal housing-based electrode 24 may be a component, such as a ring electrode, that is mounted or assembled onto the housing 30. The proximal housing-based electrode 24 may be electrically coupled to internal circuitry of the device 10, e.g., via the electrically-conductive housing 30 or an electrical conductor when the housing 30 is a non-conductive material.

In the example shown, the proximal housing-based electrode 24 is located nearer to the housing proximal end region 34 than the housing distal end region 32 and is therefore referred to as a "proximal housing-based electrode" 24. In other examples, however, the housing-based electrode 24 may be located at other positions along the housing 30, e.g., more distal relative to the position shown.

At the distal end region 32, the device 10 may include a distal fixation and electrode assembly 36, which may include one or more fixation members 20 and one or more dart electrode assemblies 12 of equal or unequal length. In one example, a single dart electrode assembly 12 includes a shaft 40 extending distally away from the housing distal end region 32 and one or more electrode elements, such as a tip electrode 42 at or near the free, distal end region of the shaft 40. The tip electrode 42 may have a conical or hemispherical distal tip with a relatively narrow tip-diameter (e.g., less than about 1 millimeter (mm)) for penetrating into and through tissue layers without using a sharpened tip or needle-like tip having sharpened or beveled edges.

The shaft 40 of the dart electrode assembly 12 may be a normally straight member and may be rigid. In other embodiments, the shaft 40 may be described as being relatively stiff but still possessing limited flexibility in lateral directions. Further, the shaft 40 may be non-rigid to allow some lateral flexing with heart motion. However, in a relaxed state, when not subjected to any external forces, the shaft 40 may maintain a straight position as shown to hold the tip electrode 42 spaced apart from the housing distal end region 32 at least by the height 47 of the shaft 40. In other words, the dart electrode assembly 12 may be described as resilient.

The dart electrode assembly 12 may be configured to pierce through one or more tissue layers to position the tip electrode 42 within a desired tissue layer, e.g., the ventricular myocardium. As such, the height 47, or length, of the shaft 40 may correspond to the expected pacing site depth, and the shaft 40 may have a relatively high compressive strength along its longitudinal axis to resist bending in a lateral or radial direction when pressed against the implant region 4. If a second dart electrode assembly 12 is employed, its length may be unequal to the expected pacing site depth and may be configured to act as an indifferent electrode for delivering of pacing energy to the tissue. A longitudinal axial force may be applied against the tip electrode 42, e.g., by applying a longitudinal pushing force to the proximal end region 34 of the housing 30, to advance the dart electrode assembly 12 into the tissue within the target implant region. The shaft 40 may be described as longitudinally non-compressive and/or elastically deformable in lateral or radial directions when subjected to lateral or radial forces to allow temporary flexing, e.g., with tissue motion, but may return to its normally straight position when lateral forces diminish. When the shaft 40 is not exposed to any external force, or to only a force along its longitudinal central axis, the shaft 40 may retain a straight, linear position as shown.

The one or more fixation members 20 may be described as one or more "tines" having a normally curved position. The tines may be held in a distally extended position within a delivery tool. The distal tips of tines may penetrate the heart tissue to a limited depth before elastically curving back proximally into the normally curved position (shown) upon release from the delivery tool. Further, the fixation members 20 may include one or more aspects described in, for example, U.S. Pat. No. 9,675,579 (Grubac et al.), issued 13 Jun. 2017, and U.S. Pat. No. 9,119,959 (Rys et al.), issued 1 Sep. 2015, each of which is incorporated herein by reference in its entirety.

In some examples, the distal fixation and electrode assembly 36 includes a distal housing-based electrode 22. In the case of using the device 10 as a pacemaker for multiple chamber pacing (e.g., dual- or triple-chamber pacing) and sensing, the tip electrode 42 may be used as a cathode electrode paired with the proximal housing-based electrode 24 serving as a return anode electrode. Alternatively, the distal housing-based electrode 22 may serve as a return anode electrode paired with tip electrode 42 for sensing ventricular signals and delivering ventricular pacing pulses. In other examples, the distal housing-based electrode 22 may be a cathode electrode for sensing atrial signals and delivering pacing pulses to the atrial myocardium in the target implant region 4. When the distal housing-based electrode 22 serves as an atrial cathode electrode, the proximal housing-based electrode 24 may serve as the return anode paired with the tip electrode 42 for ventricular pacing and sensing and as the return anode paired with the distal housing-based electrode 22 for atrial pacing and sensing.

As shown in this illustration, the target implant region 4 in some pacing applications is along the atrial endocardium 18, generally inferior to the AV node 15 and the His bundle 5. The dart electrode assembly 12 may at least partially define the height 47, or length, of the shaft 40 for penetrating through the atrial endocardium 18 in the target implant region 4, through the central fibrous body 16, and into the ventricular myocardium 14 without perforating through the ventricular endocardial surface 17. When the height 47, or length, of the dart electrode assembly 12 is fully advanced into the target implant region 4, the tip electrode 42 may rest within the ventricular myocardium 14, and the distal housing-based electrode 22 may be positioned in intimate contact with or close proximity to the atrial endocardium 18. The dart electrode assembly 12 may have a total combined height 47, or length, of the tip electrode 42 and the shaft 40 from about 3 mm to about 8 mm in various examples. The diameter of the shaft 40 may be less than about 2 mm, and may be about 1 mm or less, or even about 0.6 mm or less.

Figure 8:
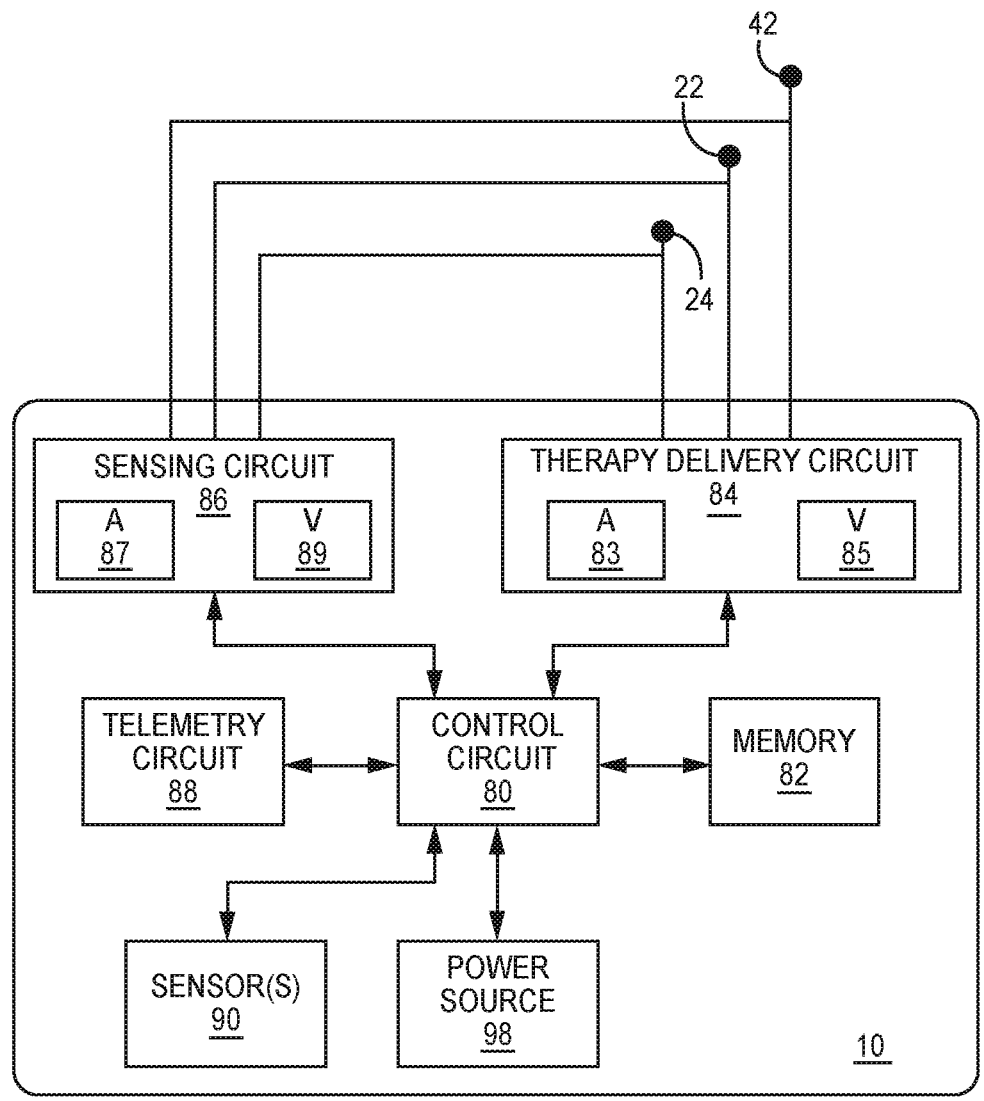
FIG. 8 is a block diagram of illustrative circuitry that may be enclosed within the housing of the medical devices of FIGS. 1-4 and 16, for example, to provide the functionality and therapy described herein.
Figure 10:
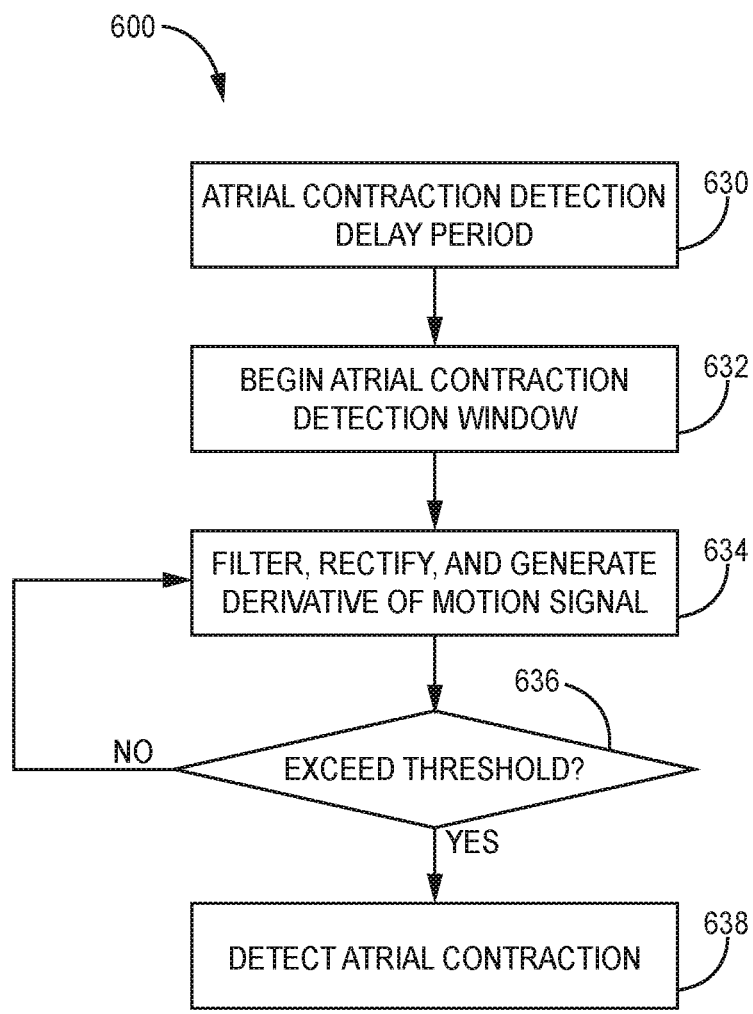
FIG. 10 is a flowchart of an illustrative method of detecting atrial activity using an atrial motion detector for use with, e.g., the illustrative systems and devices of FIGS. 1-4 and 16.
Figure 11:
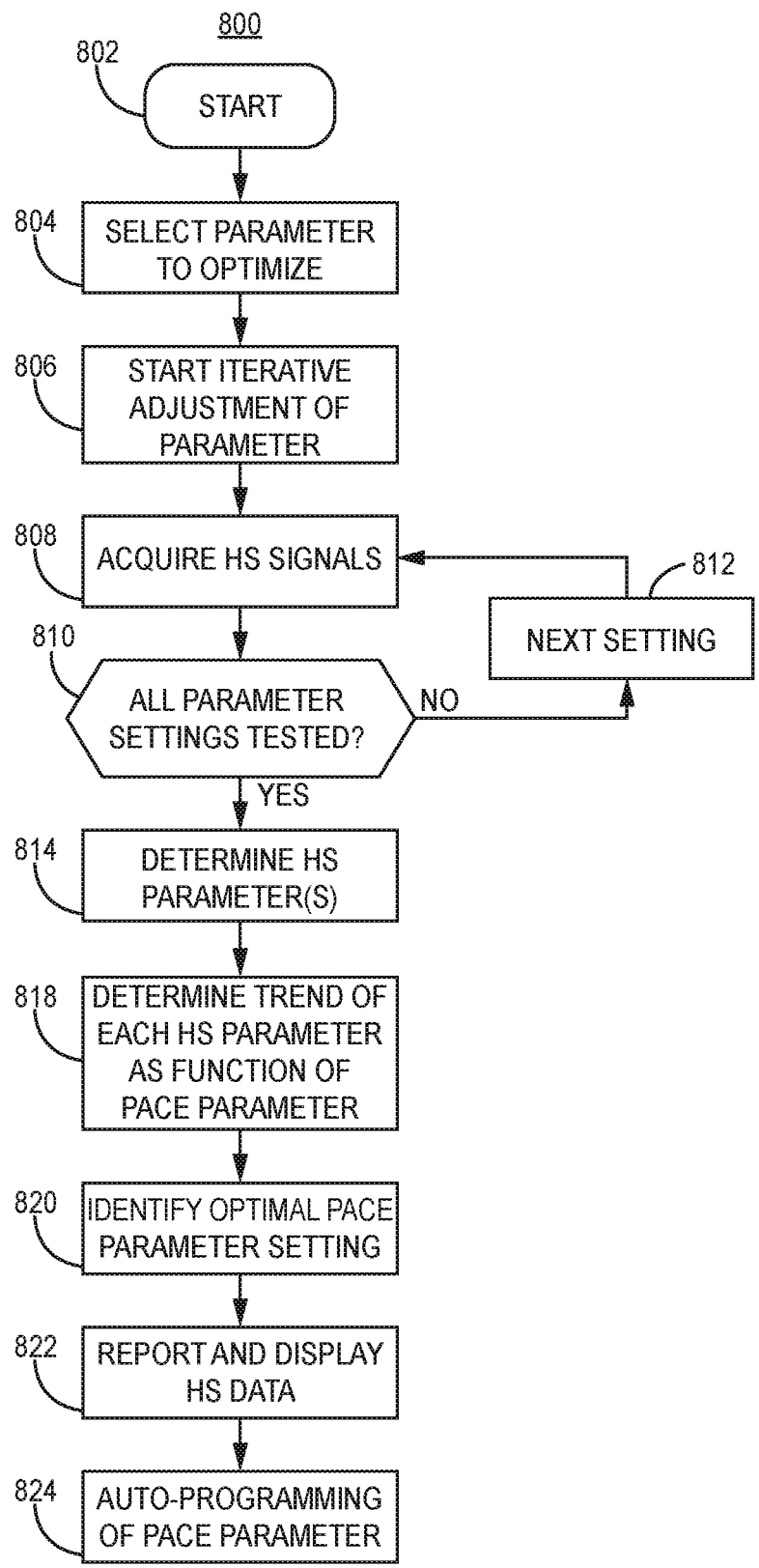
FIG. 11 is a flowchart of an illustrative method of detecting heart sounds to represent physiological response information for use with, e.g., the illustrative systems and devices of FIGS. 1-4 and 16.
Figure 12:
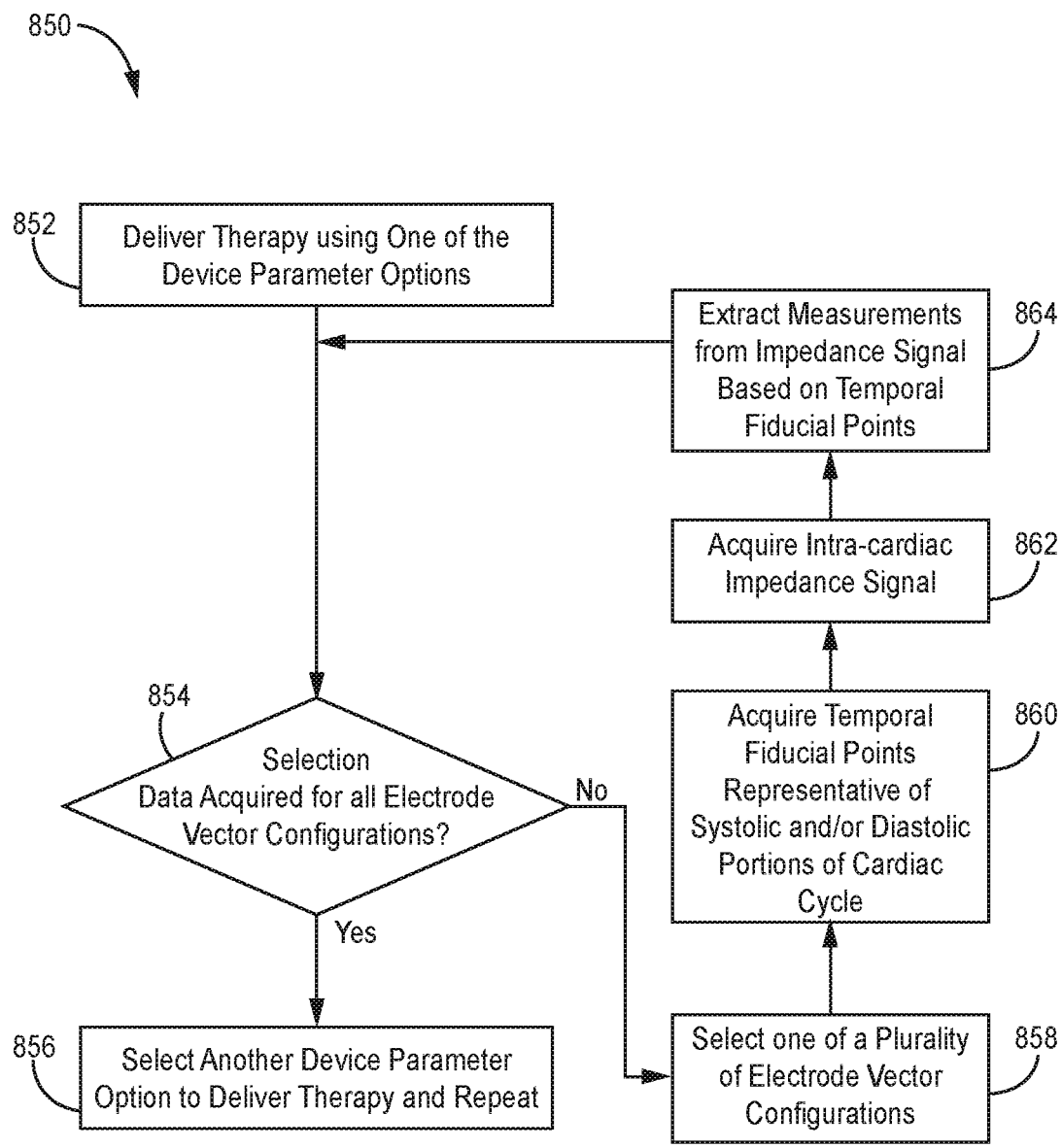
FIG. 12 is a flowchart of an illustrative method of detecting bioimpedance to represent physiological response information for use with, e.g., the illustrative systems and devices of FIGS. 1-4 and 16.

The device 10 may include an acoustic or motion detector 11 within the housing 30. The acoustic or motion detector 11 may be operably coupled to one or more a control circuit 80 (FIG. 8), a sensing circuit 86 (FIG. 8), or therapy delivery circuit 84 (FIG. 8). In some embodiments, the acoustic or motion detector 11 may be used with methods 600, 650, or 800 as shown in FIGS. 10-12. The acoustic or motion detector 11 may be used to monitor mechanical activity, such as atrial mechanical activity (e.g., an atrial contraction) and/or ventricular mechanical activity (e.g., a ventricular contraction). In some embodiments, the acoustic or motion detector 11 may be used to detect right-atrial mechanical activity. A non-limiting example of an acoustic or motion detector 11 includes an accelerometer or microphone. In some embodiments, the mechanical activity detected by the acoustic or motion detector 11 may be used to supplement or replace electrical activity detected by one or more of the electrodes of the device 10. For example, the acoustic or motion detector 11 may be used in addition to, or as an alternative to, the proximal housing-based electrode 24.

The acoustic or motion detector 11 may also be used for rate response detection or to provide a rate-responsive IMD. Various techniques related to rate response may be described in U.S. Pat. No. 5,154,170 (Bennett et al.), issued Oct. 13, 1992, entitled "Optimization for rate responsive cardiac pacemaker," and U.S. Pat. No. 5,562,711 (Yerich et al.), issued Oct. 8, 1996, entitled "Method and apparatus for rate-responsive cardiac pacing," each of which is incorporated herein by reference in its entirety.

In various embodiments, acoustic or motion detector 11 (or motion sensor) may be used as an HS sensor and may be implemented as a microphone or a 1-, 2- or 3-axis accelerometer. In one embodiment, the acoustical sensor is implemented as a piezoelectric crystal mounted within an implantable medical device housing and responsive to the mechanical motion associated with heart sounds. The piezoelectric crystal may be a dedicated HS sensor or may be used for multiple functions. In the illustrative embodiment shown, the acoustical sensor is embodied as a piezoelectric crystal that is also used to generate a patient alert signal in the form of a perceptible vibration of the IMD housing. Upon detecting an alert condition, control circuit 80 may cause patient alert control circuitry to generate an alert signal by activating the piezoelectric crystal.

The control circuit may be used to control whether the piezoelectric crystal is used in a "listening mode" to sense HS signals by HS sensing circuitry or in an "output mode" to generate a patient alert. During patient alert generation, HS sensing circuitry may be temporarily decoupled from the HS sensor by control circuitry.

Examples of other embodiments of acoustical sensors that may be adapted for implementation with the techniques of the present disclosure may be described generally in U.S. Pat. No. 4,546,777 (Groch, et al.), U.S. Pat. No. 6,869,404 (Schulhauser, et al.), U.S. Pat. No. 5,554,177 (Kieval, et al.), and U.S. Pat. No. 7,035,684 (Lee, et al.), each of which is incorporated herein by reference in its entirety.

Various types of acoustical sensors may be used. The acoustical sensor may be any implantable or external sensor responsive to one or more of the heart sounds generated as described in the foregoing and thereby produces an analog electrical signal correlated in time and amplitude to the heart sounds. The analog signal may be then be processed, which may include digital conversion, by the HS sensing module to obtain HS parameters, such as amplitudes or relative time intervals, as derived by HS sensing module or control circuit 80. The acoustical sensor and HS sensing module may be incorporated in an IMD capable of delivering CRT or another cardiac therapy being optimized or may be implemented in a separate device having wired or wireless communication with IMD or an external programmer or computer used during a pace-parameter optimization procedure as described herein.

Figure 6:
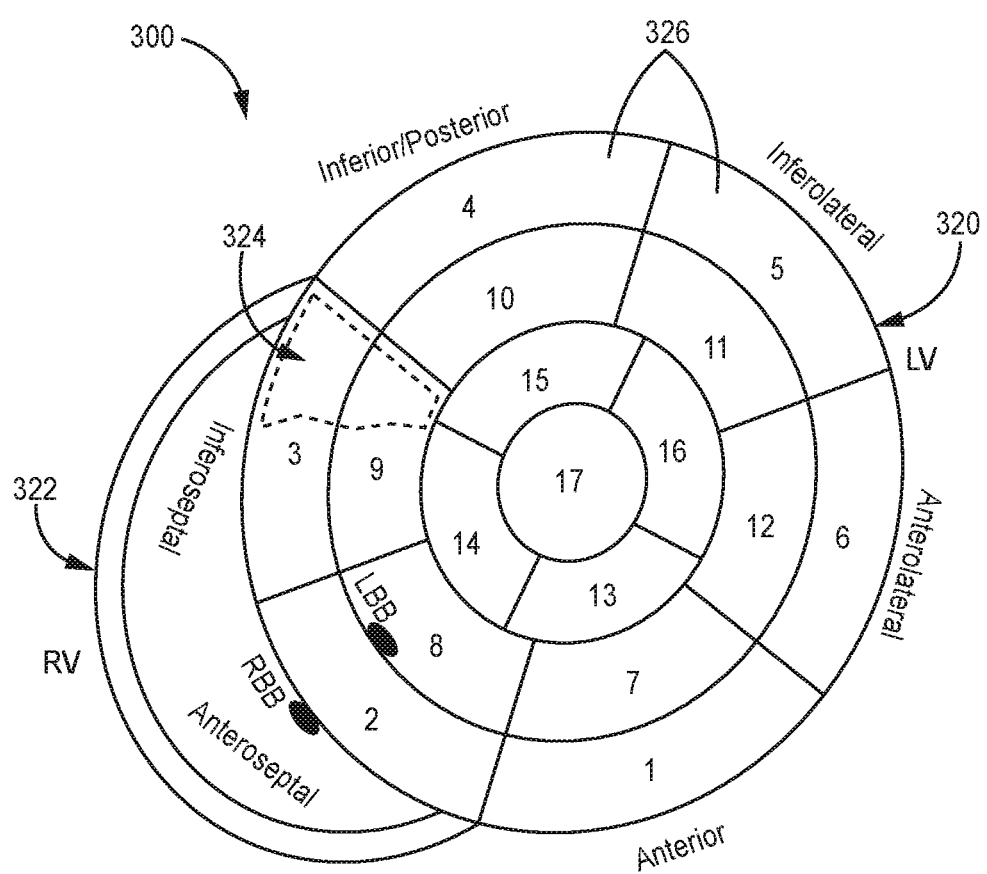
FIG. 6 is a conceptual diagram of a map of a patient's heart in a standard 17 segment view of the left ventricle showing various electrode implantation locations.

FIG. 6 is a two-dimensional (2D) ventricular map 300 of a patient's heart (e.g., a top-down view) showing the left ventricle 320 in a standard 17 segment view and the right ventricle 322. The map 300 includes a plurality of areas 326 corresponding to different regions of a human heart. As illustrated, the areas 326 are numerically labeled 1-17 (e.g., which correspond to 17 segments of the left ventricle of a human heart). Areas 326 of the map 300 may include basal anterior area 1, basal anteroseptal area 2, basal inferoseptal area 3, basal inferior area 4, basal inferolateral area 5, basal anterolateral area 6, mid-anterior area 7, mid-anteroseptal area 8, mid-inferoseptal area 9, mid-inferior area 10, mid-inferolateral area 11, mid-anterolateral area 12, apical anterior area 13, apical septal area 14, apical inferior area 15, apical lateral area 16, and apex area 17. The inferoseptal and anteroseptal areas of the right ventricle 322 are also illustrated, as well as the right bundle branch (RBB) and left bundle branch (LBB).

In some embodiments, any of the tissue-piercing electrodes of the present disclosure may be implanted in the basal region, septal region, or basal-septal region of the left ventricular myocardium of the patient's heart. In particular, the tissue-piercing electrode may be implanted from the triangle of Koch region of the right atrium through the right-atrial endocardium and central fibrous body.

Once implanted, the tissue-piercing electrode may be positioned in the target implant region 4 (FIGS. 1-5), such as the basal region, septal region, or basal-septal region of the left ventricular myocardium. With reference to map 300, the basal region includes one or more of the basal anterior area 1, basal anteroseptal area 2, basal inferoseptal area 3, basal inferior area 4, mid-anterior area 7, mid-anteroseptal area 8, mid-inferoseptal area 9, and mid-inferior area 10. With reference to map 300, the septal region includes one or more of the basal anteroseptal area 2, basal anteroseptal area 3, mid-anteroseptal area 8, mid-inferoseptal area 9, and apical septal area 14.

In some embodiments, the tissue-piercing electrode may be positioned in the basal septal region of the left ventricular myocardium when implanted. The basal septal region may include one or more of the basal anteroseptal area 2, basal inferoseptal area 3, mid-anteroseptal area 8, and mid-inferoseptal area 9.

In some embodiments, the tissue-piercing electrode may be positioned in the high inferior/posterior basal septal region of the left ventricular myocardium when implanted. The high inferior/posterior basal septal region of the left ventricular myocardium may include a portion of one or more of the basal inferoseptal area 3 and mid-inferoseptal area 9 (e.g., the basal inferoseptal area only, the mid-inferoseptal area only, or both the basal inferoseptal area and the mid-inferoseptal area). For example, the high inferior/posterior basal septal region may include region 324 illustrated generally as a dashed-line boundary. As shown, the dashed line boundary represents an approximation of where the high inferior/posterior basal septal region is located, which may take a somewhat different shape or size depending on the particular application.

Figure 7:
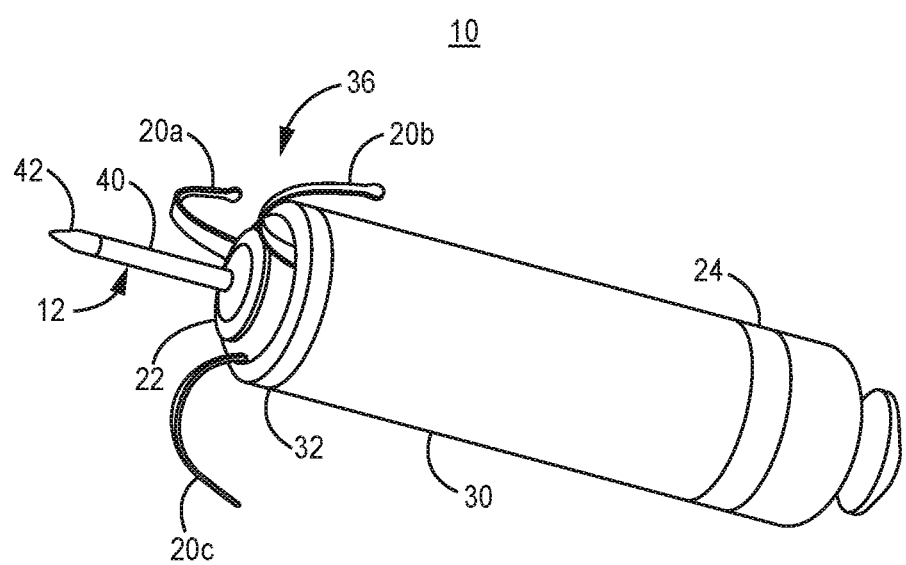
FIG. 7 is a perspective view of an intracardiac medical device having a distal fixation and electrode assembly that includes a distal housing-based electrode implemented as a ring electrode for use with, e.g., the illustrative systems and devices of FIGS. 1-4 and 16.

FIG. 7 is a three-dimensional perspective view of the device 10 capable of calibrating pacing therapy and/or delivering pacing therapy. As shown, the distal fixation and electrode assembly 36 includes the distal housing-based electrode 22 implemented as a ring electrode. The distal housing-based electrode 22 may be positioned in intimate contact with or operative proximity to atrial tissue when fixation member tines 20a, 20b, and 20c of the fixation members 20, engage with the atrial tissue. The tines 20a, 20b, and 20c, which may be elastically deformable, may be extended distally during delivery of device 10 to the implant site. For example, the tines 20a, 20b, and 20c may pierce the atrial endocardial surface as the device 10 is advanced out of the delivery tool and flex back into their normally curved position (as shown) when no longer constrained within the delivery tool. As the tines 20a, 20b, and 20c curve back into their normal position, the fixation member 20 may pull the distal fixation member and electrode assembly 36 toward the atrial endocardial surface. As the distal fixation member and electrode assembly 36 is pulled toward the atrial endocardium, the tip electrode 42 may be advanced through the atrial myocardium and the central fibrous body and into the ventricular myocardium. The distal housing-based electrode 22 may then be positioned against the atrial endocardial surface.

The distal housing-based electrode 22 may include a ring formed of an electrically conductive material, such as titanium, platinum, iridium, or alloys thereof. The distal housing-based electrode 22 may be a single, continuous ring electrode. In other examples, portions of the ring may be coated with an electrically insulating coating, e.g., parylene, polyurethane, silicone, epoxy, or another insulating coating, to reduce the electrically conductive surface area of the ring electrode. For instance, one or more sectors of the ring may be coated to separate two or more electrically conductive exposed surface areas of the distal housing-based electrode 22. Reducing the electrically conductive surface area of the distal housing-based electrode 22, e.g., by covering portions of the electrically conductive ring with an insulating coating, may increase the electrical impedance of the distal housing-based electrode 22, and thereby, reduce the current delivered during a pacing pulse that captures the myocardium, e.g., the atrial myocardial tissue. A lower current drain may conserve the power source, e.g., one or more rechargeable or non-rechargeable batteries, of the device 10.

As described above, the distal housing-based electrode 22 may be configured as an atrial cathode electrode for delivering pacing pulses to the atrial tissue at the implant site in combination with the proximal housing-based electrode 24 as the return anode. The electrodes 22 and 24 may be used to sense atrial P-waves for use in controlling atrial pacing pulses (delivered in the absence of a sensed P-wave) and for controlling atrial-synchronized ventricular pacing pulses delivered using the tip electrode 42 as a cathode and the proximal housing-based electrode 24 as the return anode. In other examples, the distal housing-based electrode 22 may be used as a return anode in conjunction with the cathode tip electrode 42 for ventricular pacing and sensing.

Figure 9:
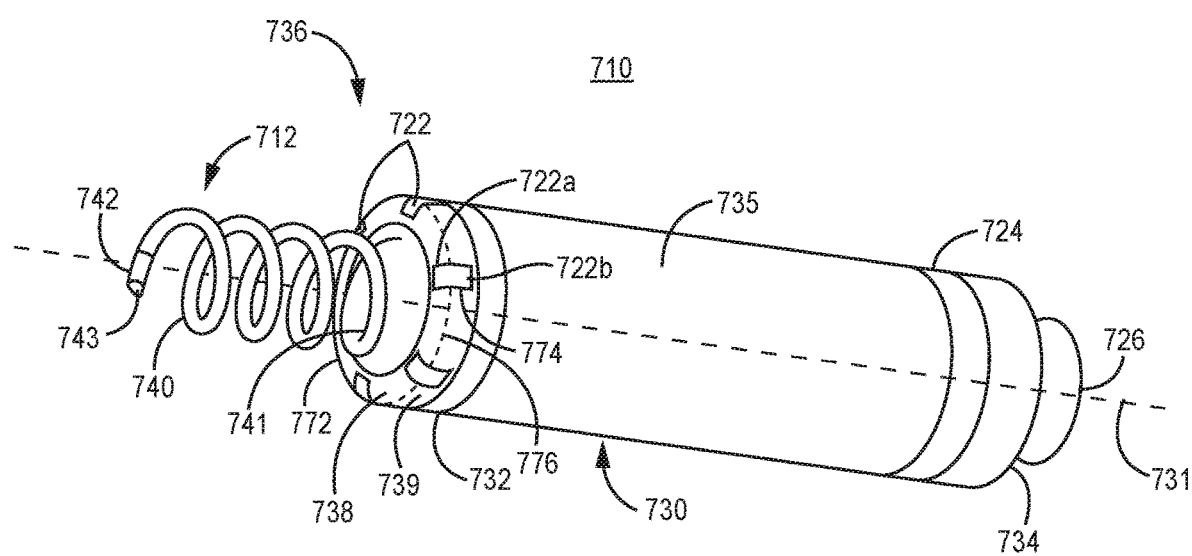
FIG. 9 is a perspective view of another illustrative intracardiac medical device for use with, e.g., the illustrative systems and devices of FIGS. 1-4 and 16.

FIG. 8 is a block diagram of circuitry that may be enclosed within the housing 30 (FIG. 7) to provide the functions of calibrating pacing therapy and/or delivering pacing therapy, using the device 10 according to one example or within the housings of any other medical devices described herein (e.g., device 408 of FIG. 2, device 418 of FIG. 3, device 428 of FIG. 4, or device 710 of FIG. 9). The separate medical device 50 (FIGS. 1-4) may include some or all the same components, which may be configured in a similar manner. The electronic circuitry enclosed within housing 30 may include software, firmware, and hardware that cooperatively monitor atrial and ventricular electrical cardiac signals, determine when a cardiac therapy is necessary, and/or deliver electrical pulses to the patient's heart according to programmed therapy mode and pulse control parameters. The electronic circuitry may include a control circuit 80 (e.g., including processing circuitry), a memory 82, a therapy delivery circuit 84, a sensing circuit 86, and/or a telemetry circuit 88. In some examples, the device 10 includes one or more sensors 90 for producing a signal that is correlated to a physiological function, state, or condition of the patient, such as a patient activity sensor, for use in determining a need for pacing therapy and/or controlling a pacing rate. For example, one sensor 90 may include an inertial measurement unit (e.g., accelerometer) to measure motion.

The power source 98 may provide power to the circuitry of the device 10 including each of the components 80, 82, 84, 86, 88, 90 as needed. The power source 98 may include one or more energy storage devices, such as one or more rechargeable or non-rechargeable batteries. The connections (not shown) between the power source 98 and each of the components, such as sensors 80, 82, 84, 86, 88, 90, may be understood from the general block diagram illustrated to one of ordinary skill in the art. For example, the power source 98 may be coupled to one or more charging circuits included in the therapy delivery circuit 84 for providing the power used to charge holding capacitors included in the therapy delivery circuit 84 that are discharged at appropriate times under the control of the control circuit 80 for delivering pacing pulses, e.g., according to a dual chamber pacing mode such as DDI(R). The power source 98 may also be coupled to components of the sensing circuit 86, such as sense amplifiers, analog-to-digital converters, switching circuitry, etc., sensors 90, the telemetry circuit 88, and the memory 82 to provide power to the various circuits.

The functional blocks shown represent functionality included in the device 10 and may include any discrete and/or integrated electronic circuit components that implement analog, and/or digital circuits capable of producing the functions attributed to the medical device 10 herein. The various components may include processing circuitry, such as an application specific integrated circuit (ASIC), an electronic circuit, a processor (shared, dedicated, or group), and memory that execute one or more software or firmware programs, a combinational logic circuit, state machine, or other suitable components or combinations of components that provide the described functionality. The particular form of software, hardware, and/or firmware employed to implement the functionality disclosed herein will be determined primarily by the particular system architecture employed in the medical device and by the particular detection and therapy delivery methodologies employed by the medical device.

The memory 82 may include any volatile, non-volatile, magnetic, or electrical non-transitory computer-readable storage media, such as random-access memory (RAM), read-only memory (ROM), non-volatile RAM (NVRAM), electrically-erasable programmable ROM (EEPROM), flash memory, or any other memory device. Furthermore, the memory 82 may include a non-transitory computer-readable media storing instructions that, when executed by one or more processing circuits, cause the control circuit 80 and/or other processing circuitry to calibrate pacing therapy and/or perform a single, dual, or triple-chamber calibrated pacing therapy (e.g., single or multiple chamber pacing), or other cardiac therapy functions (e.g., sensing or delivering therapy), attributed to the device 10. The non-transitory computer-readable media storing the instructions may include any of the media listed above.

The control circuit 80 may communicate, e.g., via a data bus, with the therapy delivery circuit 84 and the sensing circuit 86 for sensing cardiac electrical signals and controlling delivery of cardiac electrical stimulation therapies in response to sensed cardiac events, e.g., P-waves and R-waves, or the absence thereof. The tip electrode 42, the distal housing-based electrode 22, and the proximal housing-based electrode 24 may be electrically coupled to the therapy delivery circuit 84 for delivering electrical stimulation pulses to the patient's heart and to the sensing circuit 86 and for sensing cardiac electrical signals.

The sensing circuit 86 may include an atrial (A) sensing channel 87 and a ventricular (V) sensing channel 89. The distal housing-based electrode 22 and the proximal housing-based electrode 24 may be coupled to the atrial sensing channel 87 for sensing atrial signals, e.g., P-waves attendant to the depolarization of the atrial myocardium. In examples that include two or more selectable distal housing-based electrodes, the sensing circuit 86 may include switching circuitry for selectively coupling one or more of the available distal housing-based electrodes to cardiac event detection circuitry included in the atrial sensing channel 87. Switching circuitry may include a switch array, switch matrix, multiplexer, or any other type of switching device suitable to selectively couple components of the sensing circuit 86 to selected electrodes. The tip electrode 42 and the proximal housing-based electrode 24 may be coupled to the ventricular sensing channel 89 for sensing ventricular signals, e.g., R-waves attendant to the depolarization of the ventricular myocardium.

Each of the atrial sensing channel 87 and the ventricular sensing channel 89 may include cardiac event detection circuitry for detecting P-waves and R-waves, respectively, from the cardiac electrical signals received by the respective sensing channels. The cardiac event detection circuitry included in each of the channels 87 and 89 may be configured to amplify, filter, digitize, and rectify the cardiac electrical signal received from the selected electrodes to improve the signal quality for detecting cardiac electrical events. The cardiac event detection circuitry within each channel 87 and 89 may include one or more sense amplifiers, filters, rectifiers, threshold detectors, comparators, analog-to-digital converters (ADCs), timers, or other analog or digital components. A cardiac event sensing threshold, e.g., a P-wave sensing threshold and an R-wave sensing threshold, may be automatically adjusted by each respective sensing channel 87 and 89 under the control of the control circuit 80, e.g., based on timing intervals and sensing threshold values determined by the control circuit 80, stored in the memory 82, and/or controlled by hardware, firmware, and/or software of the control circuit 80 and/or the sensing circuit 86.

Upon detecting a cardiac electrical event based on a sensing threshold crossing, the sensing circuit 86 may produce a sensed event signal that is passed to the control circuit 80. For example, the atrial sensing channel 87 may produce a P-wave sensed event signal in response to a P-wave sensing threshold crossing. The ventricular sensing channel 89 may produce an R-wave sensed event signal in response to an R-wave sensing threshold crossing. The sensed event signals may be used by the control circuit 80 for setting pacing escape interval timers that control the basic time intervals used for scheduling cardiac pacing pulses. A sensed event signal may trigger or inhibit a pacing pulse depending on the particular programmed pacing mode. For example, a P-wave sensed event signal received from the atrial sensing channel 87 may cause the control circuit 80 to inhibit a scheduled atrial pacing pulse and schedule a ventricular pacing pulse at a programmed atrioventricular (AV) pacing interval. If an R-wave is sensed before the AV pacing interval expires, the ventricular pacing pulse may be inhibited. If the AV pacing interval expires before the control circuit 80 receives an R-wave sensed event signal from the ventricular sensing channel 89, the control circuit 80 may use the therapy delivery circuit 84 to deliver the scheduled ventricular pacing pulse synchronized to the sensed P-wave.

In some examples, the device 10 may be configured to deliver a variety of pacing therapies including bradycardia pacing, cardiac resynchronization therapy, post-shock pacing, and/or tachycardia-related therapy, such as ATP, among others. For example, the device 10 may be configured to detect non-sinus tachycardia and deliver ATP. The control circuit 80 may determine cardiac event time intervals, e.g., P-P intervals between consecutive P-wave sensed event signals received from the atrial sensing channel 87, R-R intervals between consecutive R-wave sensed event signals received from the ventricular sensing channel 89, and P-R and/or R-P intervals received between P-wave sensed event signals and R-wave sensed event signals. These intervals may be compared to tachycardia detection intervals for detecting non-sinus tachycardia. Tachycardia may be detected in a given heart chamber based on a threshold number of tachycardia detection intervals being detected.

The therapy delivery circuit 84 may include atrial pacing circuit 83 and ventricular pacing circuit 85. Each pacing circuit 83, 85 may include charging circuitry, one or more charge storage devices such as one or more low voltage holding capacitors, an output capacitor, and/or switching circuitry that controls when the holding capacitor(s) are charged and discharged across the output capacitor to deliver a pacing pulse to the pacing electrode vector coupled to respective pacing circuits 83, 85. The tip electrode 42 and the proximal housing-based electrode 24 may be coupled to the ventricular pacing circuit 85 as a bipolar cathode and anode pair for delivering ventricular pacing pulses, e.g., upon expiration of an AV or VV pacing interval set by the control circuit 80 for providing atrial-synchronized ventricular pacing and a basic lower ventricular pacing rate.

The atrial pacing circuit 83 may be coupled to the distal housing-based electrode 22 and the proximal housing-based electrode 24 to deliver atrial pacing pulses. The control circuit 80 may set one or more atrial pacing intervals according to a programmed lower pacing rate or a temporary lower rate set according to a rate-responsive sensor-indicated pacing rate. Atrial pacing circuit may be controlled to deliver an atrial pacing pulse if the atrial pacing interval expires before a P-wave sensed event signal is received from the atrial sensing channel 87. The control circuit 80 starts an AV pacing interval in response to a delivered atrial pacing pulse to provide synchronized multiple chamber pacing (e.g., dual- or triple-chamber pacing).

Charging of a holding capacitor of the atrial or ventricular pacing circuit 83, 85 to a programmed pacing voltage amplitude and discharging of the capacitor for a programmed pacing pulse width may be performed by the therapy delivery circuit 84 according to control signals received from the control circuit 80. For example, a pace timing circuit included in the control circuit 80 may include programmable digital counters set by a microprocessor of the control circuit 80 for controlling the basic pacing time intervals associated with various single-chamber or multiple-chamber pacing (e.g., dual- or triple-chamber pacing) modes or anti-tachycardia pacing sequences. The microprocessor of the control circuit 80 may also set the amplitude, pulse width, polarity, or other characteristics of the cardiac pacing pulses, which may be based on programmed values stored in the memory 82.

The device 10 may include other sensors 90 for sensing signals from the patient for use in determining a need for and/or controlling electrical stimulation therapies delivered by the therapy delivery circuit 84. In some examples, a sensor indicative of a need for increased cardiac output may include a patient activity sensor, such as an accelerometer.

An increase in the metabolic demand of the patient due to increased activity as indicated by the patient activity sensor may be determined by the control circuit 80 for use in determining a sensor-indicated pacing rate.

Control parameters utilized by the control circuit 80 for sensing cardiac events and controlling pacing therapy delivery may be programmed into the memory 82 via the telemetry circuit 88, which may also be described as a communication interface. The telemetry circuit 88 includes a transceiver and antenna for communicating with an external device, such as a programmer or home monitor, using radio frequency communication or other communication protocols. The control circuit 80 may use the telemetry circuit 88 to receive downlink telemetry from and send uplink telemetry to the external device. In some cases, the telemetry circuit 88 may be used to transmit and receive communication signals to/from another medical device implanted in the patient.

FIG. 9 is a three-dimensional perspective view of another leadless intracardiac medical device 710 that may be configured for calibrating pacing therapy and/or delivering pacing therapy for single or multiple chamber cardiac therapy (e.g., dual- or triple-chamber cardiac therapy) according to another example. The device 710 may include a housing 730 having an outer sidewall 735, shown as a cylindrical outer sidewall, extending from a housing distal end region 732 to a housing proximal end region 734. The housing 730 may enclose electronic circuitry configured to perform single- or multiple-chamber cardiac therapy, including atrial and ventricular cardiac electrical signal sensing and pacing the atrial and ventricular chambers. The delivery tool interface member 726 is shown on the housing proximal end region 734.

A distal fixation and electrode assembly 736 may be coupled to the housing distal end region 732. The distal fixation and electrode assembly 736 may include an electrically insulative distal member 772 coupled to the housing distal end region 732. The tissue-piercing electrode assembly 712 extends away from the housing distal end region 732, and multiple non-tissue piercing electrodes 722 may be coupled directly to the insulative distal member 772. The tissue-piercing electrode assembly 712 extends in a longitudinal direction away from the housing distal end region 732 and may be coaxial with the longitudinal center axis 731 of the housing 730.

The distal tissue-piercing electrode assembly 712 may include an electrically insulated shaft 740 and a tip electrode 742 (e.g., tissue-piercing electrode). In some examples, the tissue-piercing electrode assembly 712 is an active fixation member including a helical shaft 740 and a distal cathode tip electrode 742. The helical shaft 740 may extend from a shaft distal end region 743 to a shaft proximal end region 741, which may be directly coupled to the insulative distal member 772. The helical shaft 740 may be coated with an electrically insulating material, e.g., parylene or other examples listed herein, to avoid sensing or stimulation of cardiac tissue along the shaft length. The tip electrode 742 is at the shaft distal end region 743 and may serve as a cathode electrode for delivering ventricular pacing pulses and sensing ventricular electrical signals using the proximal housing-based electrode 724 as a return anode when the tip electrode 742 is advanced into ventricular tissue. The proximal housing-based electrode 724 may be a ring electrode circumscribing the housing 730 and may be defined by an uninsulated portion of the longitudinal sidewall 735. Other portions of the housing 730 not serving as an electrode may be coated with an electrically insulating material as described above in conjunction with FIG. 7.

Using two or more tissue-piercing electrodes (e.g., of any type) penetrating into the LV myocardium may be used for more localized pacing capture and may mitigate ventricular pacing spikes affecting capturing atrial tissue. In some embodiments, multiple tissue-piercing electrodes may include two or more dart-type electrode assemblies (e.g., electrode assembly 12 of FIG. 7), a helical-type electrode (e.g., electrode assembly 712) Non-limiting examples of multiple tissue-piercing electrodes include two dart electrode assemblies, a helix electrode with a dart electrode assembly extending therethrough (e.g., through the center), or dual intertwined helixes. Multiple tissue-piercing electrodes may also be used for bipolar or multi-polar pacing.

In some embodiments, one or more tissue-piercing electrodes (e.g., of any type) that penetrate into the LV myocardium may be a multi-polar tissue-piercing electrode. A multi-polar tissue-piercing electrode may include one or more electrically active and electrically separate elements, which may enable bipolar or multi-polar pacing from one or more tissue-piercing electrodes.

Multiple non-tissue piercing electrodes 722 may be provided along a periphery of the insulative distal member 772, peripheral to the tissue-piercing electrode assembly 712. The insulative distal member 772 may define a distal-facing surface 738 of the device 710 and a circumferential surface 739 that circumscribes the device 710 adjacent to the housing longitudinal sidewall 735. Non-tissue piercing electrodes 722 may be formed of an electrically conductive material, such as titanium, platinum, iridium, or alloys thereof. In the illustrated embodiment, six non-tissue piercing electrodes 722 are spaced apart radially at equal distances along the outer periphery of insulative distal member 772. However, two or more non-tissue piercing electrodes 722 may be provided.

Non-tissue piercing electrodes 722 may be discrete components each retained within a respective recess 774 in the insulative member 772 sized and shaped to mate with the non-tissue piercing electrode 722. In other examples, the non-tissue piercing electrodes 722 may each be an uninsulated, exposed portion of a unitary member mounted within or on the insulative distal member 772. Intervening portions of the unitary member not functioning as an electrode may be insulated by the insulative distal member 772 or, if exposed to the surrounding environment, may be coated with an electrically insulating coating, e.g., parylene, polyurethane, silicone, epoxy, or another insulating coating.

When the tissue-piercing electrode assembly 712 is advanced into cardiac tissue, at least one non-tissue piercing electrode 722 may be positioned against, in intimate contact with, or in operative proximity to, a cardiac tissue surface for delivering pulses and/or sensing cardiac electrical signals produced by the patient's heart. For example, non-tissue piercing electrodes 722 may be positioned in contact with right-atrial endocardial tissue for pacing and sensing in the atrium when the tissue-piercing electrode assembly 712 is advanced into the atrial tissue and through the central fibrous body until the distal tip electrode 742 is positioned in direct contact with ventricular tissue, e.g., ventricular myocardium and/or a portion of the ventricular conduction system.

Non-tissue piercing electrodes 722 may be coupled to the therapy delivery circuit 84 and the sensing circuit 86 (see FIG. 8) enclosed by the housing 730 to function collectively as a cathode electrode for delivering atrial pacing pulses and for sensing atrial electrical signals, e.g., P-waves, in combination with the proximal housing-based electrode 724 as a return anode. Switching circuitry included in the sensing circuit 86 may be activated under the control of the control circuit 80 to couple one or more of the non-tissue piercing electrodes to the atrial sensing channel 87. Distal, non-tissue piercing electrodes 722 may be electrically isolated from each other so that each individual one of the electrodes 722 may be individually selected by switching circuitry included in the therapy delivery circuit 84 to serve alone or in a combination of two or more of the electrodes 722 as an atrial cathode electrode. Switching circuitry included in the therapy delivery circuit 84 may be activated under the control of the control circuit 80 to couple one or more of the non-tissue piercing electrodes 722 to the atrial pacing circuit 83. Two or more of the non-tissue piercing electrodes 722 may be selected at a time to operate as a multi-point atrial cathode electrode.

Certain non-tissue piercing electrodes 722 selected for atrial pacing and/or atrial sensing may be selected based on atrial capture threshold tests, electrode impedance, P-wave signal strength in the cardiac electrical signal, or other factors. For example, a single one or any combination of two or more individual non-tissue piercing electrodes 722 functioning as a cathode electrode that provides an optimal combination of a low pacing capture threshold amplitude and relatively high electrode impedance may be selected to achieve reliable atrial pacing using minimal current drain from the power source 98.

In some instances, the distal-facing surface 738 may uniformly contact the atrial endocardial surface when the tissue-piercing electrode assembly 712 anchors the housing 730 at the implant site. In that case, all the electrodes 722 may be selected together to form the atrial cathode. Alternatively, every other one of the electrodes 722 may be selected together to form a multi-point atrial cathode having a higher electrical impedance that is still uniformly distributed along the distal-facing surface 738. Alternatively, a subset of one or more electrodes 722 along one side of the insulative distal member 772 may be selected to provide pacing at a desired site that achieves the lowest pacing capture threshold due to the relative location of the electrodes 722 to the atrial tissue being paced.

In other instances, the distal-facing surface 738 may be oriented at an angle relative to the adjacent endocardial surface depending on the positioning and orientation at which the tissue-piercing electrode assembly 712 enters the cardiac tissue. In this situation, one or more of the non-tissue piercing electrodes 722 may be positioned in contact with the adjacent endocardial tissue closer than other non-tissue piercing electrodes 722, which may be angled away from the endocardial surface. By providing multiple non-tissue piercing electrodes along the periphery of the insulative distal member 772, the angle of the tissue-piercing electrode assembly 712 and the housing distal end region 732 relative to the cardiac surface, e.g., the right-atrial endocardial surface, may not be required to be substantially parallel. Anatomical and positional differences may cause the distal-facing surface 738 to be angled or oblique to the endocardial surface, however, multiple non-tissue piercing electrodes 722 distributed along the periphery of the insulative distal member 772 increase the likelihood of good contact between one or more electrodes 722 and the adjacent cardiac tissue to promote acceptable pacing thresholds and reliable cardiac event sensing using at least a subset of multiple electrodes 722. Contact or fixation circumferentially along the entire periphery of the insulative distal member 772 may not be required.

The non-tissue piercing electrodes 722 are shown to each include a first portion 722a extending along the distal-facing surface 738 and a second portion 722b extending along the circumferential surface 739. The first portion 722a and the second portion 722b may be continuous, exposed surfaces such that the active electrode surface wraps around a peripheral edge 776 of the insulative distal member 772 that joins the distal facing surface 738 and the circumferential surface 739. The non-tissue piercing electrodes 722 may include one or more of the electrodes 722 along the distal-facing surface 738, one or more electrodes along the circumferential surface 739, one or more electrodes each extending along both of the distal-facing surface 738 and the circumferential surface 739, or any combination thereof. The exposed surface of each of the non-tissue piercing electrodes 722 may be flush with respective distal-facing surfaces 738 and/or circumferential surfaces. In other examples, each of the non-tissue piercing electrodes 722 may have a raised surface that protrudes from the insulative distal member 772. Any raised surface of the electrodes 722, however, may define a smooth or rounded, non-tissue piercing surface.

The distal fixation and electrode assembly 736 may seal the distal end region of the housing 730 and may provide a foundation on which the electrodes 722 are mounted. The electrodes 722 may be referred to as housing-based electrodes. The electrodes 722 may not be carried by a shaft or other extension that extends the active electrode portion away from the housing 730, like the distal tip electrode 742 residing at the distal tip of the helical shaft 740 extending away from the housing 730. Other examples of non-tissue piercing electrodes presented herein that are coupled to a distal-facing surface and/or a circumferential surface of an insulative distal member include the distal housing-based ring electrode 22 (FIG. 7), the distal housing-based ring electrode extending circumferentially around the assembly 36 (FIG. 7), button electrodes, other housing-based electrodes, and other circumferential ring electrodes. Any non-tissue piercing electrodes directly coupled to a distal insulative member, peripherally to a central tissue-piercing electrode, may be provided to function individually, collectively, or in any combination as a cathode electrode for delivering pacing pulses to adjacent cardiac tissue. When a ring electrode, such as the distal ring electrode 22 and/or a circumferential ring electrode, is provided, portions of the ring electrode may be electrically insulated by a coating to provide multiple distributed non-tissue piercing electrodes along the distal-facing surface and/or the circumferential surface of the insulative distal member.

The non-tissue piercing electrodes 722 and other examples listed above are expected to provide more reliable and effective atrial pacing and sensing than a tissue-piercing electrode provided along the distal fixation and electrode assembly 736. The atrial chamber walls are relatively thin compared to ventricular chamber walls. A tissue-piercing atrial cathode electrode may extend too deep within the atrial tissue leading to inadvertent sustained or intermittent capture of ventricular tissue. A tissue-piercing atrial cathode electrode may lead to interference with sensing atrial signals due to ventricular signals having a larger signal strength in the cardiac electrical signal received via tissue-piercing atrial cathode electrodes that are closer in physical proximity to the ventricular tissue. The tissue-piercing electrode assembly 712 may be securely anchored into ventricular tissue for stabilizing the implant position of the device 710 and providing reasonable certainty that the tip electrode 742 is sensing and pacing in ventricular tissue while the non-tissue piercing electrodes 722 are reliably pacing and sensing in the atrium. When the device 710 is implanted in the target implant region 4, e.g., as shown in FIG. 1 the ventricular septum, the tip electrode 742 may reach left ventricular tissue for pacing of the left ventricle while the non-tissue piercing electrodes 722 provide pacing and sensing in the right atrium. The tissue-piercing electrode assembly 712 may be in the range of about 4 to about 8 mm in length from the distal-facing surface 738 to reach left ventricular tissue. In some instances, the device 710 may achieve four-chamber pacing by delivering atrial pacing pulses from the atrial pacing circuit 83 via the non-tissue piercing electrodes 722 in the target implant region 4 to achieve bi-atrial (right and left atrial) capture and by delivering ventricular pacing pulses from the ventricular pacing circuit 85 via the tip electrode 742 advanced into ventricular tissue from the target implant region 4 to achieve biventricular (right and left ventricular) capture.

FIG. 10 shows an illustrative method 600 of detecting atrial activity, for example, using the acoustic or motion detector 11 of FIG. 5, which may be used to represent physiological response information. In particular, method 600 may include detecting an atrial contraction based on analysis of a motion signal (e.g., provided by the motion detector 11) that may be performed by an IMD implanted in the patient's heart. In some embodiments, the motion signal may be provided by an IMD implanted within a ventricle, such as the right ventricle, of the patient's heart. The method 600 may include beginning an atrial contraction detection delay period upon identification of a ventricular activation event 630. The method 600 may include beginning an atrial contraction detection window upon expiration of the atrial contraction delay period 632. The method 600 may include analyzing the motion signal within the atrial contraction detection window.

The method 600 may include filtering the motion signal within the atrial contraction detection window, rectifying the filtered signal, and generating a derivative signal of the filtered and rectified motion signal 634 within the atrial contraction detection window. The method 600 may include determining whether an amplitude of the derivative signal within the atrial contraction detection window exceeds a threshold 636. In response to determining that the amplitude of the derivative signal within the atrial contraction detection window exceeds the threshold (YES of 636), the method 600 may proceed to detecting atrial contraction 638. Otherwise (NO of 636), the method 600 may return to filtering, rectifying, and generating a derivative signal 634. Various techniques for using a motion detector that provides a motion signal may be described in U.S. Pat. No. 9,399,140 (Cho et al.), issued Jul. 26, 2016, entitled "Atrial contraction detection by a ventricular leadless pacing device for atriosynchronous ventricular pacing," which is incorporated herein by reference in its entirety.

As will be described with respect to FIG. 11, heart sounds (HS) may be detected and used to represent physiological response information. As described herein, the amplitudes and/or relative time intervals of one or more of the S1 through S4 heart sounds can be useful in optimizing a patient's hemodynamic response to CRT or other cardiac therapies that include cardiac pacing and/or neural stimulation for achieving hemodynamic benefit. The first heart sound, S1, corresponds to the start of ventricular systole. Ventricular systole begins when an action potential conducts through the atrioventricular node (AV node) and quickly depolarizes the ventricular myocardium. This event is distinguished by the QRS complex on the ECG. As the ventricles contract, the pressure in the ventricles begins to rise, causing abrupt closure of the mitral and tricuspid valves between the ventricles and atria as ventricular pressure exceeds atrial pressure. This valve closure may generate S1. S1 generally has a duration of about 150 ms and a frequency on the order of about 20 to 250 Hz. The amplitude of S1 may provide a surrogate measurement of LV contractility. Thus, an increase in S1 amplitude positively may correlate with an improvement in LV contractility. Other measures, like the pre-ejection period measured from the onset of QRS to S1, may also be used as a surrogate of myocardial contractility index.

Separation of the closure of the mitral and tricuspid valves due to ventricular dyssynchrony can be observed as separate M1 and T1 peaks in the S1 signal. Merging of the M1 (mitral valve closure sound) and the T1 (tricuspid valve closure sound) can be used as an indication of improved ventricular synchrony.

Generally, left ventricular pressure (LVP) rises dramatically following the QRS complex of the ECG and closure of the mitral valve and continues to build during ventricular systole until the aortic and pulmonary valves open, ejecting blood into the aorta and pulmonary artery. Ventricular contraction typically continues to cause blood pressure to rise in the ventricles and the aorta and pulmonary artery during the ejection phase. As the contraction diminishes, blood pressure decreases until the aortic and pulmonary valves close.

The second heart sound, S2, may be generated by the closure of the aortic and pulmonary valves, near the end of ventricular systole and start of ventricular diastole. S2 may, therefore, be correlated to diastolic pressure in the aorta and the pulmonary artery. S2 generally has a duration of about 120 ms and a frequency on the order of 25 to 350 Hz. The time interval between S1 and S2, i.e., S1-S2 time interval may represent the systolic time interval (STI) corresponding to the ventricular isovolumic contraction (pre-ejection) and ejection phase of the cardiac cycle. This S1-S2 time interval may provide a surrogate measurement for stroke volume. Furthermore, the ratio of the pre-ejection period (Q-S1) to S1-S2 time may be used as an index of myocardial contractility.

The third heart sound, S3, is associated with early, passive diastolic filling of the ventricles, and the fourth heart sound, S4, may be associated with late, active filling of the ventricles due to atrial contraction. The third sound is generally difficult to hear in a normal patient using a stethoscope, and the fourth sound is generally not heard in a normal patient. Presence of the third and fourth heart sounds during an examination using a stethoscope may indicate a pathological condition. The S3 and S4 heart sounds may be used in optimizing pace parameters as they relate to the diastolic function of the heart. Generally, these sounds would be minimized or disappear when an optimal pace parameter is identified. Other aspects of the S1 through S4 heart sounds and timing thereof that may be useful in cardiac pace-parameter optimization as known to one having ordinary skill in the art.

FIG. 11 is a flowchart 800 of a method for using heart sounds to optimize pace control parameters according to one embodiment. Methods of the present disclosure may include one or more blocks shown in flowchart 800. Other examples of using heart sounds to optimize cardiac therapy are described generally in U.S. Pat. No. 9,643,0134, granted May 9, 2017, entitled "System and method for pacing parameter optimization using heart sounds," which is incorporated herein by reference in its entirety.

A pace-parameter optimization method may be initiated at block 802. The optimization process may be initiated in response to a user command received via an external programmer. At a time of initial IMD implantation or during office follow-up visits, or during a remote patient monitoring session, a user may initiate an HS-base optimization procedure using an external programmer or networked computer. Additionally, or alternatively, the process shown by flowchart 800 may be an automated process started periodically or in response to sensing a need for therapy delivery or therapy adjustment based on a sensed physiological signal, which may include sensed HS signals.

At block 804 a pace control parameter to be optimized is selected. A control parameter may be a timing-related parameter, such as an AV interval or VV interval. Pacing vector is another control parameter that may be selected at block 804 for optimization. For example, when a multi-polar lead is used, such as a coronary sinus lead, multiple bipolar or unipolar pacing vectors may be selected for pacing in a given heart chamber. The pacing site associated with a particular pacing vector may have a significant effect on the hemodynamic benefit of pacing therapy. As such, pacing vector is one pace control parameter that may be optimized using methods described herein.

A pacing sequence is initiated at block 806 using an initial parameter setting for the test parameter selected at block 804. In one embodiment, the AV interval is being optimized, and ventricular pacing is delivered at an initial AV interval setting. It is understood that an initial AV interval setting may be selected at block 806 by first measuring an intrinsic AV interval in a patient having intact AV conduction, i.e., no AV block. An initial AV interval may be a default pacing interval, the last programmed AV interval, or a minimum or maximum AV interval to be tested. Alternatively, if the VV interval is selected for optimization, an intrinsic inter-ventricular conduction time may be measured first and paced VV intervals may be iteratively adjusted beginning at a VV interval longer, shorter, or approximately equal to the intrinsic VV conduction time.

An iterative process for adjusting the selected test parameter to at least two different settings is performed. The parameter may be adjusted to different settings in any desired order, e.g., increasing, decreasing, random, etc. For example, during adjustment of AV interval, an initial AV interval may be set to just longer than or approximately equal to a measured intrinsic AV conduction time then iteratively decreased down to a minimum AV interval test setting. During pacing using each pace parameter setting, HS signals are acquired at block 808. The iterative process advances to the next test parameter setting at block 812 until all test parameter settings have been applied, as determined at block 810, and HS signals have been recorded for each setting.

HS signals may be acquired for multiple cardiac cycles to enable ensemble averaging or averaging of HS parameter measurements taken from individual cardiac cycles. It is understood that amplification, filtering, rectification, noise cancellation techniques or other signal processing steps may be used for improving the signal-to-noise ratio of the HS signals and these steps may be different for each of the heart sounds being acquired, which may include any or all types of heart sounds.

At least one HS parameter measurement is determined from the recorded HS signals for each test parameter setting at block 814. The IMD processor or an external processor, e.g., included in a programmer, or a combination of both may perform the HS signal analysis described herein. In one embodiment, S1 and S2 are recorded and HS parameters are measured using the S1 and S2 signals at block 814. For example, the amplitude of S1, the V-S2 interval (where the V event may be a V pace or a sensed R-wave), and the S1-S2 interval are measured. The presence of S3 and/or S4 may additionally be noted, or measurements of these signals may be made for determining related parameters. HS signal parameters are determined for at least two different test parameter settings, e.g., at least two different AV intervals, two or more different VV intervals, or two or more different pacing vectors.

At block 818, a trend for each HS parameter determined at block 810 as a function of the pace parameter test settings is determined. In one embodiment, a trend for each of the V-S2 interval, S1 amplitude, and S1-S2 interval is determined. Other embodiments may include determining separation of the M1 and T1 sounds during the S1 signal. Based on the trends of the HS parameter(s) with respect to the varied pace control parameter, an optimal pace parameter setting may be identified automatically by the processor at block 820. Additionally, or alternatively, the HS trends are reported and displayed at block 822 on an external device such as a programmer or at a remote networked computer.

If the pace parameter being tested is, for example, pacing site or pacing vector when a multipolar electrode is positioned along a heart chamber, such as a quadripolar lead along LV, a pacing site or vector may be selected based on maximizing an HS-based surrogate for ventricular contractility. In one embodiment, the amplitude of S1 is used as a surrogate for ventricular contractility, and a pacing site or vector associated with a maximum S1 is identified at block 820 as the optimal pacing vector setting.

Determining the trend of each HS parameter at block 818 may include determining whether the V-S2 interval trend presents a sudden slope change, e.g., from a substantially flat trend to a decreasing trend. An AV interval associated with a sudden change in the V-S2 interval trend may be identified as an optimal AV interval setting. The optimal AV interval may be further identified based on other HS trends, for example, a maximum S1 amplitude and/or a maximum S1-S2 interval.

In some embodiments, an automatically-identified optimal pace parameter setting may also be automatically programmed in the IMD at block 824. In other embodiments, the clinician or user reviews the reported HS data and recommended pace parameter setting(s) and may accept a recommended setting or select another setting based on the HS data.

HS sensing module, or circuitry, may be operably coupled to the control circuit 80 (FIG. 8) and be configured to receive analog signals from an HS sensor for sensing one or more of these heart sounds. For example, the HS sensing module may include one or more "channels" configured to particularly sense a specific heart sound based on frequency, duration, and timing of the heart sounds. For example, electrocardiogram/electrogram (ECG/EGM) sensing circuitry may be used by the control circuit 80 to set HS sensing windows used by HS sensing module for sensing the heart sounds. HS sensing module may include one or more sense amplifiers, filters, and rectifiers for optimizing a signal to noise ratio of heart sound signals. Separate and unique amplification and filtering properties may be provided for sensing each of the S1 through S4 sounds to improve signal quality as needed.

Bioimpedance, or intracardiac impedance, may be measured and used to represent physiological response information. For example, any of the IMDs described herein may measure an intracardiac impedance signal by injecting a current and measuring a voltage between electrodes of an electrode vector configuration (e.g., selected electrodes). For example, the IMD may measure an impedance signal by injecting a current (e.g., a non-pacing threshold current) between a first electrode (e.g., RV electrode) and an electrode located in the RV proximate the tricuspid valve and measuring a voltage between the first and second electrodes. Another vector that may be used is from the LV electrode to the RV electrode. One will recognize that other vector pair configurations may be used for stimulation and measurement. Impedance can be measured between any set of electrodes that encompass the tissue or cardiac chamber of interest. Thus, one can inject current and measure voltage to calculate the impedance on the same two electrodes (a bipolar configuration) or inject current and measure the voltage on two separate pairs of electrodes (e.g., one pair for current injection and one pair for voltage sense), hence, a quadripolar configuration. For a quadripolar electrode configuration, the current injection and voltage sense electrodes may be in line with each other (or closely parallel to) and the voltage sense electrodes may be within the current sense field. For example, if one injected current between the SVC coil electrode and the RV tip electrode, voltage sensing may be between the RV coil electrode and RV ring electrode. In such embodiments, a VfA lead may be used for the LV cardiac therapy or sensing. The impedance vectors can be configured to encompass a particular anatomical area of interest, such as the atrium or ventricles.

The illustrative methods and/or devices described herein may monitor one or more electrode vector configurations. Further, multiple impedance vectors may be measured concurrently and/or periodically relative to another. In at least one embodiment, the illustrative methods and/or devices may use impedance waveforms to acquire selection data (e.g., to find applicable fiducial points, to allow extraction of measurements from such waveforms, etc.) for optimizing CRT.

As used herein, the term "impedance signal" is not limited to a raw impedance signal. It should be implied that raw impedance signals may be processed, normalized, and/or filtered (e.g., to remove artifacts, noise, static, electromagnetic interference (EMI), and/or extraneous signals) to provide the impedance signal. Further, the term "impedance signal" may include various mathematical derivatives thereof including real and imaginary portions of the impedance signal, a conductance signal based on the impedance (i.e., the reciprocal or inverse of impedance), etc. In other words, the term "impedance signal" may be understood to include conductance signals, i.e., signals that are the reciprocal of the impedance signal.

In one or more embodiments of the methods and/or devices described herein, various patient physiological parameters (e.g., intracardiac impedance, heart sounds, cardiac cycle intervals such as R-R interval, etc.) may be monitored for use in acquiring selection data to optimize CRT (e.g., set AV and/or VV delay, optimize cardiac contractility, for example, by using and/or measuring impedance first derivative dZ/dt, select pacing site, select pacing vector, lead placement, or assess pacing capture from both the electrical and mechanical points of view (e.g., electrical capture may not mean mechanical capture, and the heart sounds and impedance may assist in assessing whether the electrical stimulus captures the heart or not by looking at the mechanical information from the heart sounds and impedance), select an effective electrode vector configuration for pacing, etc.). For example, intracardiac impedance signals between two or more electrodes may be monitored for use in providing such optimization.

FIG. 12 shows one example of a method 850 for acquiring selection data for one of the device parameter options (e.g., one of the selectable device parameters that may be used to optimize CRT, such as a potential AV delay that may be an optimal parameter). Other examples of using heart sounds to optimize cardiac therapy are described generally in U.S. Pat. No. 9,707,399, granted Jul. 18, 2017, entitled "Cardiac resynchronization therapy optimization based on intracardiac impedance and heart sounds," which is incorporated herein by reference in its entirety.

As shown, pacing therapy is delivered using one of the plurality of device options (block 852) (e.g., the plurality of device parameter options may be selected, determined and/or calculated AV delays, such as percentages of intrinsic AV delay, for example, 40% of intrinsic AV delay, 50% of intrinsic AV delay, 60% of intrinsic AV delay, 70% of intrinsic AV delay, 80% of intrinsic AV delay, etc.). For the device parameter option used to pace (block 852), selection data is acquired at each of a plurality of electrode vector configurations (e.g., intracardiac impedance is monitored over a plurality of cardiac cycles, and selection data is extracted using such impedance signal). As indicated by the decision block 854, if selection data has not been acquired from all desired electrode vector configurations, then the loop of acquiring selection data (e.g., the loop illustrated by blocks 858, 860, 862, and 864) is repeated. If selection data has been acquired from all desired electrode vector configurations, then another different device parameter option is used to deliver therapy (block 856) and the method 850 of FIG. 12 is repeated (e.g., for the different device parameter option) until selection data has been acquired for all the different device parameter options (e.g., selection data being collected at each of a plurality of electrode vector configurations for each of the different device parameter options).

As shown in the repeated loop of acquiring selection data for each of the desired electrode vector configurations (e.g., blocks 858, 860, 862, and 864), one of the plurality of electrode vector configurations is selected for use in acquiring selection data (block 858). Temporal fiducial points associated with at least a part of a systolic portion of at least one cardiac cycle and/or temporal fiducial points associated with at least a part of a diastolic portion of at least one cardiac cycle for the selected electrode vector configuration are acquired (block 860) (e.g., such as with use of heart sounds, analysis of impedance signal minimum and maximums, application of algorithms based on physiological parameters such as R-R intervals, etc.). For example, temporal fiducial points associated with the systolic and/or diastolic portions of the cardiac cycle may be acquired, temporal fiducial points associated with one or more defined segments within systolic and/or diastolic portions of the cardiac cycle may be acquired, and/or temporal fiducial points within or associated with one or more points and/or portions of a systolic and/or diastolic portion of the cardiac cycle may be acquired. Yet further, for example, temporal fiducial points associated with just the systolic portion or just the diastolic portion of the cardiac cycle may be acquired, temporal fiducial points associated with one or more defined segments within just the systolic portion or just the diastolic portion of the cardiac cycle may be acquired, and/or temporal fiducial points within or associated with one or more points and/or portions of just the systolic portion or just the diastolic portion of the cardiac cycle may be acquired. In other words, fiducial points may be acquired that are associated with either both the systolic and diastolic portions of the cardiac cycle or associated with just one of such portions of the cardiac cycle. Further, for example, such fiducial points may be representative or indicative of a measurement window and/or time period (e.g., interval, point, etc.) at or during which intracardiac impedance may be measured for use in an analysis as described herein.

In about the same timeframe (e.g., about simultaneously with the acquired fiducial points), an intracardiac impedance signal is acquired at the selected electrode vector configuration (block 862). With the acquired fiducial points and the acquired intracardiac impedance signal, measurements from the impedance signal are extracted based on the temporal fiducial points (block 864) (e.g., integral of the impedance signal in a measurement window defined between fiducial points, maximum slope of impedance signal in a measurement window defined between fiducial points, time between the fiducial points, maximum impedance at a fiducial point, etc.). One or more of such measurements may be comparable to desired values for such measurements allowing for a determination of whether the measurement may indicate that the device parameter option may be an effective device parameter for optimizing therapy (e.g., a scoring algorithm may be used to determine if a device parameter option may be an optimal parameter based on whether a plurality of such measurements meet certain criteria or thresholds).

The measurement data for each of the device parameter options (e.g., obtained such as described in FIG. 12) is determined for at least one cardiac cycle. In one or more embodiments, such measurement data is acquired for a plurality of cardiac cycles. The cardiac cycles during which measurement data is acquired may be any suitable cardiac cycle. In one or more embodiments, the selected cardiac cycles during which measurement data is acquired is based on the respiratory cycle. In at least one embodiment, the measurement data is acquired during cardiac cycles occurring at the end of a respiratory cycle (e.g., proximate the end of expiration).

Figure 13:
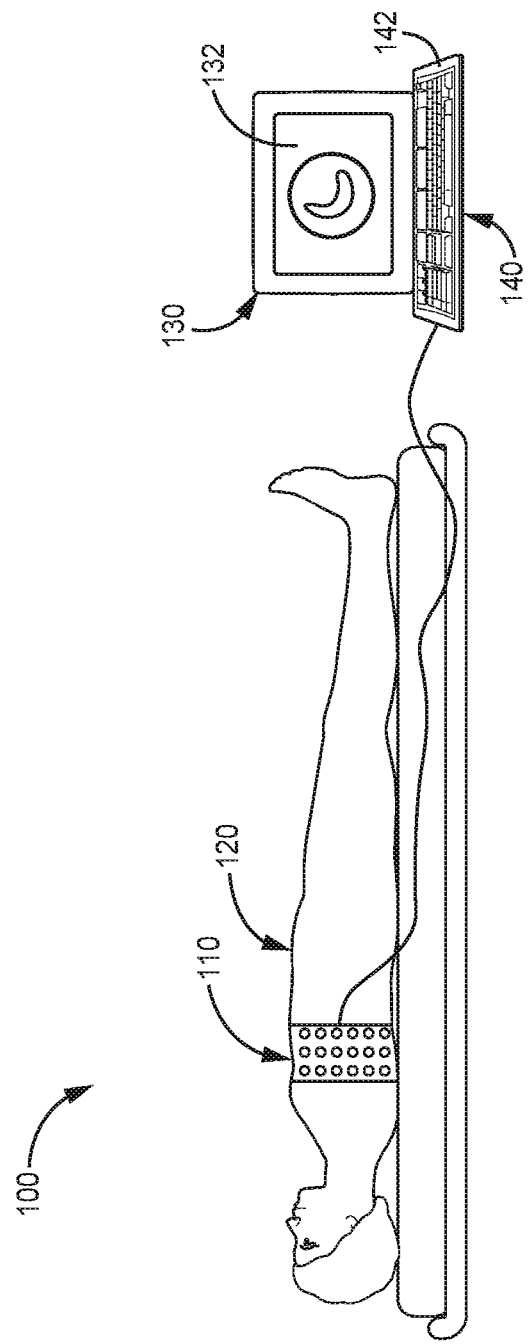
FIG. 13 is a diagram of an illustrative system including electrode apparatus, display apparatus, and computing apparatus for use with, e.g., the illustrative systems and devices of FIGS. 1-4 and 16.

FIG. 13 depicts an illustrative system 100 including electrode apparatus 110, display apparatus 130, and computing apparatus 140. The electrode apparatus 110 as shown includes a plurality of electrodes incorporated, or included, within a band wrapped around the chest, or torso, of a patient 120. The electrode apparatus 110 is operatively coupled to the computing apparatus 140 (e.g., through one or wired electrical connections, wirelessly, etc.) to provide electrical signals from each of the electrodes to the computing apparatus 140 for analysis, evaluation, etc. Illustrative electrode apparatus may be described in U.S. Pat. No. 9,320,446 entitled "Bioelectric Sensor Device and Methods" and issued on Apr. 26, 2016, which is incorporated herein by reference in its entirety. Further, illustrative electrode apparatus 110 will be described in more detail in reference to FIGS. 14-15.

Although not described herein, the illustrative system 100 may further include imaging apparatus. The imaging apparatus may be any type of imaging apparatus configured to image, or provide images of, at least a portion of the patient in a noninvasive manner. For example, the imaging apparatus may not use any components or parts that may be located within the patient to provide images of the patient except noninvasive tools such as contrast solution. It is to be understood that the illustrative systems, methods, and interfaces described herein may further use imaging apparatus to provide noninvasive assistance to a user (e.g., a physician) to calibrate and/or deliver a VfA pacing therapy, to locate and position a device to deliver VfA cardiac pacing therapy, and/or to locate or select a pacing electrode or pacing vector proximate the patient's heart for ventricle from atrium pacing therapy in conjunction with the evaluation of ventricle from atrium pacing therapy.

For example, the illustrative systems, methods, and interfaces may provide image-guided navigation that may be used to navigate leads including leadless devices, electrodes, leadless electrodes, wireless electrodes, catheters, etc., within the patient's body while also providing noninvasive cardiac therapy evaluation including determining whether a ventricle from atrium (VfA) paced setting is optimal or determining whether one or more selected parameters are optimal, such as selected location information (e.g., location information for the electrodes to target a particular location in the left ventricle). Illustrative systems and methods that use imaging apparatus and/or electrode apparatus may be described in U.S. Patent Publication No. 2014/0371832 filed on Jun. 12, 2013, and entitled "Implantable Electrode Location Selection," U.S. Patent Publication No. 2014/0371833 filed on Jun. 12, 2013, and entitled "Implantable Electrode Location Selection," U.S. Patent Publication No. 2014/0323892 filed on Mar. 27, 2014 and entitled "Systems, Methods, and Interfaces for Identifying Effective Electrodes," U.S. Patent Publication No. 2014/0323882 filed on Mar. 27, 2014 and entitled "Systems, Methods, and Interfaces for Identifying Optical-Electrical Vectors," each of which is incorporated herein by reference in its entirety.

Illustrative imaging apparatus may be configured to capture x-ray images and/or any other alternative imaging modality. For example, the imaging apparatus may be configured to capture images, or image data, using isocentric fluoroscopy, bi-plane fluoroscopy, ultrasound, computed tomography (CT), multi-slice computed tomography (MSCT), magnetic resonance imaging (MRI), high frequency ultrasound (HIFU), optical coherence tomography (OCT), intravascular ultrasound (IVUS), two-dimensional (2D) ultrasound, three dimensional (3D) ultrasound, four-dimensional (4D) ultrasound, intraoperative CT, intraoperative MRI, etc. Further, it is to be understood that the imaging apparatus may be configured to capture a plurality of consecutive images (e.g., continuously) to provide video frame data. In other words, a plurality of images taken over time using the imaging apparatus may provide video frame, or motion picture, data. Additionally, the images may also be obtained and displayed in two, three, or four dimensions. In more advanced forms, four-dimensional surface rendering of the heart or other regions of the body may also be achieved by incorporating heart data or other soft tissue data from a map or from pre-operative image data captured by MRI, CT, or echocardiography modalities. Image datasets from hybrid modalities, such as positron emission tomography (PET) combined with CT, or single photon emission computer tomography (SPECT) combined with CT, could also provide functional image data superimposed onto anatomical data, e.g., to be used to navigate treatment apparatus proximate target locations (e.g., such as locations within the left ventricle, including a selected location within the high posterior basal and/or septal area of the left ventricular cavity) within the heart or other areas of interest.

Systems and/or imaging apparatus that may be used in conjunction with the illustrative systems and method described herein are described in U.S. Pat. App. Pub. No. 2005/0008210 to Evron et al. published on Jan. 13, 2005, U.S. Pat. App. Pub. No. 2006/0074285 to Zarkh et al. published on Apr. 6, 2006, U.S. Pat. App. Pub. No. 2011/0112398 to Zarkh et al. published on May 12, 2011, U.S. Pat. App. Pub. No. 2013/0116739 to Brada et al. published on May 9, 2013, U.S. Pat. No. 6,980,675 to Evron et al. issued on Dec. 27, 2005, U.S. Pat. No. 7,286,866 to Okerlund et al. issued on Oct. 23, 2007, U.S. Pat. No. 7,308,297 to Reddy et al. issued on Dec. 11, 2011, U.S. Pat. No. 7,308,299 to Burrell et al. issued on Dec. 11, 2011, U.S. Pat. No. 7,321,677 to Evron et al. issued on Jan. 22, 2008, U.S. Pat. No. 7,346,381 to Okerlund et al. issued on Mar. 18, 2008, U.S. Pat. No. 7,454,248 to Burrell et al. issued on Nov. 18, 2008, U.S. Pat. No. 7,499,743 to Vass et al. issued on Mar. 3, 2009, U.S. Pat. No. 7,565,190 to Okerlund et al. issued on Jul. 21, 2009, U.S. Pat. No. 7,587,074 to Zarkh et al. issued on Sep. 8, 2009, U.S. Pat. No. 7,599,730 to Hunter et al. issued on Oct. 6, 2009, U.S. Pat. No. 7,613,500 to Vass et al. issued on Nov. 3, 2009, U.S. Pat. No. 7,742,629 to Zarkh et al. issued on Jun. 22, 2010, U.S. Pat. No. 7,747,047 to Okerlund et al. issued on Jun. 29, 2010, U.S. Pat. No. 7,778,685 to Evron et al. issued on Aug. 17, 2010, U.S. Pat. No. 7,778,686 to Vass et al. issued on Aug. 17, 2010, U.S. Pat. No. 7,813,785 to Okerlund et al. issued on Oct. 12, 2010, U.S. Pat. No. 7,996,063 to Vass et al. issued on Aug. 9, 2011, U.S. Pat. No. 8,060,185 to Hunter et al. issued on Nov. 15, 2011, and U.S. Pat. No. 8,401,616 to Verard et al. issued on Mar. 19, 2013, each of which is incorporated herein by reference in its entirety.

The display apparatus 130 and the computing apparatus 140 may be configured to display and analyze data such as, e.g., electrical signals (e.g., electrocardiogram data), cardiac information representative of one or more of mechanical cardiac functionality and electrical cardiac functionality (e.g., mechanical cardiac functionality only, electrical cardiac functionality only, or both mechanical cardiac functionality and electrical cardiac functionality), etc. Cardiac information may include, e.g., electrical heterogeneity information or electrical dyssynchrony information, surrogate electrical activation information or data, etc. that is generated using electrical signals gathered, monitored, or collected, using the electrode apparatus 110. In at least one embodiment, the computing apparatus 140 may be a server, a personal computer, or a tablet computer. The computing apparatus 140 may be configured to receive input from input apparatus 142 and transmit output to the display apparatus 130. Further, the computing apparatus 140 may include data storage that may allow for access to processing programs or routines and/or one or more other types of data, e.g., for calibrating and/or delivering pacing therapy for driving a graphical user interface configured to noninvasively assist a user in targeting placement of a pacing device, and/or for evaluating pacing therapy at that location (e.g., the location of an implantable electrode used for pacing, the location of pacing therapy delivered by a particular pacing vector, etc.).

The computing apparatus 140 may be operatively coupled to the input apparatus 142 and the display apparatus 130 to, e.g., transmit data to and from each of the input apparatus 142 and the display apparatus 130. For example, the computing apparatus 140 may be electrically coupled to each of the input apparatus 142 and the display apparatus 130 using, e.g., analog electrical connections, digital electrical connections, wireless connections, bus-based connections, network-based connections, internet-based connections, etc. As described further herein, a user may provide input to the input apparatus 142 to manipulate, or modify, one or more graphical depictions displayed on the display apparatus 130 and to view and/or select one or more pieces of information related to the cardiac therapy.

Although as depicted the input apparatus 142 is a keyboard, it is to be understood that the input apparatus 142 may include any apparatus capable of providing input to the computing apparatus 140 for performing the functionality, methods, and/or logic described herein. For example, the input apparatus 142 may include a mouse, a trackball, a touchscreen (e.g., capacitive touchscreen, a resistive touchscreen, a multi-touch touchscreen, etc.), etc. Likewise, the display apparatus 130 may include any apparatus capable of displaying information to a user, such as a graphical user interface 132 including cardiac information, textual instructions, graphical depictions of electrical activation information, graphical depictions of anatomy of a human heart, images or graphical depictions of the patient's heart, graphical depictions of a leadless pacing device used to calibrate and/or deliver pacing therapy, graphical depictions of a leadless pacing device being positioned or placed to provide VfA pacing therapy, graphical depictions of locations of one or more electrodes, graphical depictions of a human torso, images or graphical depictions of the patient's torso, graphical depictions or actual images of implanted electrodes and/or leads, etc. Further, the display apparatus 130 may include a liquid crystal display, an organic light-emitting diode screen, a touchscreen, a cathode ray tube display, etc.

The processing programs or routines stored and/or executed by the computing apparatus 140 may include programs or routines for computational mathematics, matrix mathematics, dispersion determinations (e.g., standard deviations, variances, ranges, interquartile ranges, mean absolute differences, average absolute deviations, etc.), filtering algorithms, maximum value determinations, minimum value determinations, threshold determinations, moving windowing algorithms, decomposition algorithms, compression algorithms (e.g., data compression algorithms), calibration algorithms, image construction algorithms, signal processing algorithms (e.g., various filtering algorithms, Fourier transforms, fast Fourier transforms, etc.), standardization algorithms, comparison algorithms, vector mathematics, or any other processing required to implement one or more illustrative methods and/or processes described herein. Data stored and/or used by the computing apparatus 140 may include, for example, electrical signal/waveform data from the electrode apparatus 110, dispersions signals, windowed dispersions signals, parts or portions of various signals, electrical activation times from the electrode apparatus 110, graphics (e.g., graphical elements, icons, buttons, windows, dialogs, pull-down menus, graphic areas, graphic regions, 3D graphics, etc.), graphical user interfaces, results from one or more processing programs or routines employed according to the disclosure herein (e.g., electrical signals, cardiac information, etc.), or any other data that may be necessary for carrying out the one and/or more processes or methods described herein.

In one or more embodiments, the illustrative systems, methods, and interfaces may be implemented using one or more computer programs executed on programmable computers, such as computers that include, for example, processing capabilities, data storage (e.g., volatile or non-volatile memory and/or storage elements), input devices, and output devices. Program code and/or logic described herein may be applied to input data to perform the functionality described herein and generate desired output information. The output information may be applied as input to one or more other devices and/or methods as described herein or as would be applied in a known fashion.

The one or more programs used to implement the systems, methods, and/or interfaces described herein may be provided using any programmable language, e.g., a high-level procedural and/or object orientated programming language that is suitable for communicating with a computer system. Any such programs may, for example, be stored on any suitable device, e.g., a storage media, that is readable by a general or special purpose program running on a computer system (e.g., including processing apparatus) for configuring and operating the computer system when the suitable device is read for performing the procedures described herein. In other words, at least in one embodiment, the illustrative systems, methods, and/or interfaces may be implemented using a computer readable storage medium, configured with a computer program, where the storage medium so configured causes the computer to operate in a specific and predefined manner to perform functions described herein. Further, in at least one embodiment, the illustrative systems, methods, and/or interfaces may be described as being implemented by logic (e.g., object code) encoded in one or more non-transitory media that includes code for execution and, when executed by a processor, is operable to perform operations such as the methods, processes, and/or functionality described herein.

The computing apparatus 140 may be, for example, any fixed or mobile computer system (e.g., a controller, a microcontroller, a personal computer, minicomputer, tablet computer, etc.) and may be generally described as including processing circuitry. The exact configuration of the computing apparatus 140 is not limiting, and essentially any device capable of providing suitable computing capabilities and control capabilities (e.g., graphics processing, etc.) may be used. As described herein, a digital file may be any medium (e.g., volatile or non-volatile memory, a CD-ROM, a punch card, magnetic recordable medium such as a disk or tape, etc.) containing digital bits (e.g., encoded in binary, trinary, etc.) that may be readable and/or writeable by computing apparatus 140 described herein. Also, as described herein, a file in user-readable format may be any representation of data (e.g., ASCII text, binary numbers, hexadecimal numbers, decimal numbers, graphically, etc.) presentable on any medium (e.g., paper, a display, etc.) readable and/or understandable by a user.

In view of the above, it will be readily apparent that the functionality as described in one or more embodiments according to the present disclosure may be implemented in any manner as would be known to one skilled in the art. As such, the computer language, the computer system, or any other software/hardware which is to be used to implement the processes described herein shall not be limiting on the scope of the systems, processes, or programs (e.g., the functionality provided by such systems, processes, or programs) described herein.

Figure 14:
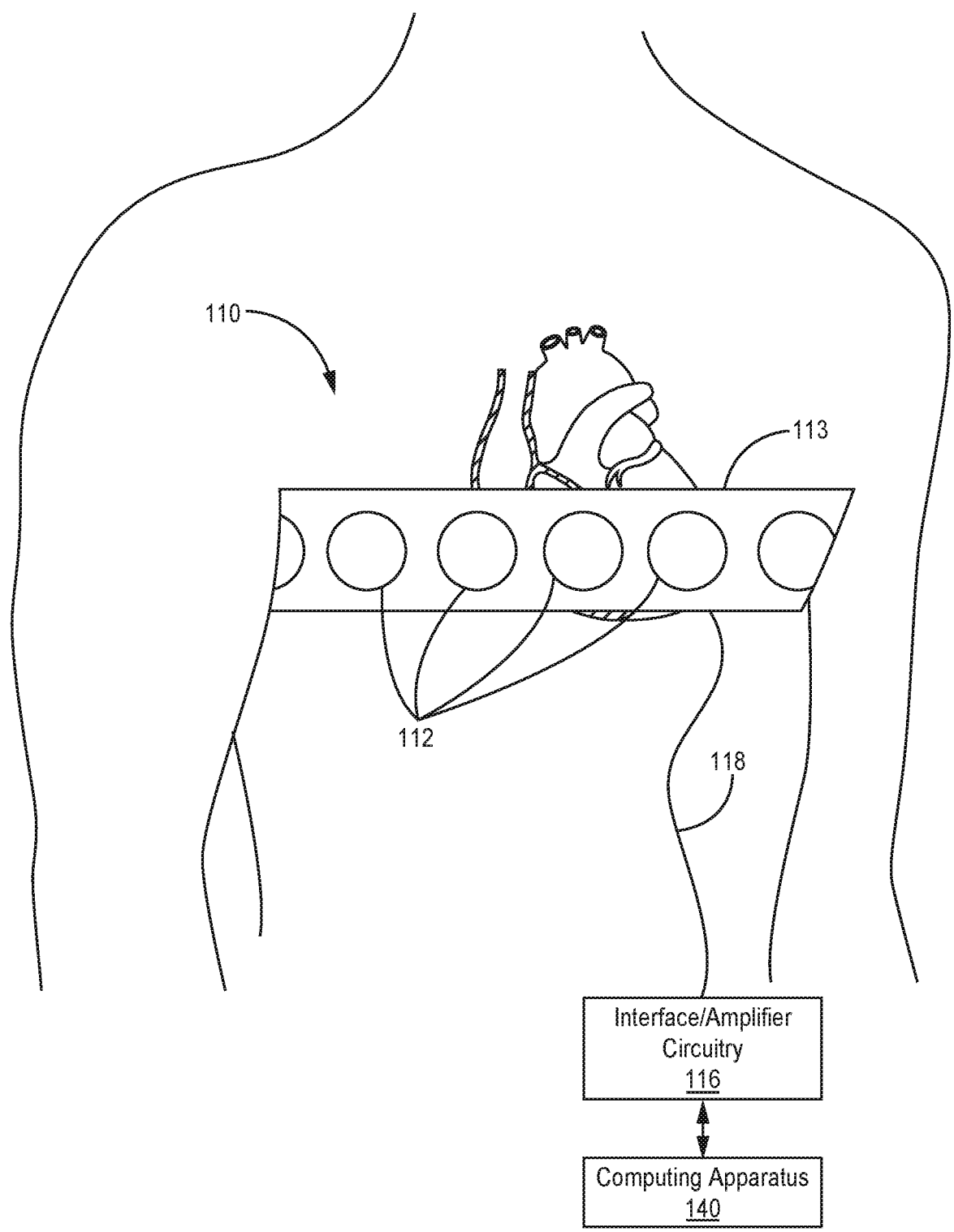
FIGS. 14-15 are diagrams of illustrative external electrode apparatus for measuring torso-surface potentials for use with, e.g., the illustrative systems and devices of FIGS. 1-4 and 16.
Figure 15:
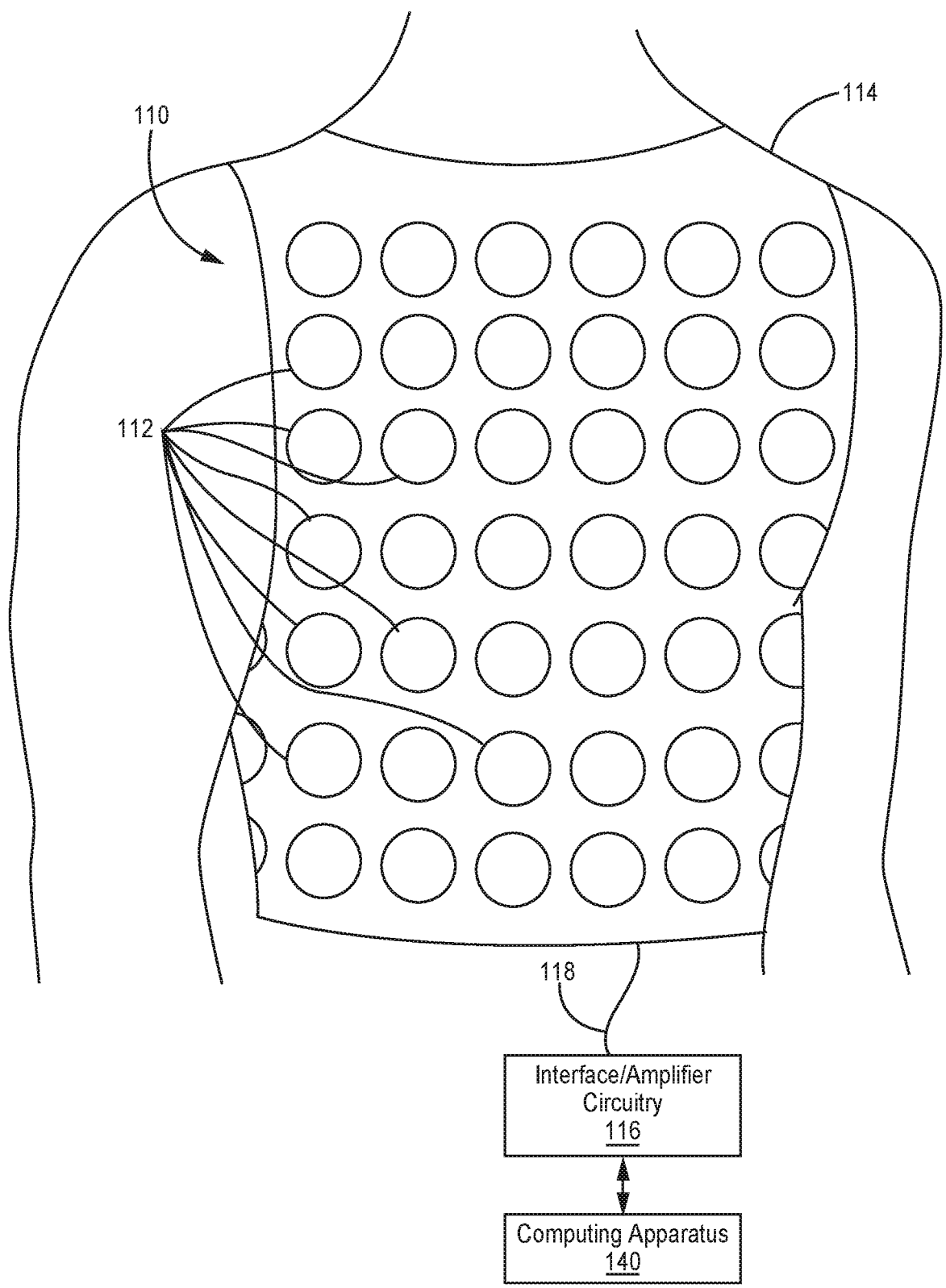

Electrical activation times of the patient's heart may be useful to evaluate a patient's cardiac condition and/or to calibrate, deliver, or evaluate ventricle from atrium (VfA) cardiac therapy to be or being delivered to a patient. Surrogate electrical activation information or data of one or more regions of a patient's heart may be monitored, or determined, using electrode apparatus 110 as shown in FIGS. 13-15. The illustrative electrode apparatus 110 may be configured to measure body-surface potentials of a patient 120 and, more particularly, torso-surface potentials of a patient 120.

As shown in FIG. 14, the illustrative electrode apparatus 110 may include a set, or array, of electrodes 112, a strap 113, and interface/amplifier circuitry 116. In at least one embodiment, a portion of the set of electrodes may be used wherein the portion corresponds to a particular location on the patient's heart. The electrodes 112 may be attached, or coupled, to the strap 113, and the strap 113 may be configured to be wrapped around the torso of a patient 120 such that the electrodes 112 surround the patient's heart. As further illustrated, the electrodes 112 may be positioned around the circumference of a patient 120, including the posterior, lateral, posterolateral, anterolateral, and anterior locations of the torso of a patient 120.

Further, the electrodes 112 may be electrically connected to interface/amplifier circuitry 116 via wired connection 118. The interface/amplifier circuitry 116 may be configured to amplify the signals from the electrodes 112 and provide the signals to the computing apparatus 140. Other illustrative systems may use a wireless connection to transmit the signals sensed by electrodes 112 to the interface/amplifier circuitry 116 and, in turn, the computing apparatus 140, e.g., as channels of data. For example, the interface/amplifier circuitry 116 may be electrically coupled to each of the computing apparatus 140 and the display apparatus 130 using, e.g., analog electrical connections, digital electrical connections, wireless connections, bus-based connections, network-based connections, internet-based connections, etc.

Although in the example of FIG. 14 the electrode apparatus 110 includes a strap 113, in other examples any of a variety of mechanisms, e.g., tape or adhesives, may be employed to aid in the spacing and placement of electrodes 112. In some examples, the strap 113 may include an elastic band, strip of tape, or cloth. In other examples, the electrodes 112 may be placed individually on the torso of a patient 120. Further, in other examples, electrodes 112 (e.g., arranged in an array) may be part of, or located within, patches, vests, and/or other manners of securing the electrodes 112 to the torso of the patient 120.

The electrodes 112 may be configured to surround the heart of the patient 120 and record, or monitor, the electrical signals associated with the depolarization and repolarization of the heart after the signals have propagated through the torso of a patient 120. Each of the electrodes 112 may be used in a unipolar configuration to sense the torso-surface potentials that reflect the cardiac signals. The interface/amplifier circuitry 116 may also be coupled to a return or indifferent electrode (not shown) that may be used in combination with each electrode 112 for unipolar sensing. In some examples, there may be about 12 to about 50 electrodes 112 spatially distributed around the torso of the patient. Other configurations may have more or fewer electrodes 112.

The computing apparatus 140 may record and analyze the electrical activity (e.g., torso-surface potential signals) sensed by electrodes 112 and amplified/conditioned by the interface/amplifier circuitry 116. The computing apparatus 140 may be configured to analyze the signals from the electrodes 112 to provide as anterior and posterior electrode signals and surrogate cardiac electrical activation times, e.g., representative of actual, or local, electrical activation times of one or more regions of the patient's heart as will be further described herein. The computing apparatus 140 may be configured to analyze the signals from the electrodes 112 to provide as anterior-septal electrode signals and surrogate cardiac electrical activation times, e.g., representative of actual, or local, electrical activation times of one or more anterior-septal regions of the patient's heart, as will be further described herein, e.g., for use in calibrating, delivering, and/or evaluating VfA pacing therapy. Further, the electrical signals measured at the left anterior surface location of a patient's torso may be representative, or surrogates, of electrical signals of the left anterior left ventricle region of the patient's heart, electrical signals measured at the left lateral surface location of a patient's torso may be representative, or surrogates, of electrical signals of the left lateral left ventricle region of the patient's heart, electrical signals measured at the left posterolateral surface location of a patient's torso may be representative, or surrogates, of electrical signals of the posterolateral left ventricle region of the patient's heart, and electrical signals measured at the posterior surface location of a patient's torso may be representative, or surrogates, of electrical signals of the posterior left ventricle region of the patient's heart. In one or more embodiments, measurement of activation times can be performed by measuring the period of time between an onset of cardiac depolarization (e.g., onset of QRS complex) and an appropriate fiducial point such as, e.g., a peak value, a minimum value, a minimum slope, a maximum slope, a zero crossing, a threshold crossing, etc.

Additionally, the computing apparatus 140 may be configured to provide graphical user interfaces depicting the surrogate electrical activation times obtained using the electrode apparatus 110. Illustrative systems, methods, and/or interfaces may noninvasively use the electrical information collected using the electrode apparatus 110 to evaluate a patient's cardiac condition and/or to calibrate, deliver, or evaluate VfA pacing therapy to be or being delivered to the patient.

FIG. 15 illustrates another illustrative electrode apparatus 110 that includes a plurality of electrodes 112 configured to surround the heart of the patient 120 and record, or monitor, the electrical signals associated with the depolarization and repolarization of the heart after the signals have propagated through the torso of the patient 120. The electrode apparatus 110 may include a vest 114 upon which the plurality of electrodes 112 may be attached, or to which the electrodes 112 may be coupled. In at least one embodiment, the plurality, or array, of electrodes 112 may be used to collect electrical information such as, e.g., surrogate electrical activation times.

Similar to the electrode apparatus 110 of FIG. 14, the electrode apparatus 110 of FIG. 13 may include interface/amplifier circuitry 116 electrically coupled to each of the electrodes 112 through a wired connection 118 and be configured to transmit signals from the electrodes 112 to computing apparatus 140. As illustrated, the electrodes 112 may be distributed over the torso of a patient 120, including, for example, the anterior, lateral, posterolateral, anterolateral, and posterior surfaces of the torso of the patient 120.

The vest 114 may be formed of fabric with the electrodes 112 attached to the fabric. The vest 114 may be configured to maintain the position and spacing of electrodes 112 on the torso of the patient 120. Further, the vest 114 may be marked to assist in determining the location of the electrodes 112 on the surface of the torso of the patient 120. In one or more embodiments, the vest 114 may include about 17 or more anterior electrodes positionable proximate the anterior torso of the patient, and about 39 or more posterior electrodes positionable proximate the anterior torso of the patient. In some examples, there may be about 25 electrodes 112 to about 256 electrodes 112 distributed around the torso of the patient 120, though other configurations may have more or fewer electrodes 112.

As described herein, the electrode apparatus 110 may be configured to measure electrical information (e.g., electrical signals) representing different regions of a patient's heart. For example, activation times of different regions of a patient's heart can be approximated from surface electrocardiogram (ECG) activation times measured using surface electrodes in proximity to surface areas corresponding to the different regions of the patient's heart. In at least one example, activation times of the anterior-septal region of a patient's heart can be approximated from surface ECG activation times measured using surface electrodes in proximity to surface areas corresponding to the anterior-septal region of the patient's heart. That is, a portion of the set of electrodes 112, and not the entire set, can be used to generate activation times corresponding to a particular location of the patient's heart that the portion of the set of electrodes corresponds to.

The illustrative systems, methods, and interfaces may be used to provide noninvasive assistance to a user in the evaluation of a patient's cardiac health or status, and/or the evaluation of cardiac therapy such as ventricle from atrium (VfA) pacing therapy by use of the electrode apparatus 110 (e.g., cardiac therapy being presently-delivered to a patient during implantation or after implantation). Further, the illustrative systems, methods, and interfaces may be used to assist a user in the configuration, or calibration, of the cardiac therapy, such as VfA pacing therapy, to be or being delivered to a patient.

VfA pacing can be described as providing a synchronized homogeneous activation of ventricles of the heart. As an example, patients with atrial-ventricular (AV) block or prolonged AV timings that can lead to heart failure who have otherwise intact (e.g., normal) QRS can benefit from VfA pacing therapy. In addition, as an example, VfA pacing may provide beneficial activation for heart failure patients with intrinsic ventricular conduction disorders. Further, proper placement of VfA pacing can provide optimal activation of the ventricles for such patients. Further, left ventricular (LV) resynchronization for heart failure patients with left bundle branch block (LBBB) may find that VfA pacing enables easier access to left ventricular endocardium without exposing the leadless device or lead to the endocardial blood pool. At the same time, in that example, this can help engage part of the conduction system to potentially correct LBBB and effectively resynchronize the patient.

Electrical activity may be monitored using a plurality of external electrodes, such as electrodes 112 of FIGS. 13-15. The electrical activity can be monitored by a plurality of electrodes during VfA pacing therapy or in the absence of VfA pacing therapy. The monitored electrical activity can be used to evaluate VfA pacing therapy to a patient. The electrical activity monitored using the ECG belt described can be used to evaluate at least one paced setting of the VfA pacing therapy on the heart. As an example, a paced setting can be any one parameter or a combination of parameters including, but not limited to, electrode position, pacing polarity, pacing output, pacing pulse width, timing at which VfA pacing is delivered relative to atrial (A) timing, pacing rate, etc. Further, as an example, the location of the leadless device or a pacing lead can include a location in the left ventricle, accessed through the right atrium within, or in close proximity to, the high posterior basal and/or septal (HPBS) area of the left ventricular cavity. Moreover, pacing in, or in close proximity to, the HPBS area can be selective (e.g., involving stimulation of a particular area of the HPBS alone) or non-selective (e.g., combined pacing at the location of the HPBS and other atrial and/or ventricular septum areas).

Further, body-surface isochronal maps of ventricular activation can be constructed using the monitored electrical activity during VfA pacing therapy or in the absence of VfA pacing therapy. The monitored electrical activity and/or the map of ventricular activation can be used to generate electrical heterogeneity information (EHI). The electrical heterogeneity information can include determining metrics of electrical heterogeneity. The metrics of electrical heterogeneity can include a metric of standard deviation of activation times (SDAT) of electrodes on a left side of a torso of the patient and/or a metric of mean left ventricular activation time (LVAT) of electrodes on the left side of the torso of the patient. A metric of LVAT may be determined from electrodes on both the anterior and posterior surfaces, which are more proximal to the left ventricle. The metrics of electrical heterogeneity information can include a metric of mean right ventricular activation time (RVAT) of electrodes on the right side of the torso of the patient. A metric of RVAT may be determined from electrodes on both the anterior and posterior surfaces which are more proximal to the right ventricle. The metrics of electrical heterogeneity can include a metric of mean total activation time (mTAT) taken from a plurality of electrode signals from both sides of the torso of the patient, or it may include other metrics (e.g., standard deviation, interquartile deviations, a difference between a latest activation time and earliest activation time) reflecting a range or dispersion of activation times on a plurality of electrodes located on the right side of the patient torso or left side of the patient torso, or combining both right and left sides of the patient torso. The metrics of electrical heterogeneity information can include a metric of anterior-septal activation times (ASAT) of electrodes on the torso in close proximity to the anterior-septal portion of the heart.

Electrical heterogeneity information (EHI) may be generated during delivery of VfA pacing therapy at one or more VfA paced settings. The electrical heterogeneity information can be generated using metrics of electrical heterogeneity. As an example, the metrics of electrical heterogeneity can include one or more of an SDAT, an LVAT, an RVAT, an mTAT, and an ASAT. In at least one embodiment, only ASAT may be determined and further used, and/or ASAT may be more heavily weighted than other values.

One or more paced settings associated with the VfA pacing therapy may be evaluated. A paced setting can include a plurality of pacing parameters. The plurality of pacing parameters can be optimal if the patient's cardiac condition improves, if the VfA pacing therapy is effectively capturing a desired portion of the left ventricle (e.g., the high posterior basal and/or septal area), and/or if a metric of electrical heterogeneity improves by a certain threshold compared to a baseline rhythm or therapy. In at least one embodiment, the determination of whether the paced setting is optimal can be based on at least one metric of electrical heterogeneity generated from electrical activity during VfA pacing (and also, in some embodiments, during native conduction, or in the absence of VfA pacing). The at least one metric can include one or more of an SDAT, an LVAT, an RVAT, an mTAT, and an ASAT.

Further, the plurality of pacing parameters can be optimal if a metric of electrical heterogeneity is greater than or less than a particular threshold, and/or if the location of the pacing therapy to excite the left ventricle causes a particular pattern of excitation of the muscle fibers in the heart. In addition, the plurality of pacing parameters can be optimal if a metric of electrical heterogeneity indicates a correction of a left bundle branch block (LBBB), and/or if a metric of electrical heterogeneity indicates a complete engagement of a Purkinje system, etc. As an example, a metric of electrical heterogeneity of an ASAT less than or equal to a threshold (e.g., a threshold of 30 ms) and an LVAT less than or equal to a threshold (e.g., a threshold of 30 ms) can indicate a correction of an LBBB, and thus, the paced setting is optimal. As an example, a metric of electrical heterogeneity of an RVAT less than or equal to a threshold (e.g., a threshold of 30 ms), an ASAT less than or equal to a threshold (e.g., a threshold of 30 ms), and an LVAT less than or equal to a threshold (e.g., a threshold of 30 ms) can indicate a complete engagement of the Purkinje system, and thus the paced setting is may be optimal.

The paced setting can be determined to be optimal in response to the VfA pacing therapy using the paced setting being acceptable, being beneficial, being indicative of complete engagement of patient's native cardiac conduction system, being indicative of correction of a ventricular conduction disorder (e.g., left bundle branch block), etc. A paced setting can include one or more of a pacing electrode position (including one or more of a depth, an angle, an amount of turn for a screw-based fixation mechanism, etc.), a voltage, a pulse width, an intensity, a pacing polarity, a pacing vector, a pacing waveform, a timing of the pacing delivered relative to an intrinsic or paced atrial event or relative to the intrinsic His bundle potential, and/or a pacing location, etc. A pacing vector can include any two or more pacing electrodes such as, e.g., a tip electrode to a can electrode, a tip electrode to a ring electrode etc., that are used to deliver the VfA pacing therapy, etc. The pacing location can refer to the location of any of the one or more pacing electrodes that are positioned using a lead, a leadless device, and/or any device or apparatus configured to deliver VfA.

A paced setting for VfA pacing therapy may be adjusted. In at least one embodiment, the paced setting can be adjusted in response to the paced setting being not optimal. In at least one embodiment, the paced setting can be adjusted in response to the paced setting being within an optimal range but in order to determine whether the paced setting can be at a position within the optimal range that is more beneficial, more useful, more functional, etc., for the VfA pacing therapy. The paced setting could be adjusted to find the most optimal metric of electrical heterogeneity.

In one or more embodiments, a determination of whether the paced setting is optimal can be based on a particular metric of electrical heterogeneity using an ECG belt. In at least one example, the paced setting can be adjusted at intervals that correlate with a change in the metric of electrical heterogeneity until the metric of electrical heterogeneity is at or proximate a particular metric value. For instance, the adjusting of the paced setting can cause the metric of electrical heterogeneity to approach a particular threshold metric of electrical heterogeneity and, as the metric approaches the particular threshold, the rate at which the paced setting is adjusted can be slowed down. Put another way, as the metric of electrical heterogeneity is further from the particular threshold metric, the paced setting can be adjusted more quickly and as the metric of electrical heterogeneity gets closer to the particular threshold metric, the paced setting can be adjusted more slowly until the metric of electrical heterogeneity is at the particular threshold metric.

Various techniques for utilizing an electrode apparatus having a plurality of external electrodes to monitor electrical activity from tissue of a patient that may be used with the devices, systems, and methods described herein are disclosed in U.S. patent application Ser. No. 15/934,517, filed 23 Mar. 2018, entitled "Evaluation of Ventricle from Atrium Pacing Therapy," which is incorporated herein by reference in its entirety.

Various embodiments of the implantable medical device may be used for optimizing CRT using electrical and/or mechanical activity. Alternatively, or in addition to using heart sounds, for example, a motion detector may provide one or more signals that indicate mechanical activity within the patient's heart, which may be used in conjunction with electrical activity detected using one or more electrodes of the implantable medical device. The electrical and/or mechanical activity detected may also be used for evaluating markers of heart chamber remodeling, such as left atrial and left ventricular remodeling, which may occur over a long period of time.

Figure 16:
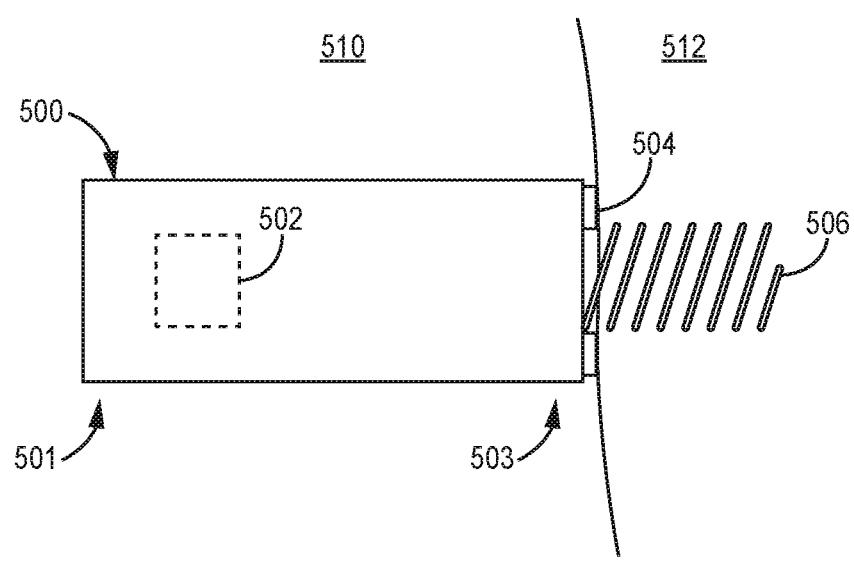
FIG. 16 is a diagram of an illustrative implantable medical device having electrodes and an accelerometer for use with various systems and methods of the present disclosure.

FIG. 16 schematically shows an implantable medical device, in particular an LPD 500, attached to an atrioventricular (AV) septal wall 512, or AV septum, from the right atrium (RA) 510. Although an LPD is shown, in other embodiments, the implantable medical device may include a lead. The LPD 500 may include any one or more of the other components included in a medical device described in this disclosure. In the illustrated embodiment, the LPD 500 includes at least an activity sensor, or motion detector 502, such as an accelerometer, which may be coupled to a sensing circuit of the LPD. In some cases, the motion detector 502 may be similar to the motion detector 11 (FIG. 5). The LPD 500 also includes at least one atrial electrode 504 that may be implanted in the atrium of the patient's heart to deliver cardiac therapy or sense electrical activity of the atrium and at least one ventricular electrode 506 that may be implanted in a septal wall, for example, in a ventricular side of a septal wall, to deliver cardiac therapy to or sense electrical activity of the ventricle.

In one or more embodiments, a housing of the LPD 500 extends from a proximal end region 501 to a distal end region 503. The atrial electrode 504 may be leadlessly coupled to the housing. The ventricular electrode 506 may also be leadlessly coupled to the distal end region 503 of the housing and, in particular, may leadlessly extend from the distal end region. In general, the ventricular electrode 506 is positioned distal to the atrial electrode 504. Each of the motion detector 502, a therapy delivery circuit, a sensing circuit, and a controller having a processor may be enclosed or contained within the housing of the LPD 500.

In some embodiments, the atrial electrode 504 may be an RA electrode positioned on the surface of the AV septal wall 512 in the RA 510, and the ventricular electrode 506 may be a tissue-piercing electrode positioned in the AV septal wall 512. As illustrated, the atrial electrode 504 is implanted in the RA 510 in contact with the AV septal wall 512, and the ventricular electrode 506 is implanted on the left-ventricular side in the AV septal wall 512. In one or more embodiments, the ventricular electrode 506 is implanted from the triangle of Koch region of the RA of the patient's heart to deliver cardiac therapy to or sense electrical activity of the left ventricle (LV) in the basal region, septal region, or basal-septal region of the LV myocardium of the patient's heart.

The LPD 500 may include one or more of the motion detectors 502 configured to detect mechanical motions, or mechanical activity, of the patient's heart. Other leads, structures, or LPDs may or may not reside in other chambers of the heart (e.g., the left atrium or right ventricle for cardiac therapy. When the LPD 500 includes two or more electrodes carried on the exterior housing of the LPD 500, other leads of structure may not be necessary.

The motion detector 502 may include one or more accelerometers or other such devices capable of detecting motion and/or position of the LPD 500. For example, the motion detector 502 may include a 3-axis accelerometer that is configured to detect accelerations in any direction in space. Specifically, the 3-axis accelerator may be used to detect the LPD 500 motion that may indicate cardiac events. For example, the LPD 500 may move with a chamber wall of the heart, such as AV septal wall 512, and the detected changes in acceleration may indicate contractions or other mechanical activity within the heart. Accelerations detected by the motion detector 502 may be used by a processor of the LPD 500 to identify potential noise in signals detected by the sensing circuit.

Figure 17:
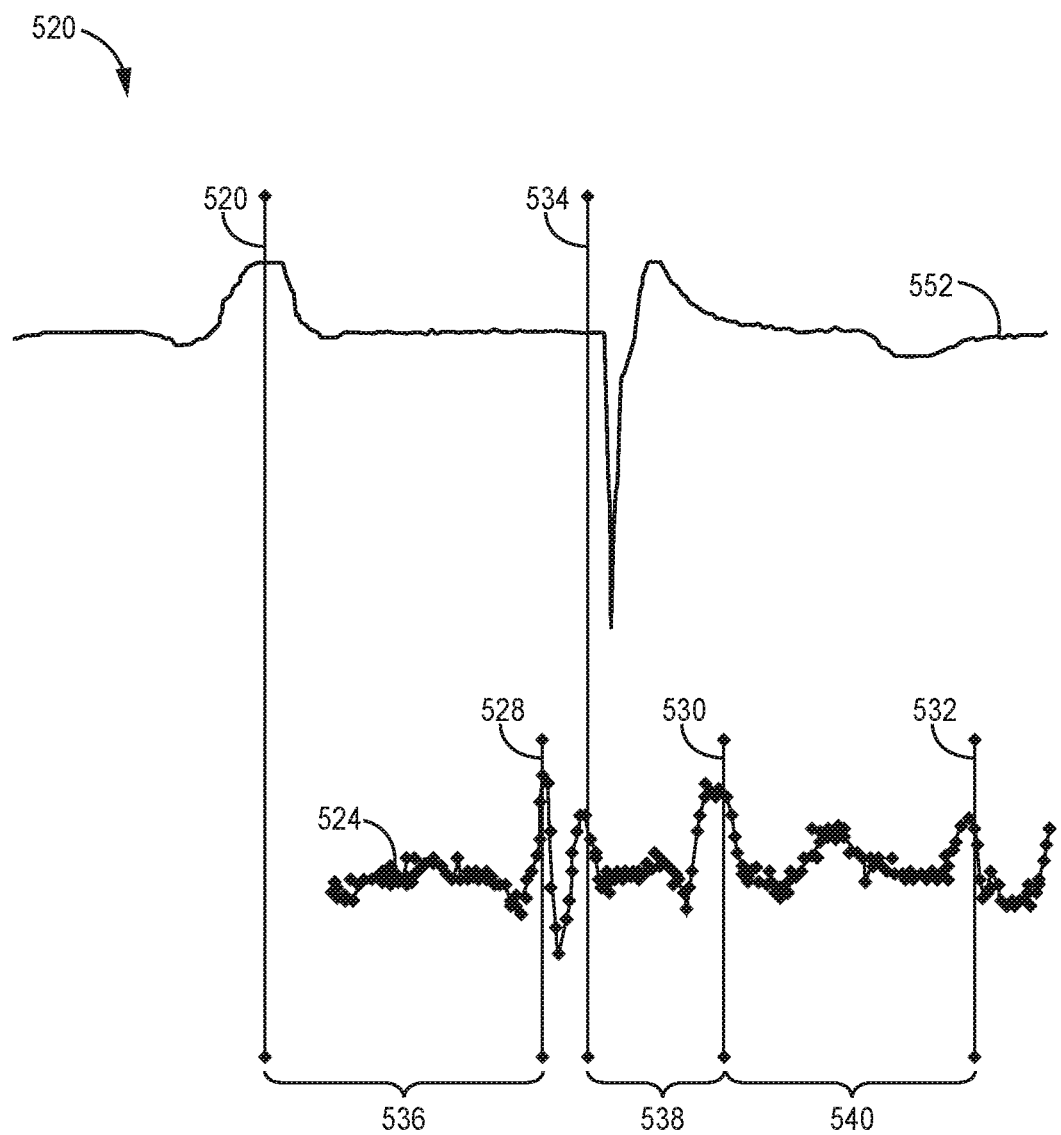
FIG. 17 is a plot of illustrative electrical and mechanical activity signals that may be detected using, e.g., the implantable medical device of FIG. 16.

The various contractions of the patient's heart may be distinguished in data from the motion detector. FIG. 17 shows a plot 520 of signal readings from one or more electrodes and a motion detector of an LPD, such as LPD 500 (FIG. 16). In particular, the plot 520 shows an EGM signal 522 and a motion signal 524 over a time period. The motion signal 524 shows signatures from, for example, an accelerometer in the LPD 500 implanted in the RA. The signatures of mechanical activity may indicate an atrial contraction event 528, a start of LV contraction event 530 (or opening of the mitral closure), and a start of diastole event 532 (or closing of the aortic valve). The EGM signal 522 and the motion signal 524 are also shown in relation to an atrial activation 526 and a ventricular activation 534, either of which may be an intrinsic or a paced event. The paced atrial activation may be, for example, detected in response to delivering a pacing pulse delivered from the therapy delivery circuit.

The use of a motion detector and electrodes may allow electrical activity of the patient's heart to serve as an electrical reference for the mechanical activity of the patient's heart. In particular, the atrial activation can serve as a reference for the atrial contraction. The electrical and mechanical activity can be used as markers not only for traditional AV pacing but also for electromechanical timing intervals.

Various electromechanical intervals may be determined and evaluated to indicate various conditions of the patient's heart. As used herein, the term electromechanical interval is used to describe an interval between an electrical activity event and a mechanical activity event, between two electrical activity events, or between two mechanical activity events. In particular, an electromechanical interval represents an interval between different events during one heartbeat.

One example of an electromechanical interval 536 is based on the atrial activation 526 and the atrial contraction event 528. The atrial activation to contraction interval 536 may be used to determine an AV pacing interval, which may also be described as an AV pacing delay. In particular, the AV pacing interval may be set to only a value larger than the atrial activation to contraction interval 538. Alternatively, or in addition, the AV pacing interval may be set to a value no larger than a certain percentage (e.g., 80%) of the interval between atrial activation 526 and intrinsic ventricular activation.

The AV pacing interval may be used to pace the ventricle, such as the LV, after detecting an intrinsic activation of the atrium, such as the RA. One or more pacing pulses may be delivered to the ventricle using the ventricular electrode 506 implanted in the AV septal wall 512. The AV pacing interval may be determined during or after implantation of the LPD, which may be used by the LPD after implantation while the patient is ambulatory.

In some embodiments, the AV pacing interval may be determined based on monitored electrical activity from an electrode apparatus having a plurality of external electrodes. For example, an ECG apparatus may be used to optimize one or more pacing parameters based on SDAT or LVAT. Such parameters may include, but are not limited to, an AV pacing interval, a pacing vector, and a pacing output. The particular AV pacing interval determined based on this monitored electrical activity may be described as an optimized AV pacing interval.

Another example of an electromechanical interval 538 is based on ventricular activation 534 and the start of an LV contraction event 530 (such as mitral valve closure). The ventricular activation to contraction interval 538 may be used to determine whether the AV pacing interval is acceptable for cardiac therapy.

For example, the intrinsic ventricular activation to contraction interval may be compared to the paced ventricular activation to contraction interval. The comparison of the intrinsic and paced measurements of this interval, from different heartbeats, may be used to determine whether the AV pacing interval is acceptable for cardiac therapy.

In another example, the paced ventricular activation to contraction interval 538 using the optimized AV pacing interval, for example, measured after implantation while the patient is in the clinic, may be compared to the paced ventricular activation to contraction interval 538 measured a period of time after the intrinsic measurement, for example, while the patient is ambulatory. To evaluate long term changes in the patient's heart, the period of time may be on the order of weeks or months. The comparison of the earlier and later paced measurements of this interval at different points in time may be used to determine whether the AV pacing interval is acceptable for cardiac therapy. The optimal AV pacing interval may change for the patient's heart over time, for example, due to remodeling.

In some embodiments, a threshold electromechanical interval may be determined, for example, based on the intrinsic measured interval or the earlier measured interval, and the paced measured interval or the later measured interval may be compared to the respective threshold to determine whether the AV pacing interval is acceptable for cardiac therapy.

In one or more embodiments, the paced ventricular activation to contraction interval 538 may be deemed unacceptable in response to being longer than a predetermined percentage of an intrinsic ventricular activation to contraction interval 538. For example, the threshold or predetermined percentage may be equal to about 90%, about 85%, or even about 80% of the intrinsic ventricular activation to contraction interval 538.

A further example of an electromechanical interval 540 is based on the start of the LV contraction event 530 and the start of the diastole event 532. The ventricular contraction to diastole interval 540 may be used to determine whether the AV pacing interval is acceptable for cardiac therapy. The ventricular contraction to diastole interval 540 may be evaluated in the same or a similar manner to evaluating the ventricular activation to contraction interval 538. In particular, the intrinsic LV contraction to diastole interval may be compared to the paced LV contraction to diastole interval, or an earlier LV contraction to diastole interval may be compared to a later LV contraction to diastole interval. In either case, the comparison may be used to determine whether the AV pacing interval is acceptable for cardiac therapy, for example, using a threshold based on the intrinsic or earlier interval.

In one or more embodiments, the paced ventricular contraction to diastole interval 540 may be deemed unacceptable in response to being shorter than a predetermined percentage of the intrinsic ventricular contraction to diastole interval 540. For example, the threshold or predetermined percentage may be equal to about 110%, about 115%, or even about 120%, about 130%, about 140%, or even about 150% of the intrinsic ventricular contraction to diastole interval 540.

In response to the measured one or more electromechanical intervals being unacceptable, the AV pacing interval may be adjusted. In general, the AV pacing interval may be shortened in response to at least one electromechanical interval being deemed unacceptable for cardiac therapy.

Mechanical activity events detectable in the motion signal 524 may be confirmed, referenced, or calibrated using heart sound measurements, which may be seen on a phonocardiogram. The term heart sound refers to a feature of a heart sound signal, such as the S1, S2, S3, or S4 heart sounds. There may be multiple heart sounds, e.g., each of an S1, S2, S3 and S4 heart sound, for any given cardiac cycle or heartbeat. Heart sounds may be detected, or measured, using any suitable technique known to one of ordinary skill in the art having the benefit of this disclosure. For example, a heart sound sensor may be included in the medical device system, such as in the LPD 500, and may be formed from a piezoelectric material, which may be a piezoelectric ceramic, film, or polymer, or may include a miniaturized microphone. The piezoelectric material may be described as a passive sensor, and the microphone may be described as an active sensor that may require being powered to detect sound.

In general, heart sounds are associated with mechanical vibrations of a patient's heart and the flow of blood through the heart valves and, thus, may be highly correlated with pressure gradients across heart valves and blood pressure. Heart sounds may be not only due to vibrations of and pressure within the heart, but may also be due to the entire cardiohemic system, e.g., blood, heart, great arteries, etc. Heart sounds may recur with each cardiac cycle and are separated and classified according to the activity associated with the vibration.

The first heart sound is referred to as "S1," and can be thought of as the vibration sound made by the heart during closure of the atrioventricular (AV) valves, i.e., the mitral valve and tricuspid valve. The S1 sound can sometimes be broken down into the M1 sound component, from the closing of the mitral valve, and the T1 sound component, from the closing of the tricuspid valve. The second heart sound is referred to as "S2," and results from the closure of the semilunar valves, i.e., the pulmonary and aortic valves. The S2 heart sound can be thought of as marking the beginning of diastole. The S2 sound can also be broken down into component parts. The P2 sound component is from the closing of the pulmonary valve and the A2 sound component is from the closing of the aortic valve. The third and fourth heart sounds are referred to as "S3" and "S4," respectively, and can be conceptualized as related to filling of the ventricles during diastole. S3 is due to rapid filling of the ventricles and can occur when the ventricular wall is not relaxed when a large volume of blood flows into the ventricle from the atria. S4 is caused by blood rapidly filling into the ventricles from the atria due to atrial contraction.

In general, the atrial contraction event 528 may be confirmed or referenced using the S4 heart sound. The start of LV contraction event 530 may be confirmed or referenced using the S1 heart sound or, more specifically, the M1 component of the S1 heart sound. The start of the diastole event 532 may be confirmed to referenced using the S2 heart sound or, more specifically, the A2 component of the S2 heart sound.

Figure 18:
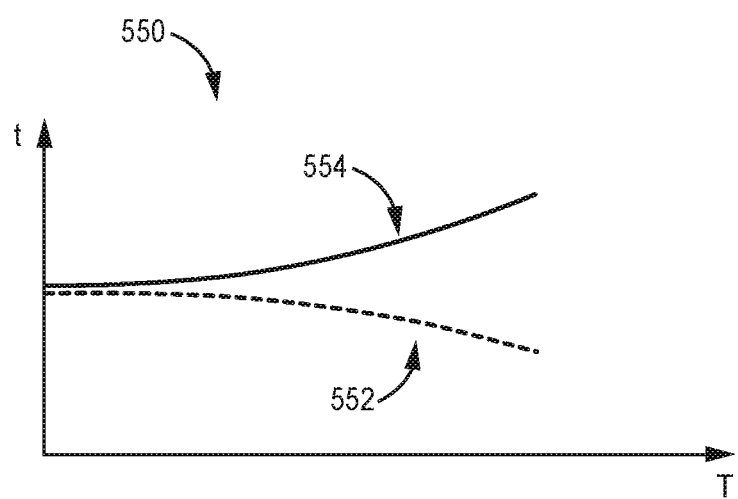
FIG. 18 is a plot of illustrative outcomes that may be determined using, e.g., the implantable medical device of FIG. 16.

Repeated measurements of various intervals over time may be used to indicate whether the patient's heart is experiencing effective remodeling due to cardiac therapy. As can be seen in FIG. 18, a plot 550 of an example interval (t) versus a time horizon (T) shows two example outcomes of cardiac therapy, such as CRT. The example interval may be any electromechanical interval suitable for indicating remodeling, such as the ventricular activation to contraction interval 538 or the ventricular contraction to diastole interval 540.

Trends in the interval data may indicate whether remodeling is effective. For example, a particular electromechanical interval represented by a first data set 552 showing the interval decreasing over a long period of time may indicate effective atrial or ventricular remodeling. A particular electromechanical interval represented by a second data set 554 showing the interval increasing over the same period of time may indicate ineffective atrial or ventricular remodeling, which may also be described as atrial or ventricular relaxation.

Trends in the interval data may be based on measurements made over time. In some embodiments, individual measurements may be made repeatedly, for example, on a periodic basis. Non-limiting examples of periodic repeated measurements include hourly, daily, weekly, or monthly measurements. These individual measurements may be used to plot the trend over a period of time, which may be one or more days, weeks, or months. In one example, a period of time may be equal to about six months.

The measurements may also be aggregated in any suitable manner to provide a practical view of the trend. The measurements in a shorter period of time may be aggregated. In general, the period of time used for aggregating individual measurements is shorter than the period of time used to evaluate the trend. The period of time used to aggregate individual measurements may be limited to intervals longer than one heartbeat.

A plurality of aggregated measurements may be used to plot the trend over time. Non-limiting examples of techniques for aggregating measurements include using the sum, product, average, weighted average, median, variance, or other aggregate function over the period of time. Any suitable period of time may be used for aggregating individual measurements, such as one or more minutes, hours, days, weeks, or months. In one example, the period of time used to aggregate individual measurements may be one week, whereas the period of time used to evaluate the trend may be three months.

A determination that the atrial or ventricular remodeling is ineffective may indicate a high risk of heart failure or atrial fibrillation for the patient. A patient may be alerted to visit a clinic. At a clinic, a clinician may be informed, and the patient may be titrated for better drugs or may be treated using some other action to improve heart failure management.

Figure 19:
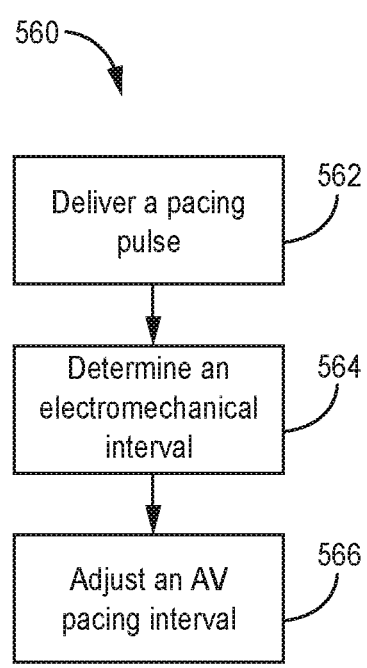
FIG. 19 shows a flowchart of one illustrative method for cardiac therapy using an electromechanical interval for use with, e.g., the implantable medical device of FIG. 16.

FIG. 19 shows one example of a method 560 for cardiac therapy using an electromechanical interval. The method 560 may include delivering a pacing pulse in process 562. The pacing pulse may be delivered according to an AV pacing interval. The method may include determining at least one electromechanical interval in process 564. The electromechanical interval may be based on at least one of electrical activity and mechanical activity. The method 560 may include adjusting an AV pacing interval in process 566. The AV pacing interval may be adjusted based on the electromechanical interval.

In some embodiments, adjusting the AV pacing interval in process 566 may also include determining whether the at least one electromechanical interval is acceptable for cardiac therapy and adjusting the AV pacing interval in response to the at least one electromechanical interval being unacceptable for cardiac therapy.

The method 560 may be repeated any suitable number of times to update the AV pacing interval, for example, to ensure that pacing according to the AV pacing interval is effective over a long period of time. For example, the AV pacing interval may be updated continuously or once every heartbeat, minute, hour, day, or week.

Figure 20:
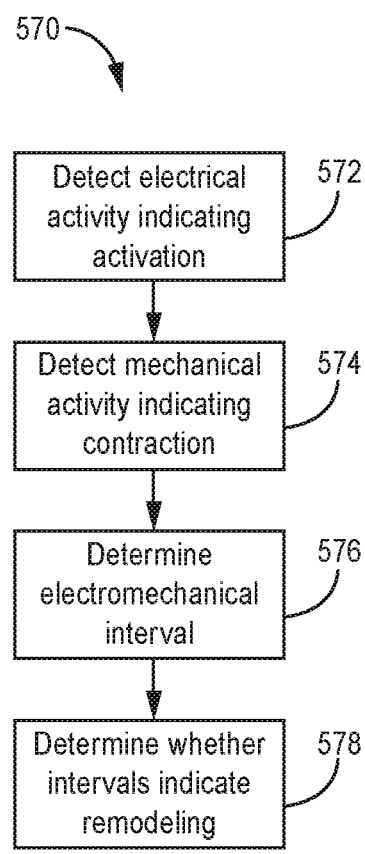
FIG. 20 shows a flowchart of one illustrative method for detecting remodeling using an electromechanical interval for use with, e.g., the implantable medical device of FIG. 16.

FIG. 20 shows one example of a method 570 for detecting heart chamber remodeling using an electromechanical interval. The method 570 may include detecting electrical activity indicating activation in process 572. In some embodiments, electrical activity may be detected using an atrial electrode to detect atrial activation or a ventricular electrode to detect ventricular activation.

The method 570 may include detecting mechanical activity indicating contraction in process 574. In some embodiments, mechanical activity may be detected using a motion detector. The mechanical activity may indicate atrial contraction or ventricular contraction. In one or more embodiments, activation and contraction of the same heart chambers may be detected. For example, atrial activation and atrial contraction may be detected. In another example, ventricular activation and ventricular contraction may be detected.

The method 570 may include determining an electromechanical interval in process 576. In some embodiments, the electromechanical interval may be determined as a time interval between an electrical activity event and a mechanical activity event. For example, at least one electromechanical interval may be determined based on atrial activation and atrial contraction. In another example, at least one electromechanical interval may be determined based on ventricular activation and ventricular contraction.

The method 570 may also include determining whether repeated measurements of at least one electromechanical interval indicates remodeling in process 578. The same type of interval may be measured repeatedly over time. In one example, repeated measurements of the atrial activation to contraction interval may indicate atrial remodeling. In another example, repeated measurements of the ventricular activation to contraction interval may indicate ventricular remodeling.

Determining whether the intervals indicate remodeling in process 578 may include determining whether remodeling is effective. In one example, heart chamber remodeling may be effective in response to the atrial activation to contraction interval decreasing over time. In another example, heart chamber remodeling may be effective in response to the ventricular activation to contraction interval decreasing over time.

ILLUSTRATIVE EMBODIMENTS

While the present disclosure is not so limited, an appreciation of various aspects of the disclosure will be gained through a discussion of specific illustrative embodiments provided below. Various modifications of the examples and illustrative embodiments, as well as additional embodiments of the disclosure, will become apparent herein.

In illustrative embodiment A1, an implantable medical device includes a plurality of electrodes. The plurality of electrodes includes a first electrode to be implanted in the atrium of a patient's heart to deliver cardiac therapy or sense electrical activity of the atrium of the patient's heart and a second electrode to be implanted in a septal wall of the patient's heart distal to the first electrode and to deliver cardiac therapy to or sense electrical activity of the ventricle of the patient's heart. The device also includes a motion detector to detect mechanical activity of the patient's heart, a therapy delivery circuit operably coupled to the plurality of electrodes to deliver cardiac therapy to the patient's heart, and a sensing circuit operably coupled to the plurality of electrodes to sense electrical activity of the patient's heart and the motion detector to sense mechanical activity of the patient's heart. The device also includes a controller having processing circuitry operably coupled to the therapy delivery circuit and the sensing circuit. The controller is configured to deliver a pacing pulse according to an atrioventricular (AV) pacing interval using the second electrode, determine at least one electromechanical interval based on at least one of electrical activity and mechanical activity in response to delivering the pacing pulse, and adjust the AV pacing interval based on the at least one electromechanical interval.

In illustrative embodiment A2, a device includes a device according to any A embodiment, wherein to adjust the AV pacing interval, the controller is further configured to determine whether the at least one electromechanical interval is acceptable for cardiac therapy and adjust the AV pacing interval in response to the at least one electromechanical interval being unacceptable for cardiac therapy.

In illustrative embodiment A3, a device includes a device according to any A embodiment, wherein the controller is further configured to determine an atrial activation to contraction interval based on electrical activity indicating atrial activation using the first electrode and mechanical activity indicating atrial contraction using the motion detector, and determine the AV pacing interval based on the determined atrial activation to contraction interval.

In illustrative embodiment A4, a device includes a device according to embodiment A3, wherein the atrial activation detected is an intrinsic atrial activation detected using the first electrode.

In illustrative embodiment A5, a device includes a device according to embodiment A3 or A4, wherein the detected mechanical activity indicating atrial contraction corresponds to an S4 heart sound.

In illustrative embodiment A6, a device includes a device according to any A embodiment, further having a housing including a distal end region. The first electrode is leadlessly coupled to the housing and the second electrode extends leadlessly from the distal end region of the housing. The motion detector, the therapy delivery circuit, the sensing circuit, and the controller are enclosed within the housing.

In illustrative embodiment A7, a device includes a device according to any A embodiment, wherein the first electrode is a right atrial electrode and the second electrode is a tissue-piercing electrode.

In illustrative embodiment A8, a device includes a device according to any A embodiment, wherein the first electrode is implantable in the right atrium (RA) of the patient's heart to deliver cardiac therapy to or sense electrical activity of the RA of the patient's heart and the second electrode is implantable from the triangle of Koch region of the RA of the patient's heart to deliver cardiac therapy to or sense electrical activity of the left ventricle (LV) in the basal region, septal region, or basal-septal region of the left ventricular myocardium of the patient's heart.

In illustrative embodiment A9, a device includes a device according to any A embodiment, wherein the at least one electromechanical interval includes an interval from electrical activity indicating ventricular pacing to mechanical activity indicating mitral valve closure.

In illustrative embodiment A10, a device includes a device according to embodiment A9, wherein the interval from ventricular pacing to mitral valve closure is unacceptable in response to being longer than a predetermined percentage of an interval from intrinsic ventricular activation to mitral valve closure.

In illustrative embodiment A11, a device includes a device according to embodiment A9 or A10, wherein the mechanical activity indicating mitral valve closure corresponds to an S1 heart sound.

In illustrative embodiment A12, a device includes a device according to any A embodiment, wherein the at least one electromechanical interval includes an interval from mechanical activity indicating mitral valve closure to mechanical activity indicating aortic valve closure in response to ventricular pacing.

In illustrative embodiment A13, a device includes a device according to embodiment A12, wherein the interval from mitral valve closure to aortic valve closure in response to ventricular pacing is unacceptable in response to being shorter than a predetermined percentage of an interval from intrinsic mitral valve closure to intrinsic aortic valve closure.

In illustrative embodiment A14, a device includes a device according to embodiment A12 or A13, wherein the mechanical activity indicating aortic valve closure corresponds to an S2 heart sound.

In illustrative embodiment A15, a device includes a device according to any A embodiment, wherein the AV pacing interval is shortened in response to the at least one electromechanical interval being unacceptable for cardiac therapy.

In illustrative embodiment A16, a device includes a device according to any A embodiment, wherein to determine whether the at least one electromechanical interval is acceptable for cardiac therapy includes comparing the at least one electromechanical interval to a respective threshold electromechanical interval, wherein the respective threshold electromechanical interval is determined using a particular AV pacing interval. The particular AV pacing interval is determined based on monitored electrical activity from an electrode apparatus including a plurality of external electrodes.

In illustrative embodiment B1, an implantable medical device includes a plurality of electrodes. The plurality of electrodes includes a first electrode to be implanted in the atrium of a patient's heart to deliver cardiac therapy or sense electrical activity of the atrium of the patient's heart and a second electrode to be implanted in a septal wall of the patient's heart distal to the first electrode and to deliver cardiac therapy to or sense electrical activity of the ventricle of the patient's heart. The device also includes a motion detector to detect mechanical activity of the patient's heart, a therapy delivery circuit operably coupled to the plurality of electrodes to deliver cardiac therapy to the patient's heart, and a sensing circuit operably coupled to the plurality of electrodes to sense electrical activity of the patient's heart and the motion detector to sense mechanical activity of the patient's heart. The device also includes a controller having processing circuitry operably coupled to the therapy delivery circuit and the sensing circuit. The controller is configured to detect electrical activity from the first electrode indicating atrial activation, detect mechanical activity from the motion detector indicating atrial contraction, determine at least one electromechanical interval based on the detected atrial activation and the detected atrial contraction, and determine whether repeated measurements of the at least one electromechanical interval indicate atrial remodeling.

In illustrative embodiment B2, a device includes a device according to any B embodiment, wherein the controller is further configured to determine whether repeated measurements of the at least one electromechanical interval indicate effective atrial remodeling based on an atrial activation to contraction interval decreasing over time.

In illustrative embodiment C1, an implantable medical device includes a plurality of electrodes. The plurality of electrodes includes a first electrode to be implanted in the atrium of a patient's heart to deliver cardiac therapy or sense electrical activity of the atrium of the patient's heart and a second electrode to be implanted in a septal wall of the patient's heart distal to the first electrode and to deliver cardiac therapy to or sense electrical activity of the ventricle of the patient's heart. The device also includes a motion detector to detect mechanical activity of the patient's heart, a therapy delivery circuit operably coupled to the plurality of electrodes to deliver cardiac therapy to the patient's heart, and a sensing circuit operably coupled to the plurality of electrodes to sense electrical activity of the patient's heart and the motion detector to sense mechanical activity of the patient's heart. The device also includes a controller having processing circuitry operably coupled to the therapy delivery circuit and the sensing circuit. The controller is configured to detect electrical activity indicating ventricular activation using the second electrode, detect mechanical activity using the motion detector indicating ventricular contraction, determine at least one electromechanical interval based on the detected ventricular activation and the detected ventricular contraction, and determine whether repeated measurements of the at least one electromechanical interval indicate ventricular remodeling.

In illustrative embodiment C2, a device includes a device according to any C embodiment, wherein the controller is further configured to determine whether repeated measurements of the at least one electromechanical interval indicate effective ventricular remodeling based on a ventricular activation to contraction interval decreasing over time.

In illustrative embodiment C3, a device includes a device according to any C embodiment, wherein the at least one electromechanical interval includes an interval from electrical activity indicating ventricular pacing to mechanical activity indicating mitral valve closure.

In illustrative embodiment C4, a device includes a device according to embodiment C3, wherein the mechanical activity indicating mitral valve closure corresponds to an S1 heart sound.

In illustrative embodiment C5, a device includes a device according to any C embodiment, wherein the at least one electromechanical interval includes an interval from mechanical activity indicating mitral valve closure to mechanical activity indicating aortic valve closure in response to ventricular pacing.

In illustrative embodiment C6, a device includes a device according to embodiment C5, wherein the mechanical activity indicating aortic valve closure corresponds to an S2 heart sound.

In illustrative embodiment D1, a method includes delivering a pacing pulse to a patient's heart according to an atrioventricular (AV) pacing interval. The method also includes determining at least one electromechanical interval based on at least one of electrical activity and mechanical activity detected in response to delivering the pacing pulse. The method also includes adjusting the AV pacing interval based on the at least one electromechanical interval.

In illustrative embodiment D2, a method includes a method according to any D embodiment, wherein adjusting the AV pacing interval includes determining whether the at least one electromechanical interval is acceptable for cardiac therapy and adjusting the AV pacing interval in response to the at least one electromechanical interval being unacceptable for cardiac therapy.

In illustrative embodiment D3, a method includes a method according to any D embodiment, further including determining whether repeated measurements of the at least one electromechanical interval indicate effective atrial remodeling.

In illustrative embodiment D4, a method includes a method according to any D embodiment, further including determining whether repeated measurements of the at least one electromechanical interval indicate effective ventricular remodeling.

Thus, various embodiments of the CARDIAC RESYNCHRONIZATION THERAPY USING ACCELEROMETER are disclosed. Although reference is made herein to the accompanying set of drawings that form part of this disclosure, one of at least ordinary skill in the art will appreciate that various adaptations and modifications of the embodiments described herein are within, or do not depart from, the scope of this disclosure. For example, aspects of the embodiments described herein may be combined in a variety of ways with each other. Therefore, it is to be understood that, within the scope of the appended claims, the claimed invention may be practiced other than as explicitly described herein.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

All references and publications cited herein are expressly incorporated herein by reference in their entirety for all purposes, except to the extent any aspect directly contradicts this disclosure.

All scientific and technical terms used herein have meanings commonly used in the art unless otherwise specified. The definitions provided herein are to facilitate understanding of certain terms used frequently herein and are not meant to limit the scope of the present disclosure.

Unless otherwise indicated, all numbers expressing feature sizes, amounts, and physical properties used in the specification and claims may be understood as being modified either by the term "exactly" or "about." Accordingly, unless indicated to the contrary, the numerical parameters set forth in the foregoing specification and attached claims are approximations that can vary depending upon the desired properties sought to be obtained by those skilled in the art utilizing the teachings disclosed herein or, for example, within typical ranges of experimental error.

The recitation of numerical ranges by endpoints includes all numbers subsumed within that range (e.g. 1 to 5 includes 1, 1.5, 2, 2.75, 3, 3.80, 4, and 5) and any range within that range. Herein, the terms "up to" or "no greater than" a number (e.g., up to 50) includes the number (e.g., 50), and the term "no less than" a number (e.g., no less than 5) includes the number (e.g., 5).

Terms related to orientation, such as "proximal" or "distal" are used to describe relative positions of components and are not meant to limit the orientation of the embodiments contemplated.

The terms "coupled" or "connected" refer to elements being attached to each other either directly (in direct contact with each other) or indirectly (having one or more elements between and attaching the two elements). Either term may be modified by "operatively" and "operably," which may be used interchangeably, to describe that the coupling or connection is configured to allow the components to interact to carry out functionality.

As used herein, the term "configured to" may be used interchangeably with the terms "adapted to" or "structured to" unless the content of this disclosure clearly dictates otherwise.

Th singular forms "a," "an," and "the" encompass embodiments having plural referents unless its context clearly dictates otherwise.

The term "or" is generally employed in its inclusive sense, for example, to mean "and/or" unless the context clearly dictates otherwise.

The term "and/or" means one or all of the listed elements or a combination of at least two of the listed elements.

The phrases "at least one of," "comprises at least one of," and "one or more of" followed by a list refers to any one of the items in the list and any combination of two or more items in the list.

As used herein, "have," "having," "include," "including," "comprise," "comprising" or the like are used in their open-ended sense, and generally mean "including, but not limited to." It will be understood that "consisting essentially of," "consisting of" and the like are subsumed in "comprising," and the like.

Reference to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout are not necessarily referring to the same embodiment of the disclosure. Furthermore, the particular features, configurations, compositions, or characteristics may be combined in any suitable manner in one or more embodiments.

The invention claimed is:

1. An implantable medical device comprising:
   a plurality of electrodes comprising:
      a first electrode configured to be implanted in an atrium of a patient's heart to deliver a cardiac therapy or sense atrial electrical activity of the atrium of the patient's heart; and
      a second electrode configured to be implanted in a septal wall of the patient's heart distal to the first electrode and to deliver the cardiac therapy to or sense ventricular electrical activity of a ventricle of the patient's heart;
   a motion detector to detect mechanical activity of the patient's heart;
   a therapy delivery circuit operably coupled to the plurality of electrodes to deliver the cardiac therapy to the patient's heart;
   a sensing circuit operably coupled to the plurality of electrodes to sense the atrial electrical activity and the ventricular electrical activity of the patient's heart, and operably coupled to the motion detector to sense the mechanical activity of the patient's heart; and
   a controller comprising processing circuitry operably coupled to the therapy delivery circuit and the sensing circuit, the controller configured to:
      deliver at least one pacing pulse of the cardiac therapy according to an atrioventricular (AV) pacing interval using the second electrode;
      determine at least one electromechanical interval based on one or more of the atrial electrical activity, the ventricular electrical activity, and the mechanical activity in response to delivering the at least one pacing pulse, wherein the at least one electromechanical interval is based on at least the mechanical activity in response to delivering the at least one pacing pulse, and wherein the at least one electromechanical interval comprises an interval from the ventricular electrical activity indicating ventricular pacing to the mechanical activity indicating mitral valve closure; and
      adjust the AV pacing interval based on the at least one electromechanical interval.

2. The device according to claim 1, wherein, to adjust the AV pacing interval based on the at least one electromechanical interval, the controller is further configured to:
   determine whether the at least one electromechanical interval is acceptable for the cardiac therapy; and
   adjust the AV pacing interval in response to the at least one electromechanical interval being unacceptable for the cardiac therapy.

3. The device according to claim 1 or 2, wherein the at least one electromechanical interval comprises an interval from the atrial electrical activity indicating atrial activation to the mechanical activity indicating atrial contraction.

4. The device according to claim 3, wherein the atrial activation detected is an intrinsic atrial activation detected using the first electrode.

5. The device according to claim 4, wherein the mechanical activity indicating atrial contraction corresponds to an S4 heart sound.

6. The device according to claim 1, further comprising a housing including a distal end region, wherein the first electrode is leadlessly coupled to the housing and the second electrode extends leadlessly from the distal end region of the housing, and wherein the motion detector, the therapy delivery circuit, the sensing circuit, and the controller are enclosed within the housing.

7. The device according to claim 1, wherein the first electrode is a right atrial electrode and the second electrode is a tissue-piercing electrode.

8. The device according to claim 1, wherein the first electrode is configured to be implanted in the right atrium (RA) of the patient's heart to deliver the cardiac therapy to or sense the atrial electrical activity of the RA of the patient's heart and the second electrode is configured to be implanted in the triangle of Koch region of the RA of the patient's heart to deliver the cardiac therapy to or sense the ventricular electrical activity of the left ventricle (LV) in the basal region, septal region, or basal-septal region of the left ventricular myocardium of the patient's heart.

9. The device according to claim 2, wherein the interval from ventricular pacing to mitral valve closure is unacceptable in response to being longer than a predetermined percentage of an interval from intrinsic ventricular activation to mitral valve closure.

10. The device according to claim 1 or 9, wherein the mechanical activity indicating mitral valve closure corresponds to an S1 heart sound.

11. The device according to claim 2, wherein adjusting the AV pacing interval in response to the at least one electromechanical interval being unacceptable for the cardiac therapy comprises shortening the AV pacing interval in response to the at least one electromechanical interval being unacceptable for the cardiac therapy.

12. The device according to claim 2, wherein, to determine whether the at least one electromechanical interval is acceptable for the cardiac therapy, the controller is further configured to:
receive electrical activity from an external electrode apparatus comprising a plurality of external electrodes;
determine a particular AV pacing interval based on the received electrical activity;
determine a respective threshold electromechanical interval using the particular AV pacing interval; and
compare the at least one electromechanical interval to the respective threshold electromechanical interval.

13. The device according to claim 1, wherein to determine the at least one electromechanical interval, the controller is further configured to determine the at least one electromechanical interval based on the mechanical activity in response to delivering the at least one pacing pulse and based on one or more of the atrial electrical activity and the ventricular electrical activity.

14. An implantable medical device comprising:
a plurality of electrodes comprising:
a first electrode configured to be implanted in an atrium of a patient's heart to deliver a cardiac therapy or sense atrial electrical activity of the atrium of the patient's heart; and
a second electrode configured to be implanted in a septal wall of the patient's heart distal to the first electrode and to deliver the cardiac therapy to or sense ventricular electrical activity of a ventricle of the patient's heart;
a motion detector to detect mechanical activity of the patient's heart;
a therapy delivery circuit operably coupled to the plurality of electrodes to deliver the cardiac therapy to the patient's heart;
a sensing circuit operably coupled to the plurality of electrodes to sense the atrial electrical activity and the ventricular electrical activity of the patient's heart, and operably coupled to the motion detector to sense the mechanical activity of the patient's heart; and
a controller comprising processing circuitry operably coupled to the therapy delivery circuit and the sensing circuit, the controller configured to:
deliver at least one pacing pulse of the cardiac therapy according to an atrioventricular (AV) pacing interval using the second electrode;
determine at least one electromechanical interval based on one or more of the atrial electrical activity, the ventricular electrical activity, and the mechanical activity in response to delivering the at least one pacing pulse, wherein the at least one electromechanical interval is based on at least the mechanical activity in response to delivering the at least one pacing pulse; and
adjust the AV pacing interval based on the at least one electromechanical interval,
wherein, to adjust the AV pacing interval based on the at least one electromechanical interval, the controller is further configured to:
determine whether the at least one electromechanical interval is acceptable for the cardiac therapy; and
adjust the AV pacing interval in response to the at least one electromechanical interval being unacceptable for the cardiac therapy,
wherein, to determine whether the at least one electromechanical interval is acceptable for the cardiac therapy, the controller is further configured to:
receive electrical activity from an external electrode apparatus comprising a plurality of external electrodes;
determine a particular AV pacing interval based on the received electrical activity;
determine a respective threshold electromechanical interval using the particular AV pacing interval; and
compare the at least one electromechanical interval to the respective threshold electromechanical interval.

15. The device according to claim 14, wherein the at least one electromechanical interval comprises an interval from the atrial electrical activity indicating atrial activation to the mechanical activity indicating atrial contraction.

16. The device according to claim 15, wherein the atrial activation detected is an intrinsic atrial activation detected using the first electrode.

17. The device according to claim 16, wherein the mechanical activity indicating atrial contraction corresponds to an S4 heart sound.

18. The device according to claim 14, further comprising a housing including a distal end region, wherein the first electrode is leadlessly coupled to the housing and the second electrode extends leadlessly from the distal end region of the housing, and wherein the motion detector, the therapy delivery circuit, the sensing circuit, and the controller are enclosed within the housing.

19. The device according to claim 14, wherein the first electrode is a right atrial electrode and the second electrode is a tissue-piercing electrode.

20. The device according to claim 14, wherein the first electrode is configured to be implanted in the right atrium (RA) of the patient's heart to deliver the cardiac therapy to or sense the atrial electrical activity of the RA of the patient's heart and the second electrode is configured to be implanted in the triangle of Koch region of the RA of the patient's heart to deliver the cardiac therapy to or sense the ventricular electrical activity of the left ventricle (LV) in the basal region, septal region, or basal-septal region of the left ventricular myocardium of the patient's heart.

21. The device according to claim 14, wherein the at least one electromechanical interval comprises an interval from the ventricular electrical activity indicating ventricular pacing to the mechanical activity indicating mitral valve closure, and wherein the interval from ventricular pacing to mitral valve closure is unacceptable in response to being longer than a predetermined percentage of an interval from intrinsic ventricular activation to mitral valve closure.

22. The device according to claim 21, wherein the mechanical activity indicating mitral valve closure corresponds to an S1 heart sound.

23. The device according to claim 14, wherein adjusting the AV pacing interval in response to the at least one electromechanical interval being unacceptable for the cardiac therapy comprises shortening the AV pacing interval in response to the at least one electromechanical interval being unacceptable for the cardiac therapy.

24. The device according to claim 14, wherein to determine the at least one electromechanical interval, the controller is further configured to determine the at least one electromechanical interval based on the mechanical activity in response to delivering the at least one pacing pulse and based on one or more of the atrial electrical activity and the ventricular electrical activity.

\* \* \* \* \*